United States Patent
Harris et al.

(10) Patent No.: US 11,186,639 B2
(45) Date of Patent: Nov. 30, 2021

(54) MULTISPECIFIC HEAVY CHAIN ANTIBODIES WITH MODIFIED HEAVY CHAIN CONSTANT REGIONS

(71) Applicant: TeneoOne, Inc., Newark, CA (US)

(72) Inventors: Katherine Harris, Newark, CA (US); Ute Schellenberger, Newark, CA (US); Omid Vafa, Newark, CA (US); Nathan Trinklein, Newark, CA (US); Wim van Schooten, Newark, CA (US); Shelley Force Aldred, Newark, CA (US); Duy Pham, Newark, CA (US); Starlynn Clarke, Newark, CA (US)

(73) Assignee: TENEOONE, INC., Newark, CA (US)

( * ) Notice: Subject to any disclaimer, the term of this patent is extended or adjusted under 35 U.S.C. 154(b) by 0 days.

(21) Appl. No.: 17/308,946

(22) Filed: May 5, 2021

(65) Prior Publication Data

US 2021/0340255 A1 Nov. 4, 2021

Related U.S. Application Data

(63) Continuation of application No. PCT/US2021/029909, filed on Apr. 29, 2021.

(60) Provisional application No. 63/017,589, filed on Apr. 29, 2020, provisional application No. 63/108,796, filed on Nov. 2, 2020.

(51) Int. Cl.
C07K 16/28 (2006.01)

(52) U.S. Cl.
CPC ...... *C07K 16/2809* (2013.01); *C07K 16/2878* (2013.01); *C07K 2317/31* (2013.01); *C07K 2317/565* (2013.01)

(58) Field of Classification Search
CPC ............ C07K 16/2809; C07K 16/2878; C07K 2317/31; C07K 2317/565
See application file for complete search history.

(56) References Cited

U.S. PATENT DOCUMENTS

| | | | |
|---|---|---|---|
| 4,816,567 A | 3/1989 | Cabilly et al. | |
| 5,500,362 A | 3/1996 | Robinson et al. | |
| 5,585,097 A | 12/1996 | Bolt et al. | |
| 5,821,337 A | 10/1998 | Carter et al. | |
| 5,929,212 A | 7/1999 | Jolliffe et al. | |
| 5,968,509 A | 10/1999 | Gorman et al. | |
| 6,706,265 B1 | 3/2004 | Bolt et al. | |
| 6,750,325 B1 | 6/2004 | Jolliffe et al. | |
| 7,262,276 B2 | 8/2007 | Huang et al. | |
| 7,381,803 B1 | 6/2008 | Weiner et al. | |
| 7,541,513 B2 | 6/2009 | Bruggemann et al. | |
| 7,635,472 B2 | 12/2009 | Kufer et al. | |
| 7,728,114 B2 | 6/2010 | Mach et al. | |
| 7,862,813 B2 | 1/2011 | Bjork et al. | |
| 8,236,308 B2 | 8/2012 | Kischel et al. | |
| 8,367,888 B2 | 2/2013 | Bruggemann et al. | |
| 8,883,150 B2 | 11/2014 | Craig et al. | |
| 9,034,324 B2 | 5/2015 | Kalled et al. | |
| 9,365,655 B2 | 6/2016 | Craig et al. | |
| 2001/0024811 A1 | 9/2001 | Khosla et al. | |
| 2001/0024812 A1 | 9/2001 | Guegler et al. | |
| 2002/0066516 A1 | 6/2002 | Cornell | |
| 2004/0229310 A1 | 11/2004 | Simmons | |
| 2005/0048572 A1 | 3/2005 | Reilly et al. | |
| 2006/0008548 A1 | 1/2006 | Tung | |
| 2007/0065437 A1 | 3/2007 | Elson et al. | |
| 2009/0098134 A1 | 4/2009 | Buelow | |
| 2010/0122358 A1 | 5/2010 | Bruggemann et al. | |
| 2013/0156769 A1 | 6/2013 | Kufer et al. | |
| 2013/0273055 A1 | 10/2013 | Borges et al. | |
| 2015/0266966 A1 | 9/2015 | Smith et al. | |
| 2015/0368351 A1 | 12/2015 | Vu et al. | |
| 2015/0376287 A1 | 12/2015 | Vu et al. | |
| 2016/0046724 A1 | 2/2016 | Brogdon et al. | |
| 2016/0159894 A1 | 6/2016 | Hartmann et al. | |
| 2016/0166689 A1 | 6/2016 | Adler et al. | |
| 2016/0194399 A1 | 7/2016 | Irving et al. | |
| 2016/0355591 A1 | 12/2016 | Goldenberg et al. | |
| 2019/0106504 A1 | 4/2019 | Wu et al. | |
| 2019/0352412 A1 | 11/2019 | Force Aldred et al. | |
| 2020/0048348 A1 | 2/2020 | Trinklein et al. | |
| 2020/0085839 A1 | 3/2020 | Sidransky et al. | |

(Continued)

FOREIGN PATENT DOCUMENTS

| | | |
|---|---|---|
| RU | 2492186 | 9/2013 |
| RU | 2561457 | 8/2015 |

(Continued)

OTHER PUBLICATIONS

Wang et al., "A systematic approach for analysis and characterization of mispairing in bispecific antibodies with asymmetric architecture," (2018) mAbs 10:8, 1226-1235.

Ridgway et al., "'Knobs-into-holes' engineering of antibody CH3 domains for heavy chain heterodimerization," (1996) Protein Eng. 9(7):617-621.

Gupta et al., "Constitutive Inflammatory Cytokine Storm: A Major Threat to Human Health," (2019) Journal of Interferon & Cytokine Research 40(1):19-23.

Crescioli et al., "IgG4 Characteristics and Functions in Cancer Immunity," (2016) Curr Allergy Asthma Rep 16:7.

(Continued)

*Primary Examiner* — Julie Wu
*Assistant Examiner* — Cheom-Gil Cheong
(74) *Attorney, Agent, or Firm* — Benjamin C. Pelletier; Haynes and Boone LLP

(57) ABSTRACT

Multispecific, human heavy chain antibodies (e.g., Uni-Abs™) that have modified heavy chain constant regions that impart advantageous properties are provided. The invention further concerns methods of making such antibodies, compositions, including pharmaceutical compositions, comprising such antibodies, and their use to treat disorders that are characterized by expression of one or more of the binding targets described herein.

20 Claims, 35 Drawing Sheets

Specification includes a Sequence Listing.

(56) References Cited

U.S. PATENT DOCUMENTS

| | | | |
|---|---|---|---|
| 2020/0157232 | A1 | 5/2020 | Trinklein et al. |
| 2020/0339685 | A1 | 10/2020 | Schellenberger et al. |
| 2021/0047402 | A1 | 2/2021 | Trinklein et al. |

FOREIGN PATENT DOCUMENTS

| | | | |
|---|---|---|---|
| WO | 1996/027011 | 9/1993 | |
| WO | 1996/027011 | 9/1996 | |
| WO | 1996/032478 | 10/1996 | |
| WO | 1997/034631 | 9/1997 | |
| WO | 1998/050431 | 11/1998 | |
| WO | 2001/024811 | 4/2001 | |
| WO | 2001/024812 | 4/2001 | |
| WO | 2002/066516 | 8/2002 | |
| WO | 2006/008548 | 1/2006 | |
| WO | 2010/109165 | 9/2010 | |
| WO | 2011/097603 | 8/2011 | |
| WO | 2014/022540 | 2/2014 | |
| WO | 2014/047231 | 3/2014 | |
| WO | 2014/068079 | 5/2014 | |
| WO | 2014/089335 | 6/2014 | |
| WO | 2014/093908 | 6/2014 | |
| WO | 2015/095412 | 6/2015 | |
| WO | 2015/121383 | 8/2015 | |
| WO | 2016/079081 | 5/2016 | |
| WO | 2016/079177 | 5/2016 | |
| WO | 2017/025038 | 2/2017 | |
| WO | 2017/031104 | 2/2017 | |
| WO | 2017/223111 | 12/2017 | |
| WO | 2018/052503 | 3/2018 | |
| WO | 2018/237037 | 12/2018 | |
| WO | 2019/006072 | 1/2019 | |
| WO | 2020/018922 | 1/2020 | |
| WO | WO-2020206330 A1 * | 10/2020 | ......... C07K 16/3069 |

OTHER PUBLICATIONS

Labrijn et al., "Therapeutic IgG4 antibodies engage in Fab-arm exchange with endogenous human IgG4 in vivo," (2009) Nature Biotechnology 27:767-71.
Muyldermans, "Single domain camel antibodies: current status," 2001; Journal of Biotechnology 74(4):277-302.
Revets et al., "Nanobodies as Novel Agents for Cancer Therapy," (2005) Expert Opinion Biological Therapy 5(1):111-124.
Nuttall et al., "Isolation and Characterization of an IgNAR Variable Domain Specific for the Human Mitochondrial Translocase Receptor Tom70," (2003) Eur. J. Biochem. 270:3543-3554.
Nuttall et al., "Selection and Affinity Maturation of IgNAR Variable Domains Targeting Plasmodium falciparum AMA1," (2004) Proteins; Structure, Function and Bioinformatics 55:187-197.
Dooley et al., "Selection and Characterization of Naturally Occuring Single-domain (IgNAR) Antibody Fragments from Immunized Sharks by Phage Display," (2003) Molecular Immunology 40:25-33.
Jaton et al., "Recovery of Antibody Activity Upon Reoxidation of Completely Reduced Polyalanyl Heavy Chain and its Fd Fragment Derived from Anti-2,4-dinitrophenyl Antibody," (1968) Biochemistry 7(12):4185-4195.
Sitia et al., "Developmental Regulation of IgM Secretion: The Role of the Carbosy-terminal Cysteine," (1990) Cell, 60:781-790.
Van der Linden et al., "Comparison of Physical Chemical Properties of Llama $V_{HH}$ Antibody Fragments and Mouse Monoclonal Antibodies," (1999) Biochimica et Biophysica Acta 1431:37-46.
Frenken et al., "Isolation of Antigen Specific Llama $V_{HH}$ Antibody Fragments and Their High Level Secretion by Saccharomyces cerevisiae," (2000) J. Biotechnol. 78:11-21.
Ghahroudi et al., "Selection and Identification of Single Domain Antibody Fragments from Camel Heavy-chain Antibodies," (1997) FEBS Letters 414:521-526.
Nguyen et al., "Heavy-chain only antibodies derived from dromedary are secreted and displayed by mouse B cells," (2003) Immunology; 109(1):93-101.

Bruggemann et al., "Heavy-Chain-Only Antibody Expression and B-Cell Development in the Mouse," (2006) Crit. Rev. Immunol. 26(5):377-90.
Zou et al., "Heavy Chain-Only Antibodies are Spontaneously Produced in Light Chain-Deficient," (2007) J Exp Med 204(13): 3271-3283.
Geurts et al., "Knockout Rats via Embryo Microinjection of Zinc-finger Nucleases," (2009) Science 325(5939):433.
Iri-Sofla et al., "Nanobody-based Chimeric Receptor Gene Integration in Jurkat Cells Mediated by PhiC31 Integrase," (2011) Experimental Cell Research 317:2630-2641.
Jamnani et al., "T Cells Expressing VHH-directed Oligoclonal Chimeric HER2 Antigen Receptors: Towards Tumor-directed Oligoclonal T Cell Therapy," (2014) Biochimica et Biophysica Acta 1840:378-386.
Gras et al., "BCMAp: An Integral Membrane Protein in the Golgi Apparatus of Human Mature B Lymphocytes," (1995) International Immunology 7(7):1093-1106.
Tai et al., "Novel Anti-B-Cell Maturation Antigen Antibody-drug Conjugate (GSK2857916) Selectively Induces Killing of Multiple Myeloma," (2014) Blood 123(20): 3128-38.
Ali et al., "T Cells Expressing an Anti-B-Cell Maturation Antigen Chimeric Antigen Receptor Cause Remissions of Multiple Myeloma," (2016) Blood 128(13):1688-700.
Kohler et al., "Continuous cultures of fused cells secreting antibody of predefined specificity," (1975) Nature 256:495-497.
Chothia et al., "Canonical structures for the hypervariable regions of immunoglobulins," (1987) Journal of Molecular Biology 196(4):901-917.
Lefranc et al., "IMGT, the international ImMunoGeneTics database," (1999) Nucleic Acids Research, 27(1):209-212.
Zhao et al., "A germline knowledge based computational approach for determining antibody complementarity determining regions," (2010) Molecular Immunology 47(4):694-700.
Chothia et al., "Conformations of immunoglobulin hypervariable regions," (1989) Nature 342:877-883.
Honegger, "Yet Another numbering scheme for immunoglobulin variable domains: an automatic modeling and analysis tool," (2001) Journal of Molecular Biology 309(3):657-670.
Ofran et al. "Automated identification of complementarity determining regions (CDRs) reveals peculiar characteristics of CDRs and B-cell epitopes," (2008) Journal of Immunology 181(9):6230-6235.
Almagro "Identification of differences in the specificity-determining residues of antibodies that recognize antigens of different size: implications for the rational design of antibody repertoires," (2004) Journal of Molecular Recognition 17(2):132-143.
Padlan et al., "Identification of specificity-determining residues in antibodies," (1995) FASEB Journal 9(1):133-139.
Roux et al., "Comparisons of the Ability of Human IgG3 Hinge Mutants, IgM, IgE, and IgA2, to Form Small Immune Complexes: A Role for Flexibility and Geometry," (1998) Journal of Immunology 161(8):4083-4090.
Lund et al., "Expression and characterization of truncated forms of humanized L243 IgG1," (2000) European Journal of Biochemistry 267(24):7246-7256.
Boesch et al., "Highly parallel characterization of IgG Fc binding interactions," (2014) MAbs 6(4):915-927.
Chen et al., "Fusion protein linkers: Property, design and functionality," (2013) Advanced Drug Delivery Reviews 65(10): 1357-1369.
Hamers-Casterman et al., "Naturally Occurring Antibodies Devoid of Light Chains," (1993) Letters to Nature 363:446-448.
Desmyter et al., "Antigen Specificity and High Affinity Binding Provided by One Single Loop of a Camel Single-domain Antibody," (2001) Journal of Biological Chemistry 276(28):26285-26290.
Jackson et al., "Driving CAR T-cells Forward," (2016) Nature Reviews Clinical Oncology 13:370-383.
Ravetch et al., "Fc Receptors," (1991) Annual Review of Immunology 9:457-492.
Clynes et al., "Fc Receptors are Required in Passie and Active Immunity to Melanoma," (1998) PNAS (USA) 95(2):652-656.
Gazzano-Santoro et al., "A non-radioactive complement-dependent cytotoxicity assay for anti-CD20 monoclonal antibody," (1996) Journal of Immunological Methods 202(2):163-171.

(56) References Cited

OTHER PUBLICATIONS

Concepcion et al., "Label-Free Detection of Biomolecular Interactions Using BioLayer Interferometry for Kinetic Characterization," (2009) Combinatorial Chemistry & High Throughput Screening 12(8):791-800.
Menoret et al., "Characterization of Immunoglobulin Heavy Chain Knockout Rats," (2010) European Journal Immunology 40:2932-2941.
Cui et al., "Targeted Integration in Rat and Mouse Embryos with Zinc-finger Nucleases," (2011) Nature Biotechnology 29(1):64-67.
Carpenter et al., "B-cell Maturation Antigen Is a Promising Target for Adoptive T-cell Therapy of Multiple Myeloma," (2013) Clinical Cancer Research 19(8):2048-2060.
Tai et al., "APRIL and BCMA promote human multiple myeloma growth and immunosuppression in the bone marrow microenvironment," (2016) Blood 127(25):3225-3236.
Sanz et al., "B Cells as Therapeutic Targets in SLE," (2010) Nature Reviews Rheumatology 6:326-337.
Durben et al., "Characterization of a Bispecific FLT3 X CD3 Antibody in an Improved, Recombinant Format for the Treatment of Leukemia," (2015) Molecular Therapy 23(4):648-655.
Mack et al., "A Small Bispecific Antibody Construct Expressed as a Functional Single-chain Molecule with High Tumor Cell Cytotoxicity," (1995) PNAS 92:7021-7025.
Lindhofer et al., "Preferential Species-restricted Heavy/Light Chain Pairing in Rat/Mouse Quadromas. Implications for a Single-step Purification of Bispecific Antibodies," The Journal of Immunology, 155(1): 219-225.
Link et al., "Anti-CD3-Based Bispecific Antibody Designed for Therapy of Human B-Cell Malignancy can Induce T-cell Activation by Antigen-dependent and Antigen-independent Mechanisms," (1998) Int. J. Cancer 77:251-256.
Glennie et al., "Preparation and Performance of Bispecific F(ab' gamma)2 Antibody Containing Thioether-linked Fab' gamma Fragments," (1987) Journal of Immunology 139(7): 2367-2375.
Borchmann et al., "Phase 1 trial of the Novel Bispecific Molecule H22xKi-4 in Patients with Refractory Hodgkin Lymphoma," (2002) Blood 100(9):3101-3107.
Adams et al., "Prolonged in Vivo Tumour Retention of a Human Diabody Targeting the Extracellular Domain of Human HER2lneu," (1998) British Journal of Cancer 77(9):1405-1412.
Wu et al., "Simultaneous Targeting of Multiple Disease Mediators by a Dual-variable domain Immunoglobulin," (2007) Nature Biotechnology 25:1290-1297.
Yoon et al., "Both High and Low Avidity Antibodies to the T Cell Receptor can have Agonist Activity," (1994) Immunity 1(7) 563-569.
Baas et al., "Superhuman Mice" (2014) Science-Business eXchange 7(17):1-2.
Trinklein et al., "Abstract LB-090: Sequence-based Discovery ofFully Human Anti-CD3 and Anti-PDL 1 Single Domain Antibodies Using Novel Transgenic Rats," (2016) Cancer Research 76(14 Suppl).

Buelow et al., "Development of a fully human T cell engaging bispecfic antibody for the treatment of multiple myeloma," (2017) J Clin OnCol vol. 35 Supplement.
Dai et al., "Chimeric Antigen Receptors Modified T-cells for Cancer Therapy," (2016) J Natl Cancer Inst 108(7):dvj439.
Hotzel et al., "A strategy for risk mitigation of antibodies with fast clearance," (2012) mABs 4(6)753-760.
Janssens et al., "Generation of Heavy-chain-only Antibodies in Mice," (2006) Proceedings of the National Academy of Sciences of the USA 103(41):15130-15135.
Salmeron et al., "A conformational epitope expressed upon association of CD3-epsilon with either CD3-delta or CD3-gamma is the main target for recognition by anti-CD3 monoclonal antibodies." (1991) J. Immunol 147(9):3047-3052.
Hipp et al.,"A novel BCMA/CD3 bispecific T-cell engager for the treatment of multiple myeloma induces selective lysis in vitro and in vivo," (2017) Nature/Leukemia 31:1743-1751.
Anonymous, "Flow Cytometry Antibody: CD3e Cat. No. CT026-R301, SinoBiological Inc.,—Antibody—Catalogue,": (2017) Sinbiological, Inc. Retrieved from Internet: URL http://www.sinbiologica.com/flow-symmetry-antibody-elite.html.
Rossi et al., "Redirected T-cell Killing of Solid Cancers Targeted with an Anti-CD3/Trop-2-Bispecific Antibody is Enhanced in Combination with Interferon-g," 2014 Molecular Cancer Therapeutics 13(10):396-410.
Seckinger et al., "Target Expression, Generation, Preclinical Activity, and Pharmacokinetics of the BCMA-T Cell Bispecific Antibody EM801 for Multiple Myeloma Treatment," (2017) Cancer Cell, Cell Press US 31 (3):396-410.
Arnett et al., "Crystal Structure of a Human CD3-epsilon/delta Dimer in Complex with a UCHT1 Single-chain Antibody Fragment," (2004) Proc Natl Acad Sci USA 101 (46):16268-16273.
Gershoni et al., "Epitope Mapping—The First Step in Developing Epitope-based Vaccines," (2007) Biodrugs, Adis International, Ltd. NZ 21(3):145-526.
Merchant al., "An Efficient Route to Human Bispecific IgG," (1998) Nature Biotechnology, Gale Group, Inc. 16(7):677-681.
Bruggemann et al., "Human Antibody Production in Transgenic Animals," (2014) Archivum Immunologiae et Therapie Experimentalis, Birkahaeser Verlag AG 63(2):101-108.
Omniab, "Naturally Optimized Human Antibodies," (Feb. 23, 2016) retrieved from Internet: URL:http://content.stockpr.com/omniab/db/252/746/file/OmniAb.pdf.
Armitage, "A clinical evaluation of the International Lymphoma Study Group classification of non-Hodgkin's lymphoma," (1997) Blood 89(11):3909-3918.
Hanes et al., "New advances in microsphere-based single-dose vaccines," (1997) Advanced Drug Delivery Reviews 28(1):97-119.
Langer, "New Methods of Drug Delivery," (1990) Science 249(4976):1527-1533.
Labrijn et la., "Bispecific Antibodies: A Mechanistic Review of the Pipeline," (2019) Nature Reviews 18:585-608.

\* cited by examiner

FIG. 25

| expression ID | Format | % HMW | % Monomers | % LMW |
|---|---|---|---|---|
| 385171_394399_312325 | CD3, CD19 IgG4 BsAb P KiH | 0.10 | 99.9 | 0.0 |
| 385173_394256_312325 | CD3, CD19 IgG4 BsAb P | 2.33 | 97.7 | 0.0 |
| 318390_338683_312325 | CD3, CD19 IgG4 BsAb KiH PAA (TNB-486) | 0.05 | 99.9 | 0.07 |
| 316220_394259_312325 | CD3, CD19 IgG4 BsAb PAA | 2.09 | 97.9 | 0.0 |

MULTISPECIFIC HEAVY CHAIN ANTIBODIES WITH MODIFIED HEAVY CHAIN CONSTANT REGIONS

CROSS REFERENCE TO RELATED APPLICATIONS

This application claims priority benefit of the filing date of U.S. Provisional Patent Application Ser. No. 63/017,589, filed on Apr. 29, 2020, as well as U.S. Provisional Patent Application Ser. No. 63/108,796, filed on Nov. 2, 2020, the disclosures of which applications are incorporated by reference herein in their entireties. This application is a continuation of PCT/US2021/029909, filed on Apr. 29, 2021, the disclosure of which application is incorporated by reference herein in its entirety.

FIELD OF THE INVENTION

The present invention concerns multispecific, human heavy chain antibodies (e.g., UniAbs™) that have modified heavy chain constant regions that impart advantageous properties. The invention further concerns methods of making such antibodies, compositions, including pharmaceutical compositions, comprising such antibodies, and their use to treat disorders that are characterized by expression of one or more of the binding targets described herein.

BACKGROUND OF THE INVENTION

Modified Fc Regions

Advances in protein engineering have led to the successful manufacture and clinical utilization of multispecific antibodies having binding affinity to two or more targets. However, due to their heterodimeric nature, appropriate measures must be utilized to facilitate proper pairing of the desired combination of binding sequences, and thus the polypeptide subunits, in a multispecific antibody. Wang et al., *mAbs* 10:8, 1226-1235 (2018).

One approach to circumvent the problem of mispaired polypeptide subunits is known as "knobs-into-holes" (KiH), and it aims at forcing the pairing of two different antibody heavy chains by introducing mutations in the CH2 and/or CH3 domains to modify the contact interface. On one chain, bulky amino acids are replaced by amino acids with short side chains to create a "hole". Conversely, amino acids with large side chains are introduced into the other heavy chain to create a "knob". By co-expressing these two heavy chains, a higher yield of heterodimer formation ("knob-hole") versus homodimer formation ("hole-hole" or "knob-knob") is observed due to the more favorable stability of the knob-hole pair (Ridgway, J. B., et al, *Protein Eng.* 9 (1996) 617-621; and WO 96/027011).

While this strategy appears attractive for achieving a desired heterodimer, other properties of the resulting multispecific antibodies are highly dependent on the specific amino acid sequence of the Fc region, namely, effector functions, such as, e.g., complement-dependent cytotoxicity (CDC) and antibody dependent cellular cytotoxicity (ADCC). Additionally, effector function activity can induce the production of cytokines, which can lead to a "cytokine storm" of unwanted inflammatory responses. Gupta et al., *Journal of Interferon & Cytokine Research* 40:1, 19-23 (2019). Accordingly, in certain settings, there is a need to reduce or altogether eliminate effector functions, for example, to avoid impairing or killing an immune cell (e.g., a T-cell) to which a multispecific antibody binds, and/or to avoid unwanted cytokine production and the resulting undesirable inflammatory responses.

Furthermore, introducing amino acid modifications into a protein can have serious drawbacks, namely, inducing an immune response by the patient against the protein based on the presence of non-native sequences. As such, the development of multispecific antibodies requires identifying sequences that are very similar in general structure to those of naturally occurring antibodies (like IgA, IgD, IgE, IgG or IgM) with minimal deviation from native sequences, but that successfully incorporate modifications that can simultaneously achieve the goals of facilitating desired heterodimerization, while also achieving a reduction or elimination of one or more effector functions.

To balance these competing requirements, the inventors focused on IgG4 Fc, whose native sequence is known to have relatively low-level effector function activity. Crescioli et al., *Curr Allergy Asthma Rep* 16:7 (2016). However, despite this seeming advantage, IgG4 is known to undergo an in vivo chain exchange reaction due to its particular hinge region sequence, presenting additional complications for achieving desired heterodimerization. Labrijn et al., *Nature Biotechnology* 27, 767-71 (2009). As such, there is a need for modified heavy chain constant region sequences that achieve desired heterodimerization, incorporate modifications that reduce or eliminate effector functions, and at the same time incorporate modifications that reduce or eliminate chain exchange reactions in IgG4. The molecules described herein address these and other challenges.

Heavy Chain Antibodies

In a conventional IgG antibody, the association of the heavy chain and light chain is due in part to a hydrophobic interaction between the light chain constant region and the CH1 constant domain of the heavy chain. There are additional residues in the heavy chain framework 2 (FR2) and framework 4 (FR4) regions that also contribute to this hydrophobic interaction between the heavy and light chains.

It is known, however, that sera of camelids (sub-order Tylopoda which includes camels, dromedaries and llamas) contain a major type of antibodies composed solely of paired H-chains (heavy-chain only antibodies or UniAbs'). The UniAbs™ of Camelidae (*Camelus dromedarius, Camelus bactrianus, Lama glama, Lama guanaco, Lama alpaca* and *Lama vicugna*) have a unique structure consisting of a single variable domain (VHH), a hinge region and two constant domains (CH2 and CH3), which are highly homologous to the CH2 and CH3 domains of classical antibodies. These UniAbs™ lack the first domain of the constant region (CH1) which is present in the genome, but is spliced out during mRNA processing. The absence of the CH1 domain explains the absence of the light chain in the UniAbs™, since this domain is the anchoring place for the constant domain of the light chain. Such UniAbs™ naturally evolved to confer antigen-binding specificity and high affinity by three CDRs from conventional antibodies or fragments thereof (Muyldermans, 2001; *J Biotechnol* 74:277-302; Revets et al., 2005; *Expert Opin Biol Ther* 5:111-124). Cartilaginous fish, such as sharks, have also evolved a distinctive type of immunoglobulin, designated as IgNAR, which lacks the light polypeptide chains and is composed entirely by heavy chains. IgNAR molecules can be manipulated by molecular engineering to produce the variable domain of a single heavy chain polypeptide (vNARs) (Nuttall et al. *Eur. J. Biochem.* 270, 3543-3554 (2003); Nuttall et al. *Function and Bioinformatics* 55, 187-197 (2004); Dooley et al., *Molecular Immunology* 40, 25-33 (2003)).

The ability of heavy chain-only antibodies devoid of light chain to bind antigen was established in the 1960s (Jaton et al. (1968) *Biochemistry*, 7, 4185-4195). Heavy chain immunoglobulin physically separated from light chain retained 80% of antigen-binding activity relative to the tetrameric antibody. Sitia et al. (1990) *Cell*, 60, 781-790 demonstrated that removal of the CH1 domain from a rearranged mouse μ gene results in the production of a heavy chain-only antibody, devoid of light chain, in mammalian cell culture. The antibodies produced retained VH binding specificity and effector functions.

Heavy chain antibodies with a high specificity and affinity can be generated against a variety of antigens through immunization (van der Linden, R. H., et al. *Biochim. Biophys. Acta.* 1431, 37-46 (1999)) and the VHH portion can be readily cloned and expressed in yeast (Frenken, L. G. J., et al. *J. Biotechnol.* 78, 11-21 (2000)). Their levels of expression, solubility and stability are significantly higher than those of classical F(ab) or Fv fragments (Ghahroudi, M. A. et al. *FEBS Lett.* 414, 521-526 (1997)).

Mice in which the λ (lambda) light (L) chain locus and/or the λ and κ (kappa) L chain loci have been functionally silenced and antibodies produced by such mice are described in U.S. Pat. Nos. 7,541,513 and 8,367,888. Recombinant production of heavy chain-only antibodies in mice and rats has been reported, for example, in WO2006008548; U.S. Application Publication No. 20100122358; Nguyen et al., 2003, *Immunology*; 109(1), 93-101; Bruggemann et al., *Crit. Rev. Immunol.*; 2006, 26(5):377-90; and Zou et al., 2007, *J Exp Med*; 204(13): 3271-3283. The production of knockout rats via embryo microinjections of zinc-finger nucleases is described in Geurts et al., 2009, *Science*, 325(5939):433. Soluble heavy chain-only antibodies and transgenic rodents comprising a heterologous heavy chain locus producing such antibodies are described in U.S. Pat. Nos. 8,883,150 and 9,365,655. CAR-T structures comprising single-domain antibodies as binding (targeting) domain are described, for example, in Iri-Sofia et al., 2011, *Experimental Cell Research* 317:2630-2641 and Jamnani et al., 2014, *Biochim Biophys Acta*, 1840:378-386.

B-Cell Maturation Antigen (BCMA)

BCMA, also known as tumor necrosis factor superfamily member 17 (TNFRSF17) (UniProt Q02223), is a cell surface receptor exclusively expressed on plasma cells and plasmablasts. BCMA is a receptor for two ligands in the tumor necrosis factor (TNF) superfamily: APRIL (a proliferation-inducing ligand, also known as TNFSF13; TALL-2 and TRDL-1; the high affinity ligand for BCMA) and B-cell activation factor (BAFF) (also known as BLyS; TALL-1; THANK; zTNF4; TNFSF20; and D8Ertd387e; the low affinity ligand for BCMA). APRIL and BAFF are growth factors that bind BCMA and promote survival of plasma cells. BCMA is also highly expressed on malignant plasma cells in human multiple myeloma (MM). Antibodies binding to BCMA are described, for example, in Gras et al., 1995, Int. Immunol. 7:1093-1106, WO200124811 and WO200124812. Anti-BCMA antibodies that cross-react with TACI are described in WO2002/066516. Bispecific antibodies against BCMA and CD3 are described, for example, in US 2013/0156769 A1 and US 2015/0376287 A1. An anti-BCMA antibody-MMAE or -MMAF conjugate has been reported to selectively induce killing of multiple myeloma cells (Tai et al., Blood 2014, 123(20): 3128-38). Ali et al., Blood 2016, 128(13):1688-700, have reported that in a clinical trial (#NCT02215967) chimeric antigen receptor (CAR) T-cells targeting BCMA resulted in remission of multiple myeloma in human patients.

PSMA

PSMA, also known as Prostate Specific Membrane Antigen and Glutamate Carboxypeptidase II (UniProt Q04609), is a type II transmembrane protein that has N-acetylated-alpha-linked-acidic dipeptidase, folate hydrolase and dipeptidyl-peptidase activity. It is encoded by the FOLH1 gene in humans and consists of a 19 amino acid cytoplasmic domain, a 24 amino acid transmembrane portion, and a 707 amino acid extracellular portion. The protein is enzymatically active as a non-covalent homodimer. PSMA is expressed on prostate epithelium tissue and is upregulated in prostate cancer and the neovasculature of solid tumors. It is also expressed at low levels in healthy tissues such as the brain, kidney, and salivary glands, but its overexpression in malignant prostate tissue makes it an attractive target for the therapeutic treatment of prostate cancer. It may also be relevant for therapy or imaging of solid tumors, given its high expression in malignant neovasculature. Monoclonal antibodies, antibody-drug conjugates and chimeric antigen receptor T-cells targeting PSMA have been described for treatment of metastatic prostate cancer (Hernandez-Hoyos et al 2016, PMID: 27406985, DiPippo et al 2014, PMID: 25327986, Serganova et al 2016, PMID: 28345023). In addition, radionuclide conjugates specific to PSMA are being investigated for imaging and treatment of prostate cancer (e.g., Hofman et al., 2018 PMID: 29752180).

CD19

CD19, also known as B-Lymphocyte Surface Antigen B4 (UniProt P15391), is a cell surface receptor that is expressed on all human B-cells, but is not found on plasma cells. CD19 is a transmembrane protein that recruits cytoplasmic signaling proteins to the membrane and works within the CD19/CD21 complex to decrease the threshold for B-cell receptor signaling pathways. CD19 has a relatively large, 240 amino acid, cytoplasmic tail. The extracellular Ig-like domains are divided by a potential disulfide linked non-Ig-like domain and N-linked carbohydrate addition sites. The cytoplasmic tail contains at least nine tyrosine residues near the C-terminus, some of which have been shown to be phosphorylated. Along with CD20 and CD22, the restricted expression of CD19 to the B-cell lineage makes it an attractive target for the therapeutic treatment of B-cell malignancies. Many monoclonal antibodies and antibody drug conjugates specific to CD19 have been described (e.g., Naddafi et al. 2015, PMC4644525). In addition, anti-CD19 chimeric antigen receptor T-cells have been approved to treat leukemia (e.g., Sadelain et al. 2017, PMID: 29245005).

SUMMARY OF THE INVENTION

Aspects of the invention include isolated multispecific antibodies comprising: a first heavy chain polypeptide subunit comprising a mutated human IgG4 constant region comprising mutations S228P, F234A, L235A, and T366W; and a second heavy chain polypeptide subunit comprising a mutated human IgG4 constant region comprising mutations S228P, F234A, L235A, T366S, L368A, and Y407V. In some embodiments, the mutated human IgG4 constant region of the first heavy chain polypeptide subunit or the mutated human IgG4 constant region of second heavy chain polypeptide subunit lacks a CH1 domain. In some embodiments, the mutated human IgG4 constant region of the first heavy chain polypeptide subunit comprises a sequence of SEQ ID NO: 73 or 55, and the mutated human IgG4 constant region of the second heavy chain polypeptide subunit comprises a sequence of SEQ ID NO: 72 or 54.

In some embodiments, multispecific antibodies in accordance with embodiments of the invention further comprise a first binding moiety that has binding specificity for CD3, comprising: a heavy chain variable domain comprising a CDR1 sequence comprising a sequence of SEQ ID NO: 36, a CDR2 sequence comprising a sequence of SEQ ID NO: 37, and a CDR3 sequence comprising a sequence of SEQ ID NO: 38; and a light chain variable domain comprising a CDR1 sequence comprising a sequence of SEQ ID NO: 39, a CDR2 sequence comprising a sequence of SEQ ID NO: 40, and a CDR3 sequence comprising a sequence of SEQ ID NO: 41.

In some embodiments, the CDR1, CDR2 and CDR3 sequences in the heavy chain variable domain of the first binding moiety are present in a human VH framework; and the CDR1, CDR2 and CDR3 sequences in the light chain variable domain of the first binding moiety are present in a human Vkappa framework. In some embodiments, the heavy chain variable domain of the first binding moiety comprises a sequence having at least 95% identity to SEQ ID NO: 42; and the light chain variable domain of the first binding moiety comprises a sequence having at least 95% identity to SEQ ID NO: 43. In some embodiments, the heavy chain variable domain of the first binding moiety comprises the sequence of SEQ ID NO: 42; and the light chain variable domain of the first binding moiety comprises the sequence of SEQ ID NO: 43.

In some embodiments, multispecific antibodies in accordance with embodiments of the invention further comprise a second binding moiety having binding specificity to a protein other than CD3. In some embodiments, the second binding moiety comprises a single heavy chain variable region, in a monovalent or bivalent configuration. In some embodiments, the first binding moiety comprises a light chain polypeptide subunit and a heavy chain polypeptide subunit, and wherein the second binding moiety comprises a heavy chain polypeptide subunit. In some embodiments, the light chain polypeptide subunit of the first binding moiety comprises a light chain constant domain. In some embodiments, the protein other than CD3 is a tumor-associated antigen (TAA) or a tumor-specific antigen (TSA). In some embodiments, the TAA is B-cell maturation antigen (BCMA). In some embodiments, the TAA is CD19. In some embodiments, the TAA is prostate specific membrane antigen (PSMA).

Aspects of the invention include pharmaceutical compositions comprising a multispecific antibody as described herein, polynucleotides encoding a multispecific antibody as described herein, vectors comprising such polynucleotides, and cells comprising such vectors.

Aspects of the invention include methods of producing a multispecific antibody as described herein, comprising growing a cell as described herein under conditions permissive for expression of the multispecific antibody, and isolating the multispecific antibody from the cell.

Aspects of the invention include methods of treatment comprising administering to an individual in need an effective dose of a multispecific antibody, or the pharmaceutical composition, described herein.

Aspects of the invention include use of a multispecific antibody described herein in the preparation of a medicament for the treatment of a disease or disorder in an individual in need.

Aspects of the invention include methods for treating a disease or condition characterized by expression of BCMA, comprising administering to an individual in need an effective dose of a multispecific antibody, or a pharmaceutical composition, described herein. In some embodiments, the disease is an autoimmune disease. In some embodiments, the disease is a cancer. In some embodiments, the cancer is a myeloma. In some embodiments, the myeloma is multiple myeloma.

Aspects of the invention include methods for treating a disease or condition characterized by expression of PSMA, comprising administering to an individual in need an effective dose of a multispecific antibody, or a pharmaceutical composition, described herein. In some embodiments, the disease is a cancer. In some embodiments, the cancer is prostate cancer.

Aspects of the invention include methods for treating a disease or condition characterized by expression of CD19, comprising administering to an individual in need an effective dose of a multispecific antibody, or a pharmaceutical composition, described herein. In some embodiments, the disorder is diffuse large B-cell lymphoma (DLBCL). In some embodiments, the disorder is acute lymphoblastic leukemia (ALL). In some embodiments, the disorder is non-Hodgkin's lymphoma (NHL). In some embodiments, the disorder is systemic lupus erythematosus (SLE). In some embodiments, the disorder is rheumatoid arthritis (RA). In some embodiments, the disorder is multiple sclerosis (MS).

Aspects of the invention include kits for treating a disease or disorder in an individual in need, comprising a multispecific antibody, or a pharmaceutical composition, described herein, and instructions for use. In some embodiments, a kit further comprises at least one additional reagent. In some embodiments, the at least one additional reagent comprises a chemotherapeutic drug.

Aspects of the invention include bispecific three-chain antibody like molecules comprising: a first polypeptide subunit comprising: a light chain variable domain (VL) comprising a sequence of SEQ ID NO: 43; and a light chain constant domain (CL); a second polypeptide subunit comprising: a heavy chain variable domain (VH) comprising a sequence of SEQ ID NO: 42; and a heavy chain constant domain (CH) comprising a sequence of SEQ ID NO: 72 or 73; wherein the light chain variable domain and the heavy chain variable domain together form a first binding moiety that has binding specificity for CD3; and a third polypeptide subunit comprising: a heavy chain-only variable region, in a monovalent or bivalent configuration, that has binding specificity for a protein other than CD3; and a heavy chain constant domain (CH) comprising a sequence of SEQ ID NO: 54 or 55. In some embodiments, the third polypeptide subunit comprises a heavy chain-only variable region in a bivalent configuration that has binding specificity to BCMA.

Aspects of the invention include bispecific three-chain antibody like molecules comprising: a first polypeptide subunit comprising a sequence of SEQ ID NO: 49; a second polypeptide subunit comprising a sequence of SEQ ID NO: 56; and a third polypeptide subunit comprising a sequence of SEQ ID NO: 58.

Aspects of the invention include pharmaceutical compositions comprising a bispecific three-chain antibody like molecule described herein, polynucleotides encoding a bispecific three-chain antibody like molecule described herein, vectors comprising such polynucleotides, and cells comprising such vectors.

Aspects of the invention include methods of producing a bispecific three-chain antibody like molecule described herein, comprising growing a cell described herein under conditions permissive for expression of the bispecific three-chain antibody like molecule, and isolating the bispecific three-chain antibody like molecule from the cell.

Aspects of the invention include methods of treatment, comprising administering to an individual in need an effective dose of a bispecific three-chain antibody like molecule, or a pharmaceutical composition, described herein.

Aspects of the invention include use of a bispecific three-chain antibody like molecule described herein in the preparation of a medicament for the treatment of a disease or disorder in an individual in need.

Aspects of the invention include methods for treating a disease or condition characterized by expression of BCMA, comprising administering to an individual in need an effective dose of a bispecific three-chain antibody like molecule, or a pharmaceutical composition, described herein. In some embodiments, the disease is an autoimmune disease. In some embodiments, the disease is a cancer. In some embodiments, the cancer is a myeloma. In some embodiments, the myeloma is multiple myeloma.

Aspects of the invention include kits for treating a disease or disorder in an individual in need, comprising a bispecific three-chain antibody like molecule, or a pharmaceutical composition, described herein, and instructions for use. In some embodiments, a kit further comprises at least one additional reagent. In some embodiments, the at least one additional reagent comprises a chemotherapeutic drug.

These and further aspects will be further explained in the rest of the disclosure, including the Examples.

BRIEF DESCRIPTION OF THE DRAWINGS

FIG. 8, panel B is a graph showing cell binding to cynomolgus monkey PSMA.

FIG. 25 is a table showing % HMW species, % Monomers, and % LMW species from samples of the indicated constructs following purification.

DETAILED DESCRIPTION OF THE PREFERRED EMBODIMENTS

Figure 1:
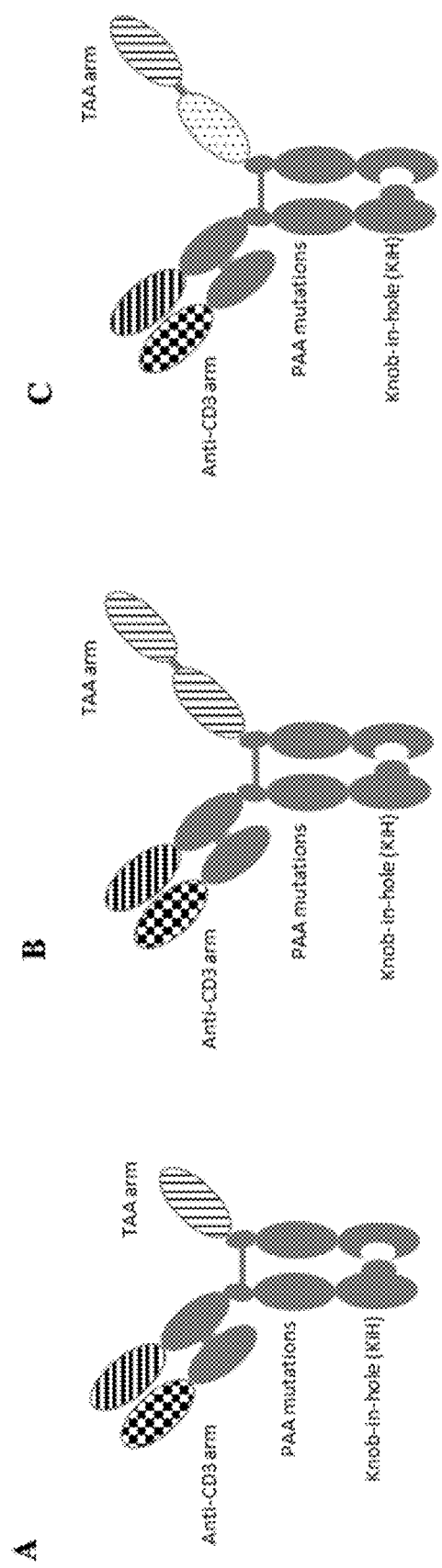
FIG. 1, panels A-C, provide illustrations of various multispecific antibodies in accordance with embodiments of the invention.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless indicated otherwise, antibody residues herein are numbered according to the Kabat numbering system (e.g., Kabat et al., Sequences of Immunological Interest. 5th Ed. Public Health Service, National Institutes of Health, Bethesda, Md. (1991)).

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All references cited throughout the disclosure, including patent applications and publications, are incorporated by reference herein in their entirety.

I. Definitions

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

Antibody residues herein are numbered according to the Kabat numbering system and the EU numbering system. The Kabat numbering system is generally used when referring to a residue in the variable domain (approximately residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies mean residue numbering by the Kabat numbering system. Unless stated otherwise herein, references to residue numbers in the constant domain of antibodies mean residue numbering by the EU numbering system.

An "antibody" or "immunoglobulin" refers to a molecule comprising at least one heavy chain and one light chain, where the amino terminal domain of the heavy and light chains is variable in sequence, hence is commonly referred to as a variable region domain, or a variable heavy (VH) or variable light (VH) domain. The two domains conventionally associate to form a specific binding region, although as will be discussed here, specific binding can also be obtained with heavy chain-only variable sequences, and a variety of non-natural configurations of antibodies are known and used in the art.

A "functional" or "biologically active" antibody or antigen-binding molecule (including heavy chain-only antibodies and multi-specific (e.g., bispecific) three-chain antibody-like molecules (TCAs), described herein) is one capable of exerting one or more of its natural activities in structural, regulatory, biochemical or biophysical events. For example, a functional antibody or other binding molecule, e.g., a TCA, may have the ability to specifically bind an antigen and the binding may in turn elicit or alter a cellular or molecular event such as signal transduction or enzymatic activity. A functional antibody or other binding molecule, e.g., a TCA, may also block ligand activation of a receptor or act as an agonist or antagonist. The capability of an antibody or other binding molecule, e.g., a TCA, to exert one or more of its natural activities depends on several factors, including proper folding and assembly of the polypeptide chains.

The term antibody may reference a full-length heavy chain, a full length light chain, an intact immunoglobulin molecule; or an immunologically active portion of any of these polypeptides, i.e., a polypeptide that comprises an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule, including engineered subclasses with altered Fc portions that provide for reduced or enhanced effector cell activity. Light chains of the subject antibodies can be kappa light chains (Vkappa) or lambda light chains (Vlambda). The immunoglobulins can be derived from any species. In one aspect, the immunoglobulin is of largely human origin.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies in accordance with the present invention can be made by the hybridoma method first described by Kohler et al. (1975) *Nature* 256:495, and can also be made via recombinant protein production methods (see, e.g., U.S. Pat. No. 4,816,567), for example.

The term "variable", as used in connection with antibodies, refers to the fact that certain portions of the antibody variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" residues 26-32 (H1), 53-55 (H2) and 96-101 (H3) in the heavy chain variable domain; Chothia and Lesk *J. Mol. Biol.* 196:901-917 (1987)). In some embodiments, "CDR" means a complementary determining region of an antibody as defined in Lefranc, M P et al., IMGT, the international ImMunoGeneTics database, Nucleic Acids Res., 27:209-212 (1999). "Framework Region" or "FR" residues are those variable domain residues other than the hypervariable region/CDR residues as herein defined.

Exemplary CDR designations are shown herein, however one of skill in the art will understand that a number of definitions of the CDRs are commonly in use, including the Kabat definition (see "Zhao et al. A germline knowledge based computational approach for determining antibody complementarity determining regions." *Mol Immunol*. 2010; 47:694-700), which is based on sequence variability and is the most commonly used. The Chothia definition is based on the location of the structural loop regions (Chothia et al. "Conformations of immunoglobulin hypervariable regions." *Nature*. 1989; 342:877-883). Alternative CDR definitions of interest include, without limitation, those disclosed by Honegger, "Yet another numbering scheme for immunoglobulin variable domains: an automatic modeling and analysis tool." *J Mol Biol*. 2001; 309:657-670; Ofran et al. "Automated identification of complementarity determining regions (CDRs) reveals peculiar characteristics of CDRs and B-cell epitopes." *J Immunol*. 2008; 181:6230-6235; Almagro "Identification of differences in the specificity-determining residues of antibodies that recognize antigens of different size: implications for the rational design of antibody repertoires." *J Mol Recognit*. 2004; 17:132-143; and Padlan et al. "Identification of specificity-determining residues in antibodies." *Faseb J*. 1995; 9:133-139, each of which is herein specifically incorporated by reference.

The terms "heavy chain-only antibody," and "heavy chain antibody" are used interchangeably herein and refer, in the broadest sense, to antibodies, or one or more portions of an antibody, e.g., one or more arms of an antibody, lacking the light chain of a conventional antibody. The terms specifically include, without limitation, homodimeric antibodies comprising the VH antigen-binding domain and the CH2 and CH3 constant domains, in the absence of the CH1 domain; functional (antigen-binding) variants of such antibodies, soluble VH variants, Ig-NAR comprising a homodimer of one variable domain (V-NAR) and five C-like constant domains (C-NAR) and functional fragments thereof; and soluble single domain antibodies (sUniDabs™). In one embodiment, a heavy chain-only antibody is composed of a variable region antigen-binding domain composed of framework 1, CDR1, framework 2, CDR2, framework 3, CDR3, and framework 4. In another embodiment, a heavy chain-only antibody is composed of an antigen-binding domain, at least part of a hinge region and CH2 and CH3 domains. In another embodiment, a heavy chain-only antibody is composed of an antigen-binding domain, at least part of a hinge region and a CH2 domain. In a further embodiment, a heavy chain-only antibody is composed of an antigen-binding domain, at least part of a hinge region and a CH3 domain Heavy chain-only antibodies in which the CH2 and/or CH3 domain is truncated are also included herein. In a further embodiment, a heavy chain is composed of an antigen binding domain, and at least one CH (CH1, CH2, CH3, or CH4) domain but no hinge region. The heavy chain-only antibody can be in the form of a dimer, in which two heavy chains are disulfide bonded or otherwise, covalently or non-covalently, attached with each other. The heavy chain-only antibody may belong to the IgG subclass, but antibodies belonging to other subclasses, such as IgM, IgA, IgD and IgE subclass, are also included herein. In a particular embodiment, a heavy chain antibody is of the IgG1, IgG2, IgG3, or IgG4 subtype, in particular the IgG1 subtype. In one embodiment, the heavy chain-only antibodies herein are used as a binding (targeting) domain of a chimeric antigen receptor (CAR). The definition specifically includes human heavy chain-only antibodies produced by human immunoglobulin transgenic rats (UniRat™), called UniAbs™. The variable regions (VH) of UniAbs™ are called UniDabs™, and are versatile building blocks that can be linked to Fc regions or serum albumin for the development of novel therapeutics with multi-specificity, increased potency and extended half-life. Since the homodimeric UniAbs™ lack a light chain and thus a VL domain, the antigen is recognized by one single domain, i.e., the variable domain of the heavy chain of a heavy-chain antibody (VH or VHH).

An "intact antibody chain" as used herein is one comprising a full length variable region and a full length constant region (Fc). An intact "conventional" antibody comprises an intact light chain and an intact heavy chain, as well as a light chain constant domain (CL) and heavy chain constant domains, CH1, hinge, CH2 and CH3 for secreted IgG. Other isotypes, such as IgM or IgA may have different CH domains. The constant domains may be native sequence constant domains (e.g., human native sequence constant domains) or amino acid sequence variants thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors. Constant region variants include those that alter the effector profile, binding to Fc receptors, and the like.

Depending on the amino acid sequence of the Fc (constant domain) of their heavy chains, antibodies and various antigen-binding proteins can be provided as different classes. There are five major classes of heavy chain Fc regions: IgA, IgD, IgE, IgG, and IgM, and several of these may be further divided into "subclasses" (isotypes), e.g., IgG1, IgG2, IgG3, IgG4, IgA, and IgA2. The Fc constant domains that correspond to the different classes of antibodies may be referenced as α, δ, ε, γ, and μ, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267:7246-7256; US 2005/0048572; US 2004/0229310). The light chains of antibodies from any vertebrate species can be assigned to one of two types, called κ (kappa) and λ (lambda), based on the amino acid sequences of their constant domains. Antibodies in accordance with embodiments of the invention can comprise kappa light chain sequences or lambda light chain sequences.

A "functional Fc region" possesses an "effector function" of a native-sequence Fc region. Non-limiting examples of effector functions include C1q binding; CDC; Fc-receptor binding; ADCC; ADCP; down-regulation of cell-surface receptors (e.g., B-cell receptor), etc. Such effector functions generally require the Fc region to interact with a receptor, e.g., the FcγRI; FcγRIIA; FcγRIIB1; FcγRIIB2; FcγRIIIA; FcγRIIIB receptors, and the low affinity FcRn receptor; and can be assessed using various assays known in the art. A "dead" or "silenced" Fc is one that has been mutated to retain activity with respect to, for example, prolonging serum half-life, but which does not activate a high affinity Fc receptor, or which has a reduced affinity to an Fc receptor.

A "native-sequence Fc region" comprises an amino acid sequence identical to the amino acid sequence of an Fc region found in nature. Native-sequence human Fc regions include, for example, a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, such as 1, 2, 3, 4, 5, 6, 7, 8, 9 or 10 amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

The human IgG4 Fc amino acid sequence (UniProtKB No. P01861) is provided herein as SEQ ID NO: 45. Silenced IgG1 is described, for example, in Boesch, A. W., et al., "Highly parallel characterization of IgG Fc binding interactions." MAbs, 2014. 6(4): p. 915-27, the disclosure of which is incorporated herein by reference in its entirety.

Other Fc variants are possible, including, without limitation, one in which a region capable of forming a disulfide bond is deleted, or in which certain amino acid residues are eliminated at the N-terminal end of a native Fc, or a methionine residue is added thereto. Thus, in some embodiments, one or more Fc portions of an antibody can comprise one or more mutations in the hinge region to eliminate disulfide bonding. In yet another embodiment, the hinge region of an Fc can be removed entirely. In still another embodiment, an antibody can comprise an Fc variant.

Further, an Fc variant can be constructed to remove or substantially reduce effector functions by substituting (mutating), deleting or adding amino acid residues to effect complement binding or Fc receptor binding. For example, and not limitation, a deletion may occur in a complement-binding site, such as a C1q-binding site. Techniques for preparing such sequence derivatives of the immunoglobulin Fc fragment are disclosed in International Patent Publication Nos. WO 97/34631 and WO 96/32478. In addition, the Fc domain may be modified by phosphorylation, sulfation, acylation, glycosylation, methylation, farnesylation, acetylation, amidation, and the like.

In some embodiments, an antibody comprises a variant human IgG4 CH3 domain sequence comprising a T366W mutation, which can optionally be referred to herein as an IgG4 CH3 knob sequence. In some embodiments, an antibody comprises a variant human IgG4 CH3 domain sequence comprising a T366S mutation, an L368A mutation, and a Y407V mutation, which can optionally be referred to herein as an IgG4 CH3 hole sequence. The IgG4 CH3 mutations described herein can be utilized in any suitable manner so as to place a "knob" on a first heavy chain constant region of a first monomer in an antibody dimer, and a "hole" on a second heavy chain constant region of a second monomer in an antibody dimer, thereby facilitating proper pairing (heterodimerization) of the desired pair of heavy chain polypeptide subunits in the antibody.

In some embodiments, an antibody comprises a heavy chain polypeptide subunit comprising a variant human IgG4 Fc region comprising an S228P mutation, an F234A mutation, an L235A mutation, and a T366W mutation (knob). In some embodiments, and antibody comprises a heavy chain polypeptide subunit comprising a variant human IgG4 Fc region comprising an S228P mutation, an F234A mutation, an L235A mutation, a T366S mutation, an L368A mutation, and a Y407V mutation (hole).

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, an antibody having an Fc region according to this invention can comprise an antibody with or without K447.

Aspects of the invention include antibodies comprising a heavy chain-only variable region in a monovalent or bivalent configuration. As used herein, the term "monovalent configuration" as used in reference to a heavy chain-only variable region domain means that only one heavy chain-only variable region domain is present, having a single binding site (see FIG. 1, Panel A, right arm of antibody). In contrast, the term "bivalent configuration" as used in reference to a heavy chain-only variable region domain means that two heavy chain-only variable region domains are present (each having a single binding site), and are connected by a linker sequence (see FIG. 1, Panels B and C, right arms of antibodies). Non-limiting examples of linker sequences are discussed further herein, and include, without limitation, GS linker sequences of various lengths. When a heavy chain-only variable region is in a bivalent configuration, each of the two heavy chain-only variable region domains can have binding affinity to the same antigen, or to different antigens (e.g., to different epitopes on the same protein; to two different proteins, etc.). However, unless specifically noted otherwise, a heavy chain-only variable region denoted as being in a "bivalent configuration" is understood to contain two identical heavy chain-only variable region domains, connected by a linker sequence, wherein each of the two identical heavy chain-only variable region domains have binding affinity to the same target antigen.

Aspects of the invention include antibodies having multi-specific configurations, which include, without limitation, bispecific, trispecific, etc. A large variety of methods and protein configurations are known and used in bispecific monoclonal antibodies (BsMAB), tri-specific antibodies, etc.

Various methods for the production of multivalent artificial antibodies have been developed by recombinantly fusing variable domains of two or more antibodies. In some embodiments, a first and a second antigen-binding domain on a polypeptide are connected by a polypeptide linker. One non-limiting example of such a polypeptide linker is a GS linker, having an amino acid sequence of four glycine residues, followed by one serine residue, and wherein the sequence is repeated n times, where n is an integer ranging from 1 to about 10, such as 2, 3, 4, 5, 6, 7, 8, or 9. Non-limiting examples of such linkers include GGGGS (SEQ ID NO: 70) (n=1) and GGGGSGGGGS (SEQ ID NO: 71) (n=2). Other suitable linkers can also be used, and are described, for example, in Chen et al., Adv Drug Deliv Rev. 2013 Oct. 15; 65(10): 1357-69, the disclosure of which is incorporated herein by reference in its entirety.

The term "three-chain antibody like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy-chain only antibody comprising an Fc portion comprising CH2 and/or CH3 and/or CH4 domains, in the absence of a CH1 domain, and one or more antigen binding domains (e.g., two antigen binding domains) that binds an epitope of a second antigen or a different epitope of the first antigen, where such binding domain is derived from or has sequence identity with the variable region of an antibody heavy or light chain. Parts of such variable region may be encoded by $V_H$ and/or $V_L$ gene segments, D and $J_H$ gene segments, or $J_L$ gene segments. The variable region may be encoded by rearranged $V_H DJ_H$, $V_L DJ_H$, $V_H J_L$, or $V_L J_L$ gene segments.

A TCA binding compound makes use of a "heavy chain only antibody" or "heavy chain antibody" or "heavy chain polypeptide" which, as used herein, mean a single chain antibody comprising heavy chain constant regions CH2 and/or CH3 and/or CH4 but no CH1 domain. In one embodiment, the heavy chain antibody is composed of an antigen-binding domain, at least part of a hinge region and CH2 and CH3 domains. In another embodiment, the heavy chain antibody is composed of an antigen-binding domain, at least part of a hinge region and a CH2 domain. In a further embodiment, the heavy chain antibody is composed of an antigen-binding domain, at least part of a hinge region and a CH3 domain Heavy chain antibodies in which the CH2 and/or CH3 domain is truncated are also included herein. In a further embodiment, the heavy chain is composed of an antigen binding domain, and at least one CH (CH1, CH2, CH3, or CH4) domain but no hinge region. The heavy chain only antibody can be in the form of a dimer, in which two heavy chains are disulfide bonded other otherwise covalently or non-covalently attached to each other, and can optionally include an asymmetric interface between one or more of the CH domains to facilitate proper pairing between polypeptide chains. The heavy-chain antibody may belong to the IgG subclass, but antibodies belonging to other subclasses, such as IgM, IgA, IgD and IgE subclass, are also included herein. In a particular embodiment, the heavy chain antibody is of the IgG1, IgG2, IgG3, or IgG4 subtype, in particular the IgG1 subtype or the IgG4 subtype. Non-limiting examples of a TCA binding compound are described in, for example, WO2017/223111 and WO2018/052503, the disclosures of which are incorporated herein by reference in their entirety.

Heavy-chain antibodies constitute about one fourth of the IgG antibodies produced by the camelids, e.g., camels and llamas (Hamers-Casterman C., et al. Nature. 363, 446-448 (1993)). These antibodies are formed by two heavy chains but are devoid of light chains. As a consequence, the variable antigen binding part is referred to as the VHH domain and it represents the smallest naturally occurring, intact, antigen-binding site, being only around 120 amino acids in length (Desmyter, A., et al. J. Biol. Chem. 276, 26285-26290 (2001)). Heavy chain antibodies with a high specificity and affinity can be generated against a variety of antigens through immunization (van der Linden, R. H., et al. Biochim. Biophys. Acta. 1431, 37-46 (1999)) and the VHH portion can be readily cloned and expressed in yeast (Frenken, L. G. J., et al. J. Biotechnol. 78, 11-21 (2000)). Their levels of expression, solubility and stability are significantly higher than those of classical F(ab) or Fv fragments (Ghahroudi, M. A. et al. FEBS Lett. 414, 521-526 (1997)). Sharks have also been shown to have a single VH-like domain in their antibodies, termed VNAR. (Nuttall et al. Eur. J. Biochem. 270, 3543-3554 (2003); Nuttall et al. Function and Bioinformatics 55, 187-197 (2004); Dooley et al., Molecular Immunology 40, 25-33 (2003)).

The term "CD3" refers to the human CD3 protein multi-subunit complex. The CD3 protein multi-subunit complex is composed to 6 distinctive polypeptide chains. These include a CD3γ chain (SwissProt P09693), a CD3δ chain (SwissProtP04234), two CD3ε chains (SwissProt P07766), and one CD3ζ chain homodimer (SwissProt 20963), and which is associated with the T-cell receptor α and β chain. The term "CD3" includes any CD3 variant, isoform and species homolog which is naturally expressed by cells (including T-cells) or can be expressed on cells transfected with genes or cDNA encoding those polypeptides, unless noted.

A "BCMA×CD3 antibody" is a multispecific heavy chain-only antibody, such as a bispecific heavy chain-only antibody, which comprises two different antigen-binding regions, one of which binds specifically to the antigen BCMA and one of which binds specifically to CD3. A "PSMA×CD3 antibody" is a multispecific heavy chain-only antibody, such as a bispecific heavy chain-only antibody, which comprises two different antigen-binding regions, one of which binds specifically to the antigen PSMA and one of which binds specifically to CD3. A "CD19× CD3 antibody" is a multispecific heavy chain-only antibody, such as a bispecific heavy chain-only antibody, which comprises two different antigen-binding regions, one of which binds specifically to the antigen CD19 and one of which binds specifically to CD3.

The term "BCMA" as used herein relates to human B-cell maturation antigen, also known as BCMA, CD269, and TNFRSF17 (UniProt Q02223), which is a member of the tumor necrosis receptor superfamily that is preferentially expressed in differentiated plasma cells. The extracellular domain of human BCMA consists, according to UniProt of amino acids 1-54 (or 5-51).

The term "anti-BCMA heavy chain-only antibody," and "BCMA heavy chain-only antibody" are used herein to refer to a heavy chain-only antibody as hereinabove defined, immunospecifically binding to BCMA.

The term "PSMA" as used herein refers to a type II transmembrane protein that has N-acetylated-alpha-linked acidic depeptidase, folate hydrolase and dipeptidyl-peptidase activity. The term "PSMA" includes a PSMA protein of any human and non-human animal species, and specifically includes human PSMA as well as PSMA of non-human mammals.

The term "human PSMA" as used herein includes any variants, isoforms and species homologs of human PSMA (UniProt Q04609), regardless of its source or mode of preparation. Thus, "human PSMA" includes human PSMA naturally expressed by cells and PSMA expressed on cells transfected with the human PSMA gene.

The terms "anti-PSMA heavy chain-only antibody," "PSMA heavy chain-only antibody," "anti-PSMA heavy chain antibody" and "PSMA heavy chain antibody" are used herein interchangeably to refer to a heavy chain-only antibody as hereinabove defined, immunospecifically binding to PSMA, including human PSMA, as hereinabove defined. The definition includes, without limitation, human heavy chain antibodies produced by transgenic animals, such as transgenic rats or transgenic mice expressing human immunoglobulin, including UniRats™ producing human anti-PSMA UniAb™ antibodies, as hereinabove defined.

The terms "CD19" and "cluster of differentiation 19" as used herein refer to a molecule expressed during all phases of B-cell development until terminal differentiation into plasma cells. The term "CD19" includes a CD19 protein of any human and non-human animal species, and specifically includes human CD19 as well as CD19 of non-human mammals.

The term "human CD19" as used herein includes any variants, isoforms and species homologs of human CD19 (UniProt P15391), regardless of its source or mode of preparation. Thus, "human CD19" includes human CD19 naturally expressed by cells and CD19 expressed on cells transfected with the human CD19 gene.

The terms "anti-CD19 heavy chain-only antibody," "CD19 heavy chain-only antibody," "anti-CD19 heavy chain antibody" and "CD19 heavy chain antibody" are used herein interchangeably to refer to a heavy chain-only antibody as hereinabove defined, immunospecifically binding to CD19, including human CD19, as hereinabove defined. The definition includes, without limitation, human heavy chain antibodies produced by transgenic animals, such as transgenic rats or transgenic mice expressing human immunoglobulin, including UniRats™ producing human anti-CD19 UniAb™ antibodies, as hereinabove defined.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antibodies of the invention include multi-specific antibodies. Multi-specific antibodies have more than one binding specificity. The term "multi-specific" specifically includes "bispecific" and "trispecific," as well as higher-order independent specific binding affinities, such as higher-order polyepitopic specificity, as well as tetravalent antibodies and antibody fragments. The terms "multi-specific antibody," "multi-specific heavy chain-only antibody," "multi-specific heavy chain antibody," and "multi-specific UniAb™" are used herein in the broadest sense and cover all antibodies with more than one binding specificity.

The multi-specific antibodies of the present invention specifically include antibodies immunospecifically binding to two or more non-overlapping epitopes on a BCMA protein, a PSMA protein, or a CD19 protein, such as a human BCMA protein, a human PSMA protein, or a human CD19 protein (i.e., bivalent and biparatopic). The multi-specific heavy chain antibodies of the present invention also specifically include antibodies immunospecifically binding to an epitope on a BCMA protein, a PSMA protein, or a CD19 protein, such as a human BCMA protein, a human PSMA protein, or a human CD19 protein and to an epitope on a different protein, such as, for example, a CD3 protein, such as human CD3 (i.e., bivalent and biparatopic). The multi-specific heavy chain antibodies of the present invention also specifically include antibodies immunospecifically binding to two or more non-overlapping or partially overlapping epitopes on a BCMA protein, a PSMA protein, or a CD19 protein, such as a human BCMA protein, a human PSMA protein, or a human CD19 protein, and to an epitope on a different protein, such as, for example, a CD3 protein, such as human CD3 protein (i.e., trivalent and biparatopic).

An "epitope" is the site on the surface of an antigen molecule to which a single antibody molecule binds. Generally an antigen has several or many different epitopes and reacts with many different antibodies. The term specifically includes linear epitopes and conformational epitopes.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Polyepitopic specificity" refers to the ability to specifically bind to two or more different epitopes on the same or different target(s). As noted above, the present invention specifically includes heavy chain antibodies with polyepitopic specificities, i.e., heavy chain antibodies binding to one or more non-overlapping epitopes on a BCMA protein, a PSMA protein, or a CD19 protein, such as a human BCMA protein, a human PSMA protein, or a human CD19 protein; and heavy chain antibodies binding to one or more epitopes on a BCMA protein, a PSMA protein, or a CD19 protein, and to an epitope on a different protein, such as, for example, a CD3 protein. The term "non-overlapping epitope(s)" or "non-competitive epitope(s)" of an antigen is defined herein to mean epitope(s) that are recognized by one member of a pair of antigen-specific antibodies but not the other member. Pairs of antibodies, or antigen-binding regions targeting the same antigen on a multi-specific antibody, recognizing non-overlapping epitopes, do not compete for binding to that antigen and are able to bind that antigen simultaneously.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The term "valent" as used herein refers to a specified number of binding sites in an antibody molecule.

A "monovalent" antibody has one binding site. Thus a monovalent antibody is also monospecific.

A "multi-valent" antibody has two or more binding sites. Thus, the terms "bivalent", "trivalent", and "tetravalent" refer to the presence of two binding sites, three binding sites, and four binding sites, respectively. Thus, a bispecific antibody according to the invention is at least bivalent and may be trivalent, tetravalent, or otherwise multi-valent. A bivalent antibody in accordance with embodiments of the invention may have two binding sites to the same epitope (i.e., bivalent, monoparatopic), or to two different epitopes (i.e., bivalent, biparatopic).

A large variety of methods and protein configurations are known and used for the preparation of bispecific monoclonal antibodies (BsMAB), tri-specific antibodies, and the like.

The term "three-chain antibody like molecule" or "TCA" is used herein to refer to antibody-like molecules comprising, consisting essentially of, or consisting of three polypeptide subunits, two of which comprise, consist essentially of, or consist of one heavy chain and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy chain-only antibody comprising an Fc portion comprising CH2 and/or CH3 and/or CH4 domains, in the absence of a CH1 domain, and an antigen binding domain that binds an epitope of a second antigen or a different epitope of the first antigen, where such binding domain is derived from or has sequence identity with the variable region of an antibody heavy or light chain.

Parts of such variable region may be encoded by $V_H$ and/or $V_L$ gene segments, D and $J_H$ gene segments, or $J_L$ gene segments. The variable region may be encoded by rearranged $V_H DJ_H$, $V_L DJ_H$, $V_H J_L$, or $V_L J_L$ gene segments. A TCA protein makes use of a heavy chain-only antibody as hereinabove defined.

The term "chimeric antigen receptor" or "CAR" is used herein in the broadest sense to refer to an engineered receptor, which grafts a desired binding specificity (e.g., the antigen-binding region of a monoclonal antibody or other ligand) to membrane-spanning and intracellular-signaling domains. Typically, the receptor is used to graft the specificity of a monoclonal antibody onto a T-cell to create a chimeric antigen receptors (CAR). (*J Natl Cancer Inst*, 2015; 108(7):dvj439; and Jackson et al., *Nature Reviews Clinical Oncology*, 2016; 13:370-383). CAR-T cells are T-cells that have been genetically engineered to produce an artificial T-cell receptor for use in immunotherapy. In one embodiment, "CAR-T cell" means a therapeutic T-cell expressing a transgene encoding one or more chimeric antigen receptors comprised minimally of an extracellular domain, a transmembrane domain, and at least one cytosolic domain The term "human antibody" is used herein to include antibodies having variable and constant regions derived from human germline immunoglobulin sequences. The human antibodies herein may include amino acid residues not encoded by human germline immunoglobulin sequences, e.g., mutations introduced by random or site-specific mutagenesis in vitro or by somatic mutation in vivo. The term "human antibody" specifically includes heavy chain-only antibodies having human heavy chain variable region sequences, produced by transgenic animals, such as transgenic rats or mice, in particular UniAbs™ produced by UniRats™, as defined above.

By a "chimeric antibody" or a "chimeric immunoglobulin" is meant an immunoglobulin molecule comprising amino acid sequences from at least two different Ig loci, e.g., a transgenic antibody comprising a portion encoded by a human Ig locus and a portion encoded by a rat Ig locus. Chimeric antibodies include transgenic antibodies with non-human Fc-regions or artificial Fc-regions, and human idiotypes. Such immunoglobulins can be isolated from animals of the invention that have been engineered to produce such chimeric antibodies.

As used herein, the term "effector cell" refers to an immune cell which is involved in the effector phase of an immune response, as opposed to the cognitive and activation phases of an immune response. Some effector cells express specific Fc receptors and carry out specific immune functions. In some embodiments, an effector cell such as a natural killer cell is capable of inducing antibody-dependent cellular cytotoxicity (ADCC). For example, monocytes and-macrophages, which express FcR, are involved in specific killing of target cells and presenting antigens to other components of the immune system, or binding to cells that present antigens. In some embodiments, an effector cell may phagocytose a target antigen or target cell.

"Human effector cells" are leukocytes which express receptors such as T-cell receptors or FcRs and perform effector functions. Preferably, the cells express at least FcγRIII and perform ADCC effector function. Examples of human leukocytes which mediate ADCC include natural killer (NK) cells, monocytes, cytotoxic T-cells and neutrophils; with NK cells being preferred. The effector cells may be isolated from a native source thereof, e.g., from blood or PBMCs as described herein.

The term "immune cell" is used herein in the broadest sense, including, without limitation, cells of myeloid or lymphoid origin, for instance lymphocytes (such as B-cells and T-cells including cytolytic T-cells (CTLs)), killer cells, natural killer (NK) cells, macrophages, monocytes, eosinophils, polymorphonuclear cells, such as neutrophils, granulocytes, mast cells, and basophils.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity (CDC); Fc receptor binding; antibody-dependent cell-mediated cytotoxicity (ADCC); phagocytosis; down regulation of cell surface receptors (e.g., B-cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (USA) 95:652-656 (1998).

"Complement dependent cytotoxicity" or "CDC" refers to the ability of a molecule to lyse a target in the presence of complement. The complement activation pathway is initiated by the binding of the first component of the complement system (C1 q) to a molecule (e.g. an antibody) complexed with a cognate antigen. To assess complement activation, a CDC assay, e.g., as described in Gazzano-Santoro et al., *J. Immunol. Methods* 202:163 (1996), may be performed.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art. Low-affinity antibodies generally bind antigen slowly and tend to dissociate readily, whereas high-affinity antibodies generally bind antigen faster and tend to remain bound.

As used herein, the "Kd" or "Kd value" refers to a dissociation constant determined by BioLayer Interferometry, using an Octet QK384 instrument (Fortebio Inc., Menlo Park, Calif.) in kinetics mode. For example, anti-mouse Fc sensors are loaded with mouse-Fc fused antigen and then dipped into antibody-containing wells to measure concentration dependent association rates (kon). Antibody dissociation rates (koff) are measured in the final step, where the sensors are dipped into wells containing buffer only. The Kd is the ratio of koff/kon. (For further details see, Concepcion, J, et al., *Comb Chem High Throughput Screen*, 12(8), 791-800, 2009).

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The term "prostate cancer," as used herein, refers to a malignant tumor of glandular origin in the prostate gland.

The term "characterized by expression of PSMA" broadly refers to any disease or disorder in which PSMA expression is associated with or involved with one or more pathological processes that are characteristic of the disease or disorder. Such disorders include, but are not limited to, prostate cancer.

The terms "B-cell neoplasms" or "mature B-cell neoplasms" in the context of the present invention include, but are not limited to, all lymphoid leukemias and lymphomas, chronic lymphocytic leukemia, acute lymphoblastc leukemia, prolymphocytic leukemia, precursor B-lymphoblastic leukemia, hair cell leukemia, small lymphocytic lymphoma, B-cell prolymphocytic lymphoma, B-cell chronic lymphocytic leukemia, mantle cell lymphoma, Burkitt's lymphoma, follicular lymphoma, diffuse large B-cell lymphoma (DLBCL), multiple myeloma, lymphoplasmacytic lymphoma, splenic marginal zone lymphoma, plasma cell neoplasms, such as plasma cell myeloma, plasmacytoma, monoclonal immunoglobulin deposition disease, heavy chain disease, MALT lymphoma, nodal marginal B-cell lymphoma, intravascular large B-cell lymphoma, primary effusion lymphoma, lymphomatoid granulomatosis, non-Hodgkins lymphoma, Hodgkins lymphoma, hairy cell leukemia, primary effusion lymphoma and AIDS-related non-Hodgkins lymphoma.

The term "characterized by expression of CD19" broadly refers to any disease or disorder in which CD19 expression is associated with or involved with one or more pathological processes that are characteristic of the disease or disorder. Such disorders include, but are not limited to, B-cell neoplasms.

The term "characterized by expression of BCMA" broadly refers to any disease or disorder in which BCMA expression is associated with or involved with one or more pathological processes that are characteristic of the disease or disorder. Such disorders include, but are not limited to, B-cell neoplasms.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g., mouse, rat, etc.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores. A "frozen" formulation is one at a temperature below 0° C.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301. Vincent Lee Ed., Marcel Dekker, Inc., New York, N.Y., Pubs. (1991) and Jones. A. Adv. Drug Delivery Rev. 10: 29-90) (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g., Asn deamidation), oxidation (e.g., Met oxidation), isomerization (e.g., Asp isomeriation), clipping/hydrolysis/fragmentation (e.g., hinge region fragmentation), succinimide formation, unpaired cysteine(s), N-terminal extension, C-terminal processing, glycosylation differences, etc.

II. Detailed Description

Anti-BCMA Antibodies

The present invention relates to several families of closely related antibodies that bind to human BCMA. The variable regions of the antibodies of these families are described in US Patent Publication Nos. US20190352412 US20200157232 and US20200048348, and in PCT Publication Nos. WO2018237037 and WO2019006072, the disclosures of which applications are incorporated by reference herein in their entireties. A non-limiting selection of representative anti-BCMA heavy chain antibody variable domain sequences are provided below in Table 1.

TABLE 1

Anti-BCMA heavy chain antibody variable domain amino acid sequences.

| Clone ID # | SEQ_aa_FR1_FR4 | SEQ ID NO. |
|---|---|---|
| 308635 | EVQLLESGGGLVQAGGSLRLSCAASGFTVSSYGMSWVRQAPGKGPEWVSGIRGSDGSTYYADSVKGRFTISRDNSKNTLYLQMNSLRAEDTAVYHCAKQGENDGPFDYRGQGTLVTVSS | 92 |
| 308636 | EVQVLESGGGLVQPGGSLRLSCAASGFTVSSYGMSWVRQPPGKGMEWVSGIRGSDGSTFYADSVKG RFTISRDNATNTLYLQMNSLRAEDTAVYYCAKQGGNDGPFDYRGQGTLVTVSS | 87 |
| 308806 | EVQLLESGGGLVQPGGSLRLSCAASGFTISSYGMSWVRQAPGKGVEWVSG IRGSDGTTYYADSVKGRFTISRDSSRNTLYLQMNSLRAEDTAVYYCAKQGGNDGPFDHRGQGT LVTVSS | 88 |
| 308837 | EVQLLESGGGLVQPGGSLRLSCAASGFTVSSYGMSWVRQAPGKGPEWVSGIRGSDGSTYYADSVKGRFTISRDNATNTLYLQMNSLRAEDTAVYYCAKQGGNDGPFDYRGQGT LVTVSS | 89 |
| 308902 | EVQLLESGGGLVQPGGSLRLSCAASGFTVSSYGMSWVRQAPGKGPEWVSGIRGSDGSTYYADSVKGRFTISRDNSKNTLYLQMNSLRAEDTAVYYCAKQGENDGPFDHRGQGTLVTVSS | 90 |
| 308912 | EVQLLESGGGLVQPGGSLRLSCAASGFTVSSYGMSWVRQPPGKGMEWVSGIRGSDGSTYYADSVKGRFTISRDNAKNTLYLQMNSLRAEDTAVYYCAKQGGNDGPFDYRGQGTLVTVSS | 91 |

An anti-BCMA antibody sequence may be selected from those provided herein for development and therapeutic or other use, including, without limitation, use as a multispecific, e.g., a bispecific antibody. In some embodiments, bispecific or multispecific antibodies are provided, which may have any of the configurations discussed herein, including, without limitation, a TCA. Bispecific antibodies comprise at least the heavy chain variable region of an antibody specific for a protein other than BCMA.

Where a protein of the invention is a bispecific antibody, one binding moiety is specific for human BCMA while the other arm may be specific for target cells, tumor associated antigens, targeting antigens, e.g., integrins, etc., pathogen antigens, checkpoint proteins, and the like. Target cells specifically include cancer cells, such as hematologic tumors, e.g., B-cell tumors, as discussed below.

Various formats of bispecific antibodies are within the ambit of the invention, including, without limitation, single chain polypeptides, two chain polypeptides, three chain polypeptides, four chain polypeptides, and multiples thereof. The bispecific antibodies herein specifically include T-cell bispecific antibodies binding to BCMA, which is selectively expressed on plasma cells (PCs) and multiple myeloma (MM), and CD3 (anti-BCMA×anti-CD3 antibodies). Such antibodies induce potent T-cell mediated killing of cells carrying BCMA, and can be used to treat tumors, in particular hematologic tumors, such as B-cell tumors, as discussed further herein.

In a preferred embodiment, a bispecific antibody is a TCA comprising: an anti-CD3 VH domain that is paired with a light chain variable domain (VL), wherein the VH domain and the VL domain together have binding affinity for CD3; a heavy chain variable domain of a heavy chain-only antibody having binding affinity to BCMA, in a monovalent or bivalent configuration; and a variant human IgG4 Fc domain comprising a first heavy chain constant region sequence comprising an S228P mutation, an F234A mutation, an L235A mutation, and a T366W mutation (knob), and a second heavy chain constant region sequence comprising an S228P mutation, an F234A mutation, an L235A mutation, a T366S mutation, an L368A mutation, and a Y407V mutation (hole). This variant, or modified, IgG4 Fc domain prevents unwanted Fab exchange, reduces effector function of the antibody, and also facilitates heterodimerization of the heavy chain polypeptide subunits to form the bispecific antibody.

In some embodiments, the present invention comprises a bispecific antibody comprising i) an anti-CD3 heavy chain comprising SEQ ID NO: 56, ii) an anti-CD3 light chain comprising SEQ ID NO: 49, and iii) an anti-BCMA heavy chain comprising SEQ ID NO: 58.

In some embodiments, the present invention comprises a bispecific antibody comprising i) an anti-CD3 heavy chain comprising SEQ ID NO: 56, ii) an anti-CD3 light chain comprising SEQ ID NO: 49, and iii) an anti-BCMA heavy chain comprising SEQ ID NO: 59.

In some embodiments, the present invention comprises a bispecific antibody comprising i) an anti-CD3 heavy chain comprising SEQ ID NO: 56, ii) an anti-CD3 light chain comprising SEQ ID NO: 49, and iii) an anti-BCMA heavy chain comprising SEQ ID NO: 58, wherein the bispecific antibody does not comprise an anti-BCMA light chain.

In some embodiments, the present invention comprises a bispecific antibody comprising an anti-CD3 heavy chain comprising i) SEQ ID NO: 56, ii) an anti-CD3 light chain comprising SEQ ID NO: 49, and iii) an anti-BCMA heavy chain comprising SEQ ID NO: 59, wherein the bispecific antibody does not comprise an anti-BCMA light chain.

In some embodiments, the present invention comprises a human monoclonal IgG4 bispecific antibody comprising an anti-CD3 heavy chain comprising SEQ ID NO: 56, an anti-CD3 light chain comprising SEQ ID NO: 49, and an anti-BCMA heavy chain comprising SEQ ID NO: 58.

In some embodiments, the present invention comprises a human monoclonal IgG4 bispecific antibody comprising i)

an anti-CD3 heavy chain comprising SEQ ID NO: 56, ii) an anti-CD3 light chain comprising SEQ ID NO: 49, and iii) an anti-BCMA heavy chain comprising SEQ ID NO: 59.

In some embodiments, the present invention comprises a human monoclonal IgG4 bispecific antibody comprising i) an anti-CD3 heavy chain comprising SEQ ID NO: 56, ii) an anti-CD3 light chain comprising SEQ ID NO: 49, and an anti-BCMA heavy chain comprising SEQ ID NO: 58, wherein the bispecific antibody does not comprise an anti-BCMA light chain.

In some embodiments, the present invention comprises a human monoclonal IgG4 bispecific antibody comprising i) an anti-CD3 heavy chain comprising SEQ ID NO: 56, ii) an anti-CD3 light chain comprising SEQ ID NO: 49, and iii) an anti-BCMA heavy chain comprising SEQ ID NO: 59, wherein the bispecific antibody does not comprise an anti-BCMA light chain.

In some embodiments, the present invention comprises a human monoclonal IgG4 bispecific antibody, comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 56, said light chain comprises the amino acid sequence of SEQ ID NO: 49, and said bivalent second heavy chain comprises the amino acid sequence of SEQ ID NO: 58.

In some embodiments, the present invention comprises a human monoclonal IgG4 bispecific antibody, comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 56, said light chain comprises the amino acid sequence of SEQ ID NO: 49, and said bivalent second heavy chain comprises the amino acid sequence of SEQ ID NO: 59.

In some embodiments, the present invention comprises a human monoclonal IgG4 bispecific antibody, comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 56, said light chain comprises the amino acid sequence of SEQ ID NO: 49, and said bivalent second heavy chain comprises the amino acid sequence of SEQ ID NO: 58, and wherein said second binding arm does not comprise a light chain.

In some embodiments, the present invention comprises a human monoclonal IgG4 bispecific antibody, comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 56, said light chain comprises the amino acid sequence of SEQ ID NO: 49, and said bivalent second heavy chain comprises the amino acid sequence of SEQ ID NO: 59, and wherein said second binding arm does not comprise a light chain.

In some embodiments, the present invention comprises a bispecific three-chain antibody like molecule (TCA) comprising i) an anti-CD3 heavy chain comprising SEQ ID NO: 56, ii) an anti-CD3 light chain comprising SEQ ID NO: 49, and iii) an anti-BCMA heavy chain comprising SEQ ID NO: 58.

In some embodiments, the present invention comprises a bispecific three-chain antibody like molecule (TCA) comprising i) an anti-CD3 heavy chain comprising SEQ ID NO: 56, ii) an anti-CD3 light chain comprising SEQ ID NO: 49, and iii) an anti-BCMA heavy chain comprising SEQ ID NO: 59.

In some embodiments, the present invention comprises a bispecific three-chain antibody like molecule (TCA) comprising i) an anti-CD3 heavy chain comprising SEQ ID NO: 56, ii) an anti-CD3 light chain comprising SEQ ID NO: 49, and iii) an anti-BCMA heavy chain comprising SEQ ID NO: 58, wherein the bispecific antibody does not comprise an anti-BCMA light chain.

In some embodiments, the present invention comprises a bispecific three-chain antibody like molecule (TCA) comprising an anti-CD3 heavy chain comprising i) SEQ ID NO: 56, ii) an anti-CD3 light chain comprising SEQ ID NO: 49, and iii) an anti-BCMA heavy chain comprising SEQ ID NO: 59, wherein the bispecific antibody does not comprise an anti-BCMA light chain.

In some embodiments, the present invention comprises a human monoclonal IgG4 bispecific three-chain antibody like molecule (TCA) comprising an anti-CD3 heavy chain comprising SEQ ID NO: 56, an anti-CD3 light chain comprising SEQ ID NO: 49, and an anti-BCMA heavy chain comprising SEQ ID NO: 58.

In some embodiments, the present invention comprises a human monoclonal IgG4 bispecific three-chain antibody like molecule (TCA) comprising i) an anti-CD3 heavy chain comprising SEQ ID NO: 56, ii) an anti-CD3 light chain comprising SEQ ID NO: 49, and iii) an anti-BCMA heavy chain comprising SEQ ID NO: 59.

In some embodiments, the present invention comprises a human monoclonal IgG4 bispecific three-chain antibody like molecule (TCA) comprising i) an anti-CD3 heavy chain comprising SEQ ID NO: 56, ii) an anti-CD3 light chain comprising SEQ ID NO: 49, and an anti-BCMA heavy chain comprising SEQ ID NO: 58, wherein the bispecific antibody does not comprise an anti-BCMA light chain.

In some embodiments, the present invention comprises a human monoclonal IgG4 bispecific three-chain antibody like molecule (TCA) comprising i) an anti-CD3 heavy chain comprising SEQ ID NO: 56, ii) an anti-CD3 light chain comprising SEQ ID NO: 49, and iii) an anti-BCMA heavy chain comprising SEQ ID NO: 59, wherein the bispecific antibody does not comprise an anti-BCMA light chain.

In some embodiments, the present invention comprises a human monoclonal IgG4 bispecific three-chain antibody like molecule (TCA) comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 56, said light chain comprises the amino acid sequence of SEQ ID NO: 49, and said bivalent second heavy chain comprises the amino acid sequence of SEQ ID NO: 58.

In some embodiments, the present invention comprises a human monoclonal IgG4 bispecific three-chain antibody like molecule (TCA) comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 56, said light chain comprises the amino acid sequence of SEQ ID NO: 49, and said bivalent second heavy chain comprises the amino acid sequence of SEQ ID NO: 59.

In some embodiments, the present invention comprises a human monoclonal IgG4 bispecific three-chain antibody like molecule (TCA) comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 56, said light chain comprises the amino acid sequence of SEQ ID NO: 49, and said bivalent second heavy chain comprises the amino acid sequence of SEQ ID NO: 58, and wherein said second binding arm does not comprise a light chain.

In some embodiments, the present invention comprises a human monoclonal IgG4 bispecific three-chain antibody like molecule (TCA) comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 56, said light chain comprises the amino acid sequence of SEQ ID NO: 49, and said bivalent second heavy chain comprises the amino acid sequence of SEQ ID NO: 59, and wherein said second binding arm does not comprise a light chain.

In some embodiments, the present invention comprises a bispecific antibody comprising i) an anti-CD3 heavy chain comprising SEQ ID NO: 75, ii) an anti-CD3 light chain comprising SEQ ID NO: 49, and iii) an anti-BCMA heavy chain comprising SEQ ID NO: 76.

In some embodiments, the present invention comprises a bispecific antibody comprising i) an anti-CD3 heavy chain comprising SEQ ID NO: 75, ii) an anti-CD3 light chain comprising SEQ ID NO: 49, and iii) an anti-BCMA heavy chain comprising SEQ ID NO: 77.

In some embodiments, the present invention comprises a bispecific antibody comprising i) an anti-CD3 heavy chain comprising SEQ ID NO: 75, ii) an anti-CD3 light chain comprising SEQ ID NO: 49, and iii) an anti-BCMA heavy chain comprising SEQ ID NO: 76, wherein the bispecific antibody does not comprise an anti-BCMA light chain.

In some embodiments, the present invention comprises a bispecific antibody comprising an anti-CD3 heavy chain comprising i) SEQ ID NO: 75, ii) an anti-CD3 light chain comprising SEQ ID NO: 49, and iii) an anti-BCMA heavy chain comprising SEQ ID NO: 77, wherein the bispecific antibody does not comprise an anti-BCMA light chain.

In some embodiments, the present invention comprises a human monoclonal IgG4 bispecific antibody comprising an anti-CD3 heavy chain comprising SEQ ID NO: 75, an anti-CD3 light chain comprising SEQ ID NO: 49, and an anti-BCMA heavy chain comprising SEQ ID NO: 76.

In some embodiments, the present invention comprises a human monoclonal IgG4 bispecific antibody comprising i) an anti-CD3 heavy chain comprising SEQ ID NO: 75, ii) an anti-CD3 light chain comprising SEQ ID NO: 49, and iii) an anti-BCMA heavy chain comprising SEQ ID NO: 77.

In some embodiments, the present invention comprises a human monoclonal IgG4 bispecific antibody comprising i) an anti-CD3 heavy chain comprising SEQ ID NO: 75, ii) an anti-CD3 light chain comprising SEQ ID NO: 49, and an anti-BCMA heavy chain comprising SEQ ID NO: 76, wherein the bispecific antibody does not comprise an anti-BCMA light chain.

In some embodiments, the present invention comprises a human monoclonal IgG4 bispecific antibody comprising i) an anti-CD3 heavy chain comprising SEQ ID NO: 75, ii) an anti-CD3 light chain comprising SEQ ID NO: 49, and iii) an anti-BCMA heavy chain comprising SEQ ID NO: 77, wherein the bispecific antibody does not comprise an anti-BCMA light chain.

In some embodiments, the present invention comprises a human monoclonal IgG4 bispecific antibody, comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 75, said light chain comprises the amino acid sequence of SEQ ID NO: 49, and said bivalent second heavy chain comprises the amino acid sequence of SEQ ID NO: 76.

In some embodiments, the present invention comprises a human monoclonal IgG4 bispecific antibody, comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 75, said light chain comprises the amino acid sequence of SEQ ID NO: 49, and said bivalent second heavy chain comprises the amino acid sequence of SEQ ID NO: 77.

In some embodiments, the present invention comprises a human monoclonal IgG4 bispecific antibody, comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 75, said light chain comprises the amino acid sequence of SEQ ID NO: 49, and said bivalent second heavy chain comprises the amino acid sequence of SEQ ID NO: 76, and wherein said second binding arm does not comprise a light chain.

In some embodiments, the present invention comprises a human monoclonal IgG4 bispecific antibody, comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 75, said light chain comprises the amino acid sequence of SEQ ID NO: 49, and said bivalent second heavy chain comprises the amino acid sequence of SEQ ID NO: 77, and wherein said second binding arm does not comprise a light chain.

In some embodiments, the present invention comprises a bispecific three-chain antibody like molecule (TCA) comprising i) an anti-CD3 heavy chain comprising SEQ ID NO: 75, ii) an anti-CD3 light chain comprising SEQ ID NO: 49, and iii) an anti-BCMA heavy chain comprising SEQ ID NO: 76.

In some embodiments, the present invention comprises a bispecific three-chain antibody like molecule (TCA) comprising i) an anti-CD3 heavy chain comprising SEQ ID NO:

75, ii) an anti-CD3 light chain comprising SEQ ID NO: 49, and iii) an anti-BCMA heavy chain comprising SEQ ID NO: 77.

In some embodiments, the present invention comprises a bispecific three-chain antibody like molecule (TCA) comprising i) an anti-CD3 heavy chain comprising SEQ ID NO: 75, ii) an anti-CD3 light chain comprising SEQ ID NO: 49, and iii) an anti-BCMA heavy chain comprising SEQ ID NO: 76, wherein the bispecific antibody does not comprise an anti-BCMA light chain.

In some embodiments, the present invention comprises a bispecific three-chain antibody like molecule (TCA) comprising an anti-CD3 heavy chain comprising i) SEQ ID NO: 75, ii) an anti-CD3 light chain comprising SEQ ID NO: 49, and iii) an anti-BCMA heavy chain comprising SEQ ID NO: 77, wherein the bispecific antibody does not comprise an anti-BCMA light chain.

In some embodiments, the present invention comprises a human monoclonal IgG4 bispecific three-chain antibody like molecule (TCA) comprising an anti-CD3 heavy chain comprising SEQ ID NO: 75, an anti-CD3 light chain comprising SEQ ID NO: 49, and an anti-BCMA heavy chain comprising SEQ ID NO: 76.

In some embodiments, the present invention comprises a human monoclonal IgG4 bispecific three-chain antibody like molecule (TCA) comprising i) an anti-CD3 heavy chain comprising SEQ ID NO: 75, ii) an anti-CD3 light chain comprising SEQ ID NO: 49, and iii) an anti-BCMA heavy chain comprising SEQ ID NO: 77.

In some embodiments, the present invention comprises a human monoclonal IgG4 bispecific three-chain antibody like molecule (TCA) comprising i) an anti-CD3 heavy chain comprising SEQ ID NO: 75, ii) an anti-CD3 light chain comprising SEQ ID NO: 49, and an anti-BCMA heavy chain comprising SEQ ID NO: 76, wherein the bispecific antibody does not comprise an anti-BCMA light chain.

In some embodiments, the present invention comprises a human monoclonal IgG4 bispecific three-chain antibody like molecule (TCA) comprising i) an anti-CD3 heavy chain comprising SEQ ID NO: 75, ii) an anti-CD3 light chain comprising SEQ ID NO: 49, and iii) an anti-BCMA heavy chain comprising SEQ ID NO: 77, wherein the bispecific antibody does not comprise an anti-BCMA light chain.

In some embodiments, the present invention comprises a human monoclonal IgG4 bispecific three-chain antibody like molecule (TCA) comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 75, said light chain comprises the amino acid sequence of SEQ ID NO: 49, and said bivalent second heavy chain comprises the amino acid sequence of SEQ ID NO: 76.

In some embodiments, the present invention comprises a human monoclonal IgG4 bispecific three-chain antibody like molecule (TCA) comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 75, said light chain comprises the amino acid sequence of SEQ ID NO: 49, and said bivalent second heavy chain comprises the amino acid sequence of SEQ ID NO: 77.

In some embodiments, the present invention comprises a human monoclonal IgG4 bispecific three-chain antibody like molecule (TCA) comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 75, said light chain comprises the amino acid sequence of SEQ ID NO: 49, and said bivalent second heavy chain comprises the amino acid sequence of SEQ ID NO: 76, and wherein said second binding arm does not comprise a light chain.

In some embodiments, the present invention comprises a human monoclonal IgG4 bispecific three-chain antibody like molecule (TCA) comprising (i) a first binding arm that binds to human CD3 and (ii) a second binding arm that binds to human BCMA, said first binding arm comprising a first heavy chain and a light chain, and said second binding arm comprising a bivalent second heavy chain, wherein said first heavy chain comprises the amino acid sequence of SEQ ID NO: 75, said light chain comprises the amino acid sequence of SEQ ID NO: 49, and said bivalent second heavy chain comprises the amino acid sequence of SEQ ID NO: 77, and wherein said second binding arm does not comprise a light chain.

Anti-CD19 Antibodies

The present invention provides a family of closely related antibodies that bind to human CD19. The variable regions of the antibodies of this family are described in PCT Publication No. WO2020018922, the disclosure of which is incorporated by reference herein in its entirety. An anti-CD19 antibody sequence may be selected from those provided herein for development and therapeutic or other use, including, without limitation, use as a multispecific, e.g., a bispecific antibody. In some embodiments, bispecific or multispecific antibodies are provided, which may have any of the configurations discussed herein, including, without limitation, a TCA. Bispecific antibodies comprise at least the heavy chain variable region of an antibody specific for a protein other than CD19.

Where a protein of the invention is a bispecific antibody, one binding moiety is specific for human CD19 while the other arm may be specific for target cells, tumor associated antigens, targeting antigens, e.g., integrins, etc., pathogen antigens, checkpoint proteins, and the like. Target cells specifically include cancer cells, such as hematologic tumors, e.g., B-cell tumors, as discussed below.

Various formats of bispecific antibodies are within the ambit of the invention, including, without limitation, single chain polypeptides, two chain polypeptides, three chain polypeptides, four chain polypeptides, and multiples thereof. The bispecific antibodies herein specifically include T-cell bispecific antibodies binding to CD19, which is selectively expressed on mature B-cells, and CD3 (anti-CD19× anti-CD3 antibodies). Such antibodies induce potent T-cell mediated killing of cells expressing CD19, and can be used to treat tumors, in particular hematologic tumors, such as B-cell tumors, as discussed further herein.

In a preferred embodiment, a bispecific antibody is a TCA comprising: an anti-CD3 VH domain that is paired with a light chain variable domain (VL), wherein the VH domain and the VL domain together have binding affinity for CD3; a heavy chain variable domain of a heavy chain-only antibody having binding affinity to CD19, in a monovalent or bivalent configuration; and a variant human IgG4 Fc domain comprising a first heavy chain constant region sequence comprising an S228P mutation, an F234A mutation, an L235A mutation, and a T366W mutation (knob), and a second heavy chain constant region sequence comprising an S228P mutation, an F234A mutation, an L235A mutation, a T366S mutation, an L368A mutation, and a Y407V mutation (hole). This variant, or modified, IgG4 Fc domain prevents unwanted Fab exchange, reduces effector function of the antibody, and also facilitates heterodimerization of the heavy chain polypeptide subunits to form the bispecific antibody.

Anti-PSMA Antibodies

The present invention provides a family of closely related antibodies that bind to human PSMA. The antibodies of this family are exemplified by the provided heavy chain variable region ($V_H$) sequences of SEQ ID NOs: 24 to 54 set forth in Table 2. The families of antibodies provide a number of benefits that contribute to utility as clinically therapeutic agent(s). The antibodies include members with a range of binding affinities, allowing the selection of a specific sequence with a desired binding affinity.

TABLE 2

Anti-PSMA heavy chain antibody variable domain amino acid sequences.

| Clone ID # | SEQ_aa_FR1_FR4 | SEQ ID NO. |
| --- | --- | --- |
| 325920 | QLQLQESGPGLVKPSETLSLTCTVSGGSISSSSYYWGWIRQPPGKGLEWIGSIDYS GYTYYNPSLQSRVTISVDTSKNQFSLKLSSVTAADTAVYNCARHKAATADFDYR GQGTLVTVSS | 1 |
| 346181 | QLQLQESGPGLVKPSETLSLTCTVSGGSISSSNYFWGWIRQSPGKGLEWIGSIDYS GYTYYNPSLKSRVTISVDTSKNQFSLKLSSVTAADTAVYNCARHKAATADFDYR GQGTLVTVSS | 2 |
| 346165 | QLQLQESGPGLVKPSETLSLTCTVSGGSISSSSYYWGWIRQPPGKGLEWIGSVDYS GYTYYNPSLQSRVTISVDTSKNQFSLKLSSVTAADTAVYNCARHKAATADFDYR GQGTLVTVSS | 3 |
| 346172 | QLQLQESGPGLVKPSETLSLTCTVSGGSISSSSYYWGWIRQPPGKGLEWIGSIDYS GYTYYNPSLKSRVTISVDTSKNQFSLKLSSVTAADTAVYNCARHKAATADFDYR GQGTLVTVSS | 4 |
| 326109 | QLQLQESGPGLVKPSETLSLTCTVSGGSISSNSYYWGWIRQSPGKGLEWLGSIYDS GSTHYNPSLKSRVIISGDTSKNQFSLKLSSVTAADTAVYYCARHKAATADFDYRG QGTLVTVSS | 5 |
| 325867 | QVQLVESGGGVVQPGRSLRLSCAASGFSFRSYGMHWVRQAPGKGLEWVAVIWY DGSNKYYADSVKGRFTISRDYSKNTLYLQMNSLRAEDTAVYYCAREPRIGYYYE SSGYDSLDYRGQGTLVTVSS | 6 |
| 325742 | QVQLVESGGGVVQPGRSLRLSCAASGFSFSSYGMHWVRQAPGKGLEWVAVIWY DGSNKYYADSVKGRFTISRDYSKNTLYLQMNSLRAEDTAVYYCAREPRIGYYYE SSGYDSLDYRGQGTLVTVSS | 7 |
| 325748 | QVQLVESGGGVVQPGRSLRLSCAASGFSFSSYGMHWVRQAPGKGLEGVAVIWY DGSNRYYADSVKGRFTISRDNSKNTLYLQMNSLRAEDTAVYYCAREPRIGYYYE SSGYYSLDYRGQGTLVTVSS | 8 |
| 325940 | QVQLVESGGGVVQPGRSLRLSCAASGFIFRSYGMHWVRQAPGKGPEWVAVIWY DGSNKYYADSVKGRFTISRDNSKNTLYLQMNSLRAEDTAVYYCAREPRIGYYYE SSGYYSLDYRGQGTLVTVSS | 9 |
| 325836 | QVQLVESGGGVVQPGRSLRLSCAASGFSFRSYGMHWVRQAPGKGLEWVAVIWY DGSNKYYADSVKGRFTISRDYSKNTLYLQMNSLRAEDTAVYYCAREPRIGYYYD SSGYDSLDYRGQGTLVTVSS | 10 |
| 326027 | QVQLVESGGGVVQPGRSLRLSCAASGFSFRSYGMHWVRQAPGKGLEWVAVIWY DGSNKYYADSVKGRFTISRDNSKNTLYLQMNSLRAEDTAVYYCAREPRIGYYYD SSGYDSLDYRGQGTLVTVSS | 11 |
| 326087 | QVQLVESGGGVVQPGRSLRLSCAASGFIFRSYGMHWVRQAPGKGPEWVAVIWY DGSNKYYADSVKGRFTISRDNSKNTLYLQMNSLRAEDTAVYYCAREPRIGYYYD SSGYDSLDYRGQGTLVTVSS | 12 |
| 326084 | QVQLVESGGGVVQPGRSLRLSCAASGFSFSSYGMHWVRQAPGKGLEGVAVIWY DGSNRYYADSVKGRFTISRDNSKNTLYLQMNSLRAEDTAVYYCAREPRIGYYYD SSGYYSLDYRGQGTLVTVSS | 13 |
| 326028 | QVQLVESGGGVVQPGRSLRLSCAASGFSFRSYGMHWVRQAPGKGLEWVAVISY DGSNKYYADSVKGRFTISRDYSKNTLYLQMNSLRAEDTAVYYCAREPRIGYYYD SSGYDSLDYRGQGTLVTVSS | 14 |
| 345497 | QVQLVESGGGVVQPGRSLRLSCAASGFSFSRYGMHWVRQAPGKGLEGVAVIWY DGSNRYYADSVKGRFTISRDNSKNTLYLQMNSLRAEDTAVYYCAREPRIGYYYE SSGYYSLDYRGQGTLVTVSS | 15 |

TABLE 2-continued

Anti-PSMA heavy chain antibody variable domain amino acid sequences.

| Clone ID # | SEQ_aa_FR1_FR4 | SEQ ID NO. |
|---|---|---|
| 326029 | QVQLVESGGGVVQPGRSLRLSCAASGFSFSRYGMHWVRQAPGKGLEWVAVISY DGSNKYYADSVKGRFTISRDNSKNTLYLQMNSLRAEDTAVYYCAREPRVGYYY ETSGYYSLDYRGQGTLVTVSS | 16 |
| 345461 | QVQLVESGGGVVQPGRSLRLSCAASGFSFTSYGMHWVRQAPGKGLEGVAVIWY DGSNRYYADSVKGRFTISRDNSKNTLYLQMNSLRAEDTAVYYCAREPRIGYYYE SSGYYSLDYRGQGTLVTVSS | 17 |
| 345493 | QVQLVESGGGVVQPGRSLRLSCAASGFSFSRYGMHWVRQAPGKGLEWVAVIWY DGSNRYYADSVKGRFTISRDNSKNTLYLQMNSLRAEDTAVYYCAREPRIGYYYE SSGYYSLDYRGQGTLVTVSS | 18 |
| 345436 | QVQLVESGGGVVQPGRSLRLSCAASGFSFSRYGMHWVRQAPGKGLEGVAVIWY DGSNKYYADSVKGRFTISRDNSKNTLYLQMNSLRAEDTAVYYCAREPRIGYYYE SSGYYSLDYRGQGTLVTVSS | 19 |
| 345443 | QVQLVESGGGVVQPGRSLRLSCAASGFSFSSYGMHWVRQAPGKGLEGVAVIWY DGSNRYYADSVKGRFTISRDNSKNTLFLQMNSLRAEDTAVYYCAREPRIGYYYE SSGYYSLDYRGQGTLVTVSS | 20 |
| 345490 | QVQLVESGGGLVKPGGSLRLSCAASGFSFSSYGMHWVRQAPGKGLEGVAVIWY DGSNRYYADSVKGRFTISRDNSKNTLYLQMNSLRAEDTAVYYCAREPRIGYYYE SSGYYSLDYRGQGTLVTVSS | 21 |
| 345482 | QVQLVESGGGVVQPGRSLRLSCAASGFSFSSYGMHWVRQAPGKGLEGVAVIWY DGSNRYYADSVKGRFTISRDSSKNTLYLQMNSLRAEDTAVYYCAREPRIGYYYE SSGYYSLDYRGQGTLVTVSS | 22 |
| 345485 | QVQLVESGGGVVQPGRSLRLSCAASGFSFRSYGMHWVRQAPGKGLEWVAVIWY DGSNKYYADSVKGRFTISRDNSKNTMYLQMNSLRAEDTAVYYCAREPRIGYYYE SSGYYSLDYRGQGTLVTVSS | 23 |
| 345463 | QVQLVESGGGVVQPGRSLRLSCAASGFIFRSYGMHWVRQAPGKGPEWVAVIWY DGSNKYYADSVKGRFTISRDNSKNTLYLQMNSLRAEDTAVYYCAREPRIGYYYE SSGYYSLDYRGQGTLVTVSS | 24 |
| 325932 | QVQLVESGGGVVQPGRSLRLSCAASGFSFSSYGMHWVRQAPGKGLEGVAVIWY DGSNRYYADSVKGRFTISRDNSKNTLYLQMNSLRAEDTAVYYCAREPRIGYYYE SSGYYSLDYRGQGTLVTVSS | 25 |
| 345505 | QVQLVESGGGVVQPGRSLRLSCAASGFTFISYGMHWVRQAPGKGLEGVAVIWY DGSNRYYADSVKGRFTISRDNSKNTLYLQMNSLRAEDTAVYYCAREPRIGYYYE SSGYYSLDYRGQGTLVTVSS | 26 |
| 345508 | QVQLVESGGGVVQPGRSLRLSCAASGFSFSSYGMHWVRQAPGKGPEWVAVIWY DGSNRYYADSVKGRFTISRDNSKNTLYLQMNSLRAEDTAVYYCAREPRIGYYYE SSGYYSLDYRGQGTLVTVSS | 27 |
| 345480 | QVQLVESGGGVVQPGRSLRLSCAASGFSFSSYGMHWVRQAPGKGLEWVAVIWY DGSNRYYADSVKGRFTISRDNSKNTLYLQMNSLRAEDTAVYYCAREPRIGYYYE SSGYYSLDYRGQGTLVTVSS | 28 |
| 326116 | QVQLVESGGGVVQPGRSLRLSCAASGFSFSRYGMHWVRQAPGKGLEGVAVISY DGSNKYYADSVKGRFTISRDYSKNTLYLQMNSLRAEDTAVYYCAREPRIGYYYD SSGYDSLDYRGQGTLVTVSS | 29 |
| 345509 | QVQLVESGGGLVQPGGSLRLSCAASGFSFSSYGMHWVRQAPGKGLEGVAVIWY DGSNKYYADSVKGRFTISRDNSKNTMYLQMNSLRAEDTAVYYCAREPRIGYYYE SSGYYSLDYRGQGTLVTVSS | 30 |
| 345444 | QVQLVESGGGVVQPGRSLRLSCAASGFTFSSYGMHWVRQAPGKGLEGVAVIWY DGSNRYYADSVKGRFTISRDNSKNTLYLQMNSLRAEDTAVYYCAREPRIGYYYE SSGYYSLDYRGQGTLVTVSS | 31 |
| 345421 | QVQLVESVGGVVQPGRSLRLSCAASGFSFSSYGMHWVRQAPGKGLEGVAVIWY DGSNRYYADSVKGRFTISRDNSKNTLYLQMNSLRAEDTAVYYCAREPRIGYYYE SSGYYSLDYRGQGTLVTVSS | 32 |
| 345447 | QVQLVESGGGVVQPGRSLRLSCAASGFSFSSYGMHWVRQAPGKGLEGVAVISY DGSNRYYADSVKGRFTISRDNSKNTLYLQMNSLRAEDTAVYYCAREPRIGYYYE SSGYYSLDYRGQGTLVTVSS | 33 |

TABLE 2-continued

Anti-PSMA heavy chain antibody variable domain amino acid sequences.

| Clone ID # | SEQ_aa_FR1_FR4 | SEQ ID NO. |
|---|---|---|
| 345510 | QVQLVESGGGVVQPGRSLRLSCAASGFSFSSYGMHWVRQAPGKGLEWVAVIWY DGSNKYYADSVKGRFTISRDNSKNTMYLQMNSLRAEDTAVYYCAREPRIGYYE SSGYYSLDYRGQGTLVTVSS | 34 |
| 345438 | QVQLVESGGGVVQPGRSLRLSCAASGFSFSSYGMHWVRQAPGKGPEWVAVIWY DGSNKYYADSVKGRFTISRDNSKNTLYLQMNSLRAEDTAVYYCAREPRIGYYE SSGYYSLDYRGQGTLVTVSS | 35 |

In a preferred embodiment, a bispecific antibody is a TCA comprising: an anti-CD3 $V_H$ domain that is paired with a light chain variable domain (VL), wherein the $V_H$ domain and the VL domain together have binding affinity for CD3; a heavy chain variable domain of a heavy chain-only antibody having binding affinity to PSMA, in a monovalent or bivalent configuration; and a variant human IgG4 Fc domain comprising a first heavy chain constant region sequence comprising an S228P mutation, an F234A mutation, an L235A mutation, and a T366W mutation (knob), and a second heavy chain constant region sequence comprising an S228P mutation, an F234A mutation, an L235A mutation, a T366S mutation, an L368A mutation, and a Y407V mutation (hole). This variant, or modified, IgG4 Fc domain prevents unwanted Fab exchange, reduces effector function of the antibody, and also facilitates heterodimerization of the heavy chain polypeptide subunits to form the bispecific antibody.

CD3× Target Protein Three-Chain Antibody-Like Molecules (TCAs)

In some embodiments, bispecific or multi-specific antibodies are provided, which may have any of the configurations discussed herein, including, without limitation, a bispecific three-chain antibody like molecule. In some embodiments, a multi-specific antibody can comprise a heavy chain/light chain pair that has binding specificity for a first antigen (e.g., CD3), and a heavy chain from a heavy chain-only antibody. In certain embodiments, the heavy chain from the heavy chain only antibody comprises an Fc portion comprising CH2 and/or CH3 and/or CH4 domains, in the absence of a CH1 domain. In one particular embodiment, a bispecific antibody comprises a heavy chain/light chain pair that has binding specificity for an antigen on an effector cell (e.g., a CD3 protein on a T-cell), and a heavy chain from a heavy chain-only antibody comprising an antigen-binding domain that has binding specificity for BCMA, PSMA, or CD19.

In a preferred embodiment, a bispecific antibody is a TCA comprising: an anti-CD3 VH domain that is paired with a light chain variable domain (VL), wherein the VH domain and the VL domain together have binding affinity for CD3; a heavy chain variable domain of a heavy chain-only antibody having binding affinity to BCMA, PSMA, or CD19; and a variant human IgG4 Fc domain comprising a first heavy chain constant region sequence comprising an S228P mutation, an F234A mutation, an L235A mutation, and a T366W mutation (knob), and a second heavy chain constant region sequence comprising an S228P mutation, an F234A mutation, an L235A mutation, an L368A mutation, and a Y407V mutation (hole). This variant, or modified, IgG4 Fc domain prevents unwanted Fab exchange, reduces effector function of the antibody, and also facilitates heterodimerization of the heavy chain polypeptide subunits to form the bispecific antibody.

In some embodiments, a multi-specific antibody comprises a CD3-binding VH domain that is paired with a light chain variable domain. In certain embodiments, the light chain is a fixed light chain. In some embodiments, the CD3-binding VH domain comprises a CDR1 sequence of SEQ ID NO: 36, a CDR2 sequence of SEQ ID NO: 37, and a CDR3 sequence of SEQ ID NO: 38, in a human VH framework. In some embodiments, the fixed light chain comprises a CDR1 sequence of SEQ ID NO: 39, a CDR2 sequence of SEQ ID NO: 40, and a CDR3 sequence of SEQ ID NO: 41, in a human VL framework. Together, the CD3-binding VH domain and the light chain variable domain have binding affinity for CD3. In some embodiments, a CD3-binding VH domain comprises a heavy chain variable region sequence of SEQ ID NO: 42. In some embodiments, a CD3-binding VH domain comprises a sequence having at least about 80%, at least about 85%, at least about 90%, at least about 95%, or at least about 99% percent identity to the heavy chain variable region sequence of SEQ ID NO: 42. In some embodiments, a fixed light chain comprises a light chain variable region sequence of SEQ ID NO: 43. In some embodiments, a fixed light chain comprises a sequence having at least about 80%, at least about 85%, at least about 90%, at least about 95%, or at least about 99% percent identity to the heavy chain variable region sequence of SEQ ID NO: 43.

Multi-specific antibodies comprising the above-described CD3-binding VH domain and light chain variable domain have advantageous properties, for example, as described in PCT Publication No. WO2018/052503, the disclosure of which is incorporated by reference herein in its entirety. Any of the multi-specific antibodies and antigen-binding domains described herein, having binding affinity to BCMA, PSMA, or CD19, can be combined with the CD3-binding domains and fixed light chain domains described herein to generate multi-specific antibodies having binding affinity to one or more BCMA epitopes, PSMA epitopes, or CD19 epitopes, as well as CD3.

TABLE 3

Anti-CD3 Heavy and Light Chain CDR1, CDR2, CDR3 amino acid sequences.

| | SEQ_aa_CDR1 | SEQ_aa_CDR2 | SEQ_aa_CDR3 |
|---|---|---|---|
| Heavy Chain | GFTFDDYA (SEQ ID NO: 36) | ISWNSGSI (SEQ ID NO: 37) | AKDSRGYGDYRLGGAY (SEQ ID NO: 38) |

TABLE 3-continued

Anti-CD3 Heavy and Light Chain CDR1, CDR2, CDR3 amino acid sequences.

| | SEQ_aa_CDR1 | SEQ_aa_CDR2 | SEQ_aa_CDR3 |
|---|---|---|---|
| Light Chain | QSVSSN (SEQ ID NO: 39) | GAS (SEQ ID NO: 40) | QQYNNWPWT (SEQ ID NO: 41) |

TABLE 4

Anti-CD3 heavy and light chain variable region amino acid sequences.

| | |
|---|---|
| VH | EVQLVESGGGLVQPGRSLRLSCAASGFTFDDYAMHWVRQAPGK GLEWVSGISWNSGSIGYADSVKGRFTISRDNAKNSLYLQMNSL RAEDTALYYCAKDSRGYGDYRLGGAYWGQGTLVTVSS (SEQ ID NO: 42) |
| VL | EIVMTQSPATLSVSPGERATLSCRASQSVSSNLAWYQQKPGQA PRLLIYGASTRATGIPARFSGSGSGTEFTLTISSLQSEDFAVY YCQQYNNWPWTFGQGTKVEIK (SEQ ID NO: 43) |

TABLE 5

Human IgG1 and IgG4 Fc region sequences.

| | |
|---|---|
| Human IgG1 (UniProt No. P01857) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSDE LTKNQVSLTCLVKGFYPSDIAVEWESNGQPENNYKTTPPVLDSDGSFF LYSKLTVDKSRWQQGNVFSCSVMHEALHNHYT QKSLSLSPGK (SEQ ID NO: 44) |
| Human IgG4 (UniProt No. P01861) | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVDK RVESKYGPPCPSCPAPEFLGGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLY SRLTVDKSRWQEGNVFSCSVMHEALHNHYTQKS LSLSLGK (SEQ ID NO: 45) |
| Human IgG1 with silencing mutations (Fc region) | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK KVEPKSCDKTHTCPPCPAPEAAGGPSVFLFPPKPKDTLMISRTPEVTCV VVDVSHEDPEVKFNWYVDGVEVHNAKTKPREEQYNSTYRVVSVLTV LHQDWLNGKEYKCKVSNKALPAPIEKTISKAKGQPREPQVYTLPPSRE EMTKNQVSLTCLVKGFYPSDIAVEWESNGQPENNYKTTPPVLDSDGS FFLYSKLTVDKSRWQQGNVFSCSVMHEALHNHYTQKSLSLSPGK (SEQ ID NO: 46) |
| Human IgG4 with silencing mutations (Fc region) | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVDK RVESKYGPPCPPPCPAPEAAGGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMT KNQVSLTCLVKGFYPSDIAVEWESNGQPENNYKTTPPVLDSDGSFFLY SRLTVDKSRWQEGNVFSCSVMHEALHNHYTQKSLSLSLGK (SEQ ID NO: 47) |

TABLE 6

Anti-CD3 antibody sequences.

| | |
|---|---|
| Anti-CD3 light chain constant region sequence (kappa light chain) | RTVAAPSVFIFPPSDEQLKSGTASVVCLLNNFYPREAKVQWKVDNAL QSGNSQESVTEQDSKDSTYSLSSTLTLSKADYEKHKVYACEVTHQGL SSPVTKSFNRGEC (SEQ ID NO: 48) |
| Anti-CD3 full length light chain (VL + kappa CL) | EIVMTQSPATLSVSPGERATLSCRASQSVSSNLAWYQQKPGQAPRLLI YGASTRATGIPARFSGSGSGTEFTLTISSLQSEDFAVYYCQQYNNWPW TFGQGTKVEIKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC (SEQ ID NO: 49) |
| Anti-CD3 heavy chain sequence (VH (F2B) + wt IgG1 Fc) | EVQLVESGGGLVQPGRSLRLSCAASGFTFDDYAMHWVRQAPGKGLE WVSGISWNSGSIGYADSVKGRFTISRDNAKNSLYLQMNSLRAEDTAL YYCAKDSRGYGDYRLGGAYWGQGTLVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNW YVDGVEVHNAKTKPREEQYNSTYRVVSVLTVLHQDWLNGKEYKCK VSNKALPAPIEKTISKAKGQPREPQVYTLPPSREEMTKNQVSLTCLVK |

TABLE 6-continued

Anti-CD3 antibody sequences.

|  |  |
|---|---|
|  | GFYPSDIAVEWESNGQPENNYKTTPPVLDSDGSFFLYSKLTVDKSRW QQGNVFSCSVMHEALHNHYTQKSLSLSPGK (SEQ ID NO: 50) |
| Anti-CD3 heavy chain sequence (VH F2B + silenced IgG1 Fc) | EVQLVESGGGLVQPGRSLRLSCAASGFTFDDYAMHWVRQAPGKGLE WVSGISWNSGSIGYADSVKGRFTISRDNAKNSLYLQMNSLRAEDTAL YYCAKDSRGYGDYRLGGAYWGQGTLVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPC PAPEAAGGPSVFLFPPKPKDTLMISRTPEVTCVVVDVSHEDPEVKFNW YVDGVEVHNAKTKPREEQYNSTYRVVSVLTVLHQDWLNGKEYKCK VSNKALPAPIEKTISKAKGQPREPQVYTLPPSREEMTKNQVSLTCLVK GFYPSDIAVEWESNGQPENNYKTTPPVLDSDGSFFLYSKLTVDKSRW QQGNVFSCSVMHEALHNHYTQKSLSLSPGK (SEQ ID NO: 51) |
| Anti-CD3 heavy chain VH F2B (+ wt IgG4 Fc) | EVQLVESGGGLVQPGRSLRLSCAASGFTFDDYAMHWVRQAPGKGLE WVSGISWNSGSIGYADSVKGRFTISRDNAKNSLYLQMNSLRAEDTAL YYCAKDSRGYGDYRLGGAYWGQGTLVTVSSASTKGPSVFPLAPCSRS TSESTAALGCLVKDYFPEPVTVSWNSGALTSGVHTFPAVLQSSGLYSL SSVVTVPSSSLGTKTYTCNVDHKPSNTKVDKRVESKYGPPCPSCPAPE FLGGPSVFLFPPKPKDTLMISRTPEVTCVVVDVSQEDPEVQFNWYVDG VEVHNAKTKPREEQFNSTYRVVSVLTVLHQDWLNGKEYKCKVSNKG LPSSIEKTISKAKGQPREPQVYTLPPSQEEMTKNQVSLTCLVKGFYPSD IAVEWESNGQPENNYKTTPPVLDSDGSFFLYSRLTVDKSRWQEGNVF SCSVMHEALHNHYTQKSLSLSLGK (SEQ ID NO: 52) |
| Anti-CD3 heavy chain VH F2B (+ silenced IgG4 Fc) | EVQLVESGGGLVQPGRSLRLSCAASGFTFDDYAMHWVRQAPGKGLE WVSGISWNSGSIGYADSVKGRFTISRDNAKNSLYLQMNSLRAEDTAL YYCAKDSRGYGDYRLGGAYWGQGTLVTVSSASTKGPSVFPLAPCSRS TSESTAALGCLVKDYFPEPVTVSWNSGALTSGVHTFPAVLQSSGLYSL SSVVTVPSSSLGTKTYTCNVDHKPSNTKVDKRVESKYGPPCPPCPAPE AAGGPSVFLFPPKPKDTLMISRTPEVTCVVVDVSQEDPEVQFNWYVD GVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPS DIAVEWESNGQPENNYKTTPPVLDSDGSFFLYSRLTVDKSRWQEGNV FSCSVMHEALHNHYTQKSLSLSLGK (SEQ ID NO: 53) |
| Silenced IgG4 (CH1 - hinge - CH2 - CH3; hole (S228P, F234A, L235A; T366S, L368A, Y407V)) | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVDK RVESKYGPPCPPCPAPEAAGGPSVFLFPPKPKDTLMISRTPEVTCVV VDVSQEDPEVQFNWYVDGVEVHNAKTKPREEQFNSTYRVVSVLTVL HQDWLNGKEYKCKVSNKGLPSSIEKTISKAKGQPREPQVYTLPPSQEE MTKNQVSLSCAVKGFYPSDIAVEWESNGQPENNYKTTPPVLDSDGS FFLVSRLTVDKSRWQEGNVFSCSVMHEALHNHYTQKSLSLSLGK (SEQ ID NO: 72) |
| Silenced IgG4 (CH1 - hinge - CH2 - CH3; knob (S228P, F234A, L235A; T366W)) | ASTKGPSVFPLAPCSRSTSESTAALGCLVKDYFPEPVTVSWNSGALTS GVHTFPAVLQSSGLYSLSSVVTVPSSSLGTKTYTCNVDHKPSNTKVDK RVESKYGPPCPPCPAPEAAGGPSVFLFPPKPKDTLMISRTPEVTCVV VDVSQEDPEVQFNWYVDGVEVHNAKTKPREEQFNSTYRVVSVLTVL HQDWLNGKEYKCKVSNKGLPSSIEKTISKAKGQPREPQVYTLPPSQEE MTKNQVSLWCLVKGFYPSDIAVEWESNGQPENNYKTTPPVLDSDGS FFLYSRLTVDKSRWQEGNVFSCSVMHEALHNHYTQKSLSLSLGK (SEQ ID NO: 73) |
| Silenced IgG4 (hinge - CH2 - CH3; hole (S228P, F234A, L235A; T366S, L368A, Y407V)) | ESKYGPPCPPCPAPEAAGGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPS QEEMT KNQVSLSCAVKGFYPSDIAVEWESNGQPENNYKTTPPVLDSDGSFFL VSRLTVDKSRWQEGNVFSCSVMHEALHNHYTQKSLSLSLGK (SEQ ID NO: 54) |
| Silenced IgG4 (hinge - CH2 - CH3; knob (S228P, F234A, L235A; T366W)) | ESKYGPPCPPCPAPEAAGGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMT KNQVSLWCLVKGFYPSDIAVEWESNGQPENNYKTTPPVLDSDGSFF LYSRLTVDKSRWQEGNVFSCSVMHEALHNHYTQKSLSLSLGK (SEQ ID NO: 55) |
| Anti-CD3 full length heavy chain (VH F2B + silenced IgG4 Fc + knob (S228P, F234A, L235A; T366W)) with C-terminal Lysine (K) | EVQLVESGGGLVQPGRSLRLSCAASGFTFDDYAMHWVRQAPGKGLE WVSGISWNSGSIGYADSVKGRFTISRDNAKNSLYLQMNSLRAEDTAL YYCAKDSRGYGDYRLGGAYWGQGTLVTVSSASTKGPSVFPLAPCSRS TSESTAALGCLVKDYFPEPVTVSWNSGALTSGVHTFPAVLQSSGLYSL SSVVTVPSSSLGTKTYTCNVDHKPSNTKVDKRVESKYGPPCPPCPAPE AAGGPSVFLFPPKPKDTLMISRTPEVTCVVVDVSQEDPEVQFNWYV DGVEVHNAKTKPREEQFNSTYRVVSVLTVLHQDWLNGKEYKCKVSN KGLPSSIEKTISKAKGQPREPQVYTLPPSQEEMTKNQVSLWCLVKGF YPSDIAVEWESNGQPENNYKTTPPVLDSDGSFFLYSRLTVDKSRWQE GNVFSCSVMHEALHNHYTQKSLSLSLGK (SEQ ID NO: 56) |

TABLE 6-continued

Anti-CD3 antibody sequences.

| | |
|---|---|
| Anti-CD3 full length heavy chain (VH F2B + silenced IgG4 Fc + knob (S228P, F234A, L235A; T366W)) without C-terminal Lysine (K) | EVQLVESGGGLVQPGRSLRLSCAASGFTFDDYAMHWVRQAPGKGLE WVSGISWNSGSIGYADSVKGRFTISRDNAKNSLYLQMNSLRAEDTAL YYCAKDSRGYGDYRLGGAYWGQGTLVTVSSASTKGPSVFPLAPCSRS TSESTAALGCLVKDYFPEPVTVSWNSGALTSGVHTFPAVLQSSGLYSL SSVVTVPSSSLGTKTYTCNVDHKPSNTKVDKRVESKYGPPCPPCPAPE AAGGPSVFLFPPKPKDTLMISRTPEVTCVVVDVSQEDPEVQFNWYV DGVEVHNAKTKPREEQFNSTYRVVSVLTVLHQDWLNGKEYKCKVSN KGLPSSIEKTISKAKGQPREPQVYTLPPSQEEMTKNQVSLWCLVKGF YPSDIAVEWESNGQPENNYKTTPPVLDSDGSFFLYSRLTVDKSRWQE GNVFSCSVMHEALHNHYTQKSLSLSLG (SEQ ID NO: 75) |
| Anti-CD3 full length heavy chain (VH F2B + silenced IgG4 Fc + hole (S228P, F234A, L235A; T365S L368A Y407V)) | EVQLVESGGGLVQPGRSLRLSCAASGFTFDDYAMHWVRQAPGKGLE WVSGISWNSGSIGYADSVKGRFTISRDNAKNSLYLQMNSLRAEDTAL YYCAKDSRGYGDYRLGGAYWGQGTLVTVSSASTKGPSVFPLAPCSRS TSESTAALGCLVKDYFPEPVTVSWNSGALTSGVHTFPAVLQSSGLYSL SSVVTVPSSSLGTKTYTCNVDHKPSNTKVDKRVESKYGPPCPPCPAPE AAGGPSVFLFPPKPKDTLMISRTPEVTCVVVDVSQEDPEVQFNWYV DGVEVHNAKTKPREEQFNSTYRVVSVLTVLHQDWLNGKEYKCKVSN KGLPSSIEKTISKAKGQPREPQVYTLPPSQEEMTKNQVSLSCAVKGFY PSDIAVEWESNGQPENNYKTTPPVLDSDGSFFLVSRLTVDKSRWQEG NVFSCSVMHEALHNHYTQKSLSLSLGK (SEQ ID NO: 57) |

TABLE 7

Anti-TAA antibody sequences.

| | |
|---|---|
| Silenced IgG4 (hinge - CH2 - CH3; hole (S228P, F234A, L235A; T365S, L368A, Y407V)) | ESKYGPPCPPCPAPEAAGGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMT KNQVSLSCAVKGFYPSDIAVEWESNGQPENNYKTTPPVLDSDGSFFL VSRLTVDKSRWQEGNVFSCSVMHEALHNHYTQKSLSLSLGK (SEQ ID NO: 54) |
| Silenced IgG4 (hinge - CH2 - CH3; knob (S228P, F234A, L235A; T366W)) | ESKYGPPCPPCPAPEAAGGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMT KNQVSLWCLVKGFYPSDIAVEWESNGQPENNYKTTPPVLDSDGSFF LYSRLTVDKSRWQEGNVFSCSVMHEALHNHYTQKSLSLSLGK (SEQ ID NO: 55) |
| BCMA bivalent heavy chain (TNB-383B w GS1) + silenced IgG4 Fc hinge CH2 CH3, hole (S228P, F234A, L235A, T366S, L368A, Y407V, with C-terminal Lysine (K) | EVQLLESGGGLVQPGGSLRLSCAASGFTVSSYGMSWVRQAPGKGPE WVSGIRGSDGSTYYADSVKGRFTISRDNSKNTLYLQMNSLRAEDTAV YYCAKQGENDGPFDHRGQGTLVTVSSGGGGSEVQLLESGGGLVQPG GSLRLSCAASGFTVSSYGMSWVRQAPGKGPEWVSGIRGSDGSTYYAD SVKGRFTISRDNSKNTLYLQMNSLRAEDTAVYYCAKQGENDGPFDHR GQGTLVTVSSESKYGPPCPPCPAPEAAGGPSVFLFPPKPKDTLMISR TPEVTCVVVDVSQEDPEVQFNWYVDGVEVHNAKTKPREEQFNSTYR VVSVLTVLHQDWLNGKEYKCKVSNKGLPSSIEKTISKAKGQPREPQV YTLPPSQEEMTKNQVSLSCAVKGFYPSDIAVEWESNGQPENNYKTTP PVLDSDGSFFLVSRLTVDKSRWQEGNVFSCSVMHEALHNHYTQKSL SLSLGK (SEQ ID NO: 58) |
| BCMA bivalent heavy chain (TNB-383B w GS1) + silenced IgG4 Fc hinge CH2 CH3, hole (S228P, F234A, L235A, T366S, L368A, Y407V, without C-terminal Lysine (K) | EVQLLESGGGLVQPGGSLRLSCAASGFTVSSYGMSWVRQAPGKGPE WVSGIRGSDGSTYYADSVKGRFTISRDNSKNTLYLQMNSLRAEDTAV YYCAKQGENDGPFDHRGQGTLVTVSSGGGGSEVQLLESGGGLVQPG GSLRLSCAASGFTVSSYGMSWVRQAPGKGPEWVSGIRGSDGSTYYAD SVKGRFTISRDNSKNTLYLQMNSLRAEDTAVYYCAKQGENDGPFDHR GQGTLVTVSSESKYGPPCPPCPAPEAAGGPSVFLFPPKPKDTLMISR TPEVTCVVVDVSQEDPEVQFNWYVDGVEVHNAKTKPREEQFNSTYR VVSVLTVLHQDWLNGKEYKCKVSNKGLPSSIEKTISKAKGQPREPQV YTLPPSQEEMTKNQVSLSCAVKGFYPSDIAVEWESNGQPENNYKTTP PVLDSDGSFFLVSRLTVDKSRWQEGNVFSCSVMHEALHNHYTQKSL SLSLG (SEQ ID NO: 76) |
| BCMA bivalent heavy chain (TNB-383B w GS2) + silenced IgG4 Fc hinge CH2 CH3, hole (S228P, F234A, L235A, T365S, | EVQLLESGGGLVQPGGSLRLSCAASGFTVSSYGMSWVRQAPGKGPE WVSGIRGSDGSTYYADSVKGRFTISRDNSKNTLYLQMNSLRAEDTAV YYCAKQGENDGPFDHRGQGTLVTVSSGGGGSGGGGSEVQLLESGGG LVQPGGSLRLSCAASGFTVSSYGMSWVRQAPGKGPEWVSGIRGSDGS TYYADSVKGRFTISRDNSKNTLYLQMNSLRAEDTAVYYCAKQGEND GPFDHRGQGTLVTVSSESKYGPPCPPCPAPEAAGGPSVFLFPPKPKD TLMISRTPEVTCVVVDVSQEDPEVQFNWYVDGVEVHNAKTKPREEQF |

TABLE 7-continued

Anti-TAA antibody sequences.

| | |
|---|---|
| L368A, Y407V, with C-terminal Lysine (K) | NSTYRVVSVLTVLHQDWLNGKEYKCKVSNKGLPSSIEKTISKAKGQP REPQVYTLPPSQEEMTKNQVSLSCAVKGFYPSDIAVEWESNGQPEN NYKTTPPVLDSDGSFFLVSRLTVDKSRWQEGNVFSCSVMHEALHNH YTQKSLSLSLGK (SEQ ID NO: 59) |
| BCMA bivalent heavy chain (TNB-383B w GS2) + silenced IgG4 Fc hinge CH2 CH3, hole (S228P, F234A, L235A, T366S, L368A, Y407V, without C-terminal Lysine (K) | EVQLLESGGGLVQPGGSLRLSCAASGFTVSSYGMSWVRQAPGKGPE WVSGIRGSDGSTYYADSVKGRFTISRDNSKNTLYLQMNSLRAEDTAV YYCAKQGENDGPFDHRGQGTLVTSSGGGGSGGGGSEVQLLESGGG LVQPGGSLRLSCAASGFTVSSYGMSWVRQAPGKGPEWVSGIRSDGS TYYADSVKGRFTISRDNSKNTLYLQMNSLRAEDTAVYYCAKQGEND GPFDHRGQGTLVTSSESKYGPPCPPCPAPEAAGGPSVFLFPPKPKD TLMISRTPEVTCVVVDVSQEDPEVQFNWYVDGVEVHNAKTKPREEQF NSTYRVVSVLTVLHQDWLNGKEYKCKVSNKGLPSSIEKTISKAKGQP REPQVYTLPPSQEEMTKNQVSLSCAVKGFYPSDIAVEWESNGQPEN NYKTTPPVLDSDGSFFLVSRLTVDKSRWQEGNVFSCSVMHEALHNH YTQKSLSLSLG (SEQ ID NO: 77) |
| BCMA monovalent heavy chain (TNB-383B) + silenced IgG4 Fc hinge CH2 CH3, hole (S228P, F234A, L235A, T366S, L368A, Y407V | EVQLLESGGGLVQPGGSLRLSCAASGFTVSSYGMSWVRQAPGKGPE WVSGIRGSDGSTYYADSVKGRFTISRDNSKNTLYLQMNSLRAEDTAV YYCAKQGENDGPFDHRGQGTLVTSSESKYGPPCPPCPAPEAAGGP SVFLFPPKPKDTLMISRTPEVTCVVVDVSQEDPEVQFNWYVDGVEVH NAKTKPREEQFNSTYRVVSVLTVLHQDWLNGKEYKCKVSNKGLPSSI EKTISKAKGQPREPQVYTLPPSQEEMTKNQVSLSCAVKGFYPSDIAV EWESNGQPENNYKTTPPVLDSDGSFFLVSRLTVDKSRWQEGNVFSCS VMHEALHNHYTQKSLSLSLGK (SEQ ID NO: 60) |
| PSMA monovalent heavy chain (clone ID 346181) + silenced IgG4 Fc hinge CH2 CH3, hole (S228P, F234A, L235A, T366S, L368A, Y407V, with C-terminal Lysine (K) | QLQLQESGPGLVKPSETLSLTCTVSGGSISSSNYFWGWIRQSPGKGLE WIGSIDYSGYTYYNPSLKSRVTISVDTSKNQFSLKLSSVTAADTAVYN CARHKAATADFDYRGQGTLVTSSESKYGPPCPPCPAPEAAGGPSV FLFPPKPKDTLMISRTPEVTCVVVDVSQEDPEVQFNWYVDGVEVHNA KTKPREEQFNSTYRVVSVLTVLHQDWLNGKEYKCKVSNKGLPSSIEK TISKAKGQPREPQVYTLPPSQEEMTKNQVSLSCAVKGFYPSDIAVEW ESNGQPENNYKTTPPVLDSDGSFFLVSRLTVDKSRWQEGNVFSCSVM HEALHNHYTQKSLSLSLGK (SEQ ID NO: 61) |
| PSMA monovalent heavy chain (clone ID 346181) + silenced IgG4 Fc hinge CH2 CH3, hole (S228P, F234A, L235A, T366S, L368A, Y407V, without C-terminal Lysine (K) | QLQLQESGPGLVKPSETLSLTCTVSGGSISSSNYFWGWIRQSPGKGLE WIGSIDYSGYTYYNPSLKSRVTISVDTSKNQFSLKLSSVTAADTAVYN CARHKAATADFDYRGQGTLVTSSESKYGPPCPPCPAPEAAGGPSV FLFPPKPKDTLMISRTPEVTCVVVDVSQEDPEVQFNWYVDGVEVHNA KTKPREEQFNSTYRVVSVLTVLHQDWLNGKEYKCKVSNKGLPSSIEK TISKAKGQPREPQVYTLPPSQEEMTKNQVSLSCAVKGFYPSDIAVEW ESNGQPENNYKTTPPVLDSDGSFFLVSRLTVDKSRWQEGNVFSCSVM HEALHNHYTQKSLSLSLG (SEQ ID NO: 81) |
| PSMA bivalent heavy chain (clone ID 346181) + silenced IgG4 Fc hinge CH2 CH3, hole (S228P, F234A, L235A, T366S, L368A, Y407V, with C-terminal Lysine (K) | QLQLQESGPGLVKPSETLSLTCTVSGGSISSSNYFWGWIRQSPGKGLE WIGSIDYSGYTYYNPSLKSRVTISVDTSKNQFSLKLSSVTAADTAVYN CARHKAATADFDYRGQGTLVTSSGGGGSGGGGSQLQLQESGPGLV KPSETLSLTCTVSGGSISSSNYFWGWIRQSPGKGLEWIGSIDYSGYTYY NPSLKSRVTISVDTSKNQFSLKLSSVTAADTAVYNCARHKAATADFD YRGQGTLVTSSESKYGPPCPPCPAPEAAGGPSVFLFPPKPKDTLMI SRTPEVTCVVVDVSQEDPEVQFNWYVDGVEVHNAKTKPREEQFNST YRVVSVLTVLHQDWLNGKEYKCKVSNKGLPSSIEKTISKAKGQPREP QVYTLPPSQEEMTKNQVSLSCAVKGFYPSDIAVEWESNGQPENNYK TTPPVLDSDGSFFLVSRLTVDKSRWQEGNVFSCSVMHEALHNHYTQ KSLSLSLGK (SEQ ID NO: 62) |
| PSMA bivalent heavy chain (clone ID 346181) + silenced IgG4 Fc hinge CH2 CH3, hole (S228P, F234A, L235A, T366S, L368A, Y407V, without C-terminal Lysine (K) | QLQLQESGPGLVKPSETLSLTCTVSGGSISSSNYFWGWIRQSPGKGLE WIGSIDYSGYTYYNPSLKSRVTISVDTSKNQFSLKLSSVTAADTAVYN CARHKAATADFDYRGQGTLVTSSGGGGSGGGGSQLQLQESGPGLV KPSETLSLTCTVSGGSISSSNYFWGWIRQSPGKGLEWIGSIDYSGYTYY NPSLKSRVTISVDTSKNQFSLKLSSVTAADTAVYNCARHKAATADFD YRGQGTLVTSSESKYGPPCPPCPAPEAAGGPSVFLFPPKPKDTLMI SRTPEVTCVVVDVSQEDPEVQFNWYVDGVEVHNAKTKPREEQFNST YRVVSVLTVLHQDWLNGKEYKCKVSNKGLPSSIEKTISKAKGQPREP QVYTLPPSQEEMTKNQVSLSCAVKGFYPSDIAVEWESNGQPENNYK TTPPVLDSDGSFFLVSRLTVDKSRWQEGNVFSCSVMHEALHNHYTQ KSLSLSLG (SEQ ID NO: 82) |
| PSMA monovalent heavy chain (clone ID 345497) + silenced IgG4 Fc hinge CH2 CH3, hole (S228P, F234A, | QVQLVESGGGVVQPGRSLRLSCAASGFSFSRYGMHWVRQAPGKGLE GVAVIWYDGSNRYYADSVKGRFTISRDNSKNTLYLQMNSLRAEDTA VYYCAREPRIGYYYESSGYYSLDYRGQGTLVTSSESKYGPPCPPCP APEAAGGPSVFLFPPKPKDTLMISRTPEVTCVVVDVSQEDPEVQFNW YVDGVEVHNAKTKPREEQFNSTYRVVSVLTVLHQDWLNGKEYKCK VSNKGLPSSIEKTISKAKGQPREPQVYTLPPSQEEMTKNQVSLSCAVK |

TABLE 7-continued

Anti-TAA antibody sequences.

| | |
|---|---|
| L235A, T366S, L368A, Y407V, with C-terminal Lysine (K) | GFYPSDIAVEWESNGQPENNYKTTPPVLDSDGSFFLVSRLTVDKSRW QEGNVFSCSVMHEALHNHYTQKSLSLSLGK (SEQ ID NO: 63) |
| PSMA monovalent heavy chain (clone ID 345497) + silenced IgG4 Fc hinge CH2 CH3, hole (S228P, F234A, L235A, T366S, L368A, Y407V, without C-terminal Lysine (K) | QVQLVESGGGVVQPGRSLRLSCAASGFSFSRYGMHWVRQAPGKGLE GVAVIWYDGSNRYYADSVKGRFTISRDNSKNTLYLQMNSLRAEDTA VYYCAREPRIGYYYESSGYYSLDYRGQGTLVTVSSESKYGPPCPPCP APEAAGGPSVFLFPPKPKDTLMISRTPEVTCVVVDVSQEDPEVQFNW YVDGVEVHNAKTKPREEQFNSTYRVVSVLTVLHQDWLNGKEYKCK VSNKGLPSSIEKTISKAKGQPREPQVYTLPPSQEEMTKNQVSLSCAVK GFYPSDIAVEWESNGQPENNYKTTPPVLDSDGSFFLVSRLTVDKSRW QEGNVFSCSVMHEALHNHYTQKSLSLSLG (SEQ ID NO: 83) |
| PSMA bivalent heavy chain (clone ID 345497) + silenced IgG4 Fc hinge CH CH3, hole (S228P, F234A, L235A, T366S, L368A, Y407V, with C-terminal Lysine (K) | QVQLVESGGGVVQPGRSLRLSCAASGFSFSRYGMHWVRQAPGKGLE GVAVIWYDGSNRYYADSVKGRFTISRDNSKNTLYLQMNSLRAEDTA VYYCAREPRIGYYYESSGYYSLDYRGQGTLVTVSSGGGGSGGGGSQV QLVESGGGVVQPGRSLRLSCAASGFSFSRYGMHWVRQAPGKGLEGV AVIWYDGSNRYYADSVKGRFTISRDNSKNTLYLQMNSLRAEDTAVY YCAREPRIGYYYESSGYYSLDYRGQGTLVTVSSESKYGPPCPPCPAPE AAGGPSVFLFPPKPKDTLMISRTPEVTCVVVDVSQEDPEVQFNWYV DGVEVHNAKTKPREEQFNSTYRVVSVLTVLHQDWLNGKEYKCKVSN KGLPSSIEKTISKAKGQPREPQVYTLPPSQEEMTKNQVSLSCAVKGFY PSDIAVEWESNGQPENNYKTTPPVLDSDGSFFLVSRLTVDKSRWQEG NVFSCSVMHEALHNHYTQKSLSLSLGK (SEQ ID NO: 64) |
| PSMA bivalent heavy chain (clone ID 345497) + silenced IgG4 Fc hinge CH CH3, hole (S228P, F234A, L235A, T366S, L368A, Y407V, without C-terminal Lysine (K) | QVQLVESGGGVVQPGRSLRLSCAASGFSFSRYGMHWVRQAPGKGLE GVAVIWYDGSNRYYADSVKGRFTISRDNSKNTLYLQMNSLRAEDTA VYYCAREPRIGYYYESSGYYSLDYRGQGTLVTVSSGGGGSGGGGSQV QLVESGGGVVQPGRSLRLSCAASGFSFSRYGMHWVRQAPGKGLEGV AVIWYDGSNRYYADSVKGRFTISRDNSKNTLYLQMNSLRAEDTAVY YCAREPRIGYYYESSGYYSLDYRGQGTLVTVSSESKYGPPCPPCPAPE AAGGPSVFLFPPKPKDTLMISRTPEVTCVVVDVSQEDPEVQFNWYV DGVEVHNAKTKPREEQFNSTYRVVSVLTVLHQDWLNGKEYKCKVSN KGLPSSIEKTISKAKGQPREPQVYTLPPSQEEMTKNQVSLSCAVKGFY PSDIAVEWESNGQPENNYKTTPPVLDSDGSFFLVSRLTVDKSRWQEG NVFSCSVMHEALHNHYTQKSLSLSLG (SEQ ID NO: 84) |
| PSMA bivalent heavy chain (clone ID 346181 x clone ID 345497) + silenced IgG4 Fc, hole (S228P, F234A, L235A, T366S, L368A, Y407V, with C-terminal Lysine (K) | QLQLQESGPGLVKPSETLSLTCTVSGGSISSSNYFWGWIRQSPGKGLE WIGSIDYSGYTYYNPSLKSRVTISVDTSKNQFSLKLSSVTAADTAVYN CARHKAATADFDYRGQGTLVTVSSGGGGSGGGGSQVQLVESGGGVV QPGRSLRLSCAASGFSFSRYGMHWVRQAPGKGLEGVAVIWYDGSNR YYADSVKGRFTISRDNSKNTLYLQMNSLRAEDTAVYYCAREPRIGYY YESSGYYSLDYRGQGTLVTVSSESKYGPPCPPCPAPEAAGGPSVFLF PPKPKDTLMISRTPEVTCVVVDVSQEDPEVQFNWYVDGVEVHNAKT KPREEQFNSTYRVVSVLTVLHQDWLNGKEYKCKVSNKGLPSSIEKTIS KAKGQPREPQVYTLPPSQEEMTKNQVSLSCAVKGFYPSDIAVEWES NGQPENNYKTTPPVLDSDGSFFLVSRLTVDKSRWQEGNVFSCSVMH EALHNHYTQKSLSLSLGK (SEQ ID NO: 65) |
| PSMA bivalent heavy chain (clone ID 346181 x clone ID 345497) + silenced IgG4 Fc, hole (S228P, F234A, L235A, T366S, L368A, Y407V, without C-terminal Lysine (K) | QLQLQESGPGLVKPSETLSLTCTVSGGSISSSNYFWGWIRQSPGKGLE WIGSIDYSGYTYYNPSLKSRVTISVDTSKNQFSLKLSSVTAADTAVYN CARHKAATADFDYRGQGTLVTVSSGGGGSGGGGSQVQLVESGGGVV QPGRSLRLSCAASGFSFSRYGMHWVRQAPGKGLEGVAVIWYDGSNR YYADSVKGRFTISRDNSKNTLYLQMNSLRAEDTAVYYCAREPRIGYY YESSGYYSLDYRGQGTLVTVSSESKYGPPCPPCPAPEAAGGPSVFLF PPKPKDTLMISRTPEVTCVVVDVSQEDPEVQFNWYVDGVEVHNAKT KPREEQFNSTYRVVSVLTVLHQDWLNGKEYKCKVSNKGLPSSIEKTIS KAKGQPREPQVYTLPPSQEEMTKNQVSLSCAVKGFYPSDIAVEWES NGQPENNYKTTPPVLDSDGSFFLVSRLTVDKSRWQEGNVFSCSVMH EALHNHYTQKSLSLSLG (SEQ ID NO: 85) |
| PSMA bivalent heavy chain (clone ID 345497 x clone ID 346181) + silenced IgG4 Fc, hole (S228P, F234A, L235A, T366S, L368A, Y407V, with C-terminal Lysine (K) | QVQLVESGGGVVQPGRSLRLSCAASGFSFSRYGMHWVRQAPGKGLE GVAVIWYDGSNRYYADSVKGRFTISRDNSKNTLYLQMNSLRAEDTA VYYCAREPRIGYYYESSGYYSLDYRGQGTLVTVSSGGGGSGGGGSQL QLQESGPGLVKPSETLSLTCTVSGGSISSSNYFWGWIRQSPGKGLEWIG SIDYSGYTYYNPSLKSRVTISVDTSKNQFSLKLSSVTAADTAVYNCAR HKAATADFDYRGQGTLVTVSSESKYGPPCPPCPAPEAAGGPSVFLF PPKPKDTLMISRTPEVTCVVVDVSQEDPEVQFNWYVDGVEVHNAKT KPREEQFNSTYRVVSVLTVLHQDWLNGKEYKCKVSNKGLPSSIEKTIS KAKGQPREPQVYTLPPSQEEMTKNQVSLSCAVKGFYPSDIAVEWES NGQPENNYKTTPPVLDSDGSFFLVSRLTVDKSRWQEGNVFSCSVMH EALHNHYTQKSLSLSLGK (SEQ ID NO: 66) |
| PSMA bivalent heavy chain (clone | QVQLVESGGGVVQPGRSLRLSCAASGFSFSRYGMHWVRQAPGKGLE GVAVIWYDGSNRYYADSVKGRFTISRDNSKNTLYLQMNSLRAEDTA |

TABLE 7-continued

Anti-TAA antibody sequences.

| | |
|---|---|
| ID 345497 x clone ID 346181) + silenced IgG4 Fc, hole (S228P, F234A, L235A, T366S, L368A, Y407V, without C-terminal Lysine (K) | VYYCAREPRIGYYYESSGYYSLDYRGQGTLVTVSSGGGGSGGGGSQL QLQESGPGLVKPSETLSLTCTVSGGSISSSNYFWGWIRQSPGKGLEWIG SIDYSGYTYYNPSLKSRVTISVDTSKNQFSLKLSSVTAADTAVYNCAR HKAATADFDYRGQGTLVTVSSESKYGPPCPPCPAPEAAGGPSVFLF PPKPKDTLMISRTPEVTCVVVDVSQEDPEVQFNWYVDGVEVHNAKT KPREEQFNSTYRVVSVLTVLHQDWLNGKEYKCKVSNKGLPSSIEKTIS KAKGQPREPQVYTLPPSQEEMTKNQVSLSCAVKGFYPSDIAVEWES NGQPENNYKTTPPVLDSDGSFFLVSRLTVDKSRWQEGNVFSCSVMH EALHNHYTQKSLSLSLG (SEQ ID NO: 86) |
| CD19 monovalent heavy chain + silenced IgG4 Fc hinge CH CH3, hole (S228P, F234A, L235A, T366S, L368A, Y407V, with C-terminal Lysine (K) | EVQLVESGGGLVQPGGSLRLSCAASGFSFSDFWMSWVRQAPGKGLE WVATISQAGSEKDYVDSVKGRFTISRDNAKKSLYLQMNSLRAEDTAV YYCASGVYSFDYRGQGTLVTVSSESKYGPPCPPCPAPEAAGGPSVF LFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLSCAVKGFYPSDIAVEWES NGQPENNYKTTPPVLDSDGSFFLVSRLTVDKSRWQEGNVFSCSVMH EALHNHYTQKSLSLSLGK (SEQ ID NO: 67) |
| CD19 monovalent heavy chain + silenced IgG4 Fc hinge CH CH3, hole (S228P, F234A, L235A, T366S, L368A, Y407V, without C-terminal Lysine (K) | EVQLVESGGGLVQPGGSLRLSCAASGFSFSDFWMSWVRQAPGKGLE WVATISQAGSEKDYVDSVKGRFTISRDNAKKSLYLQMNSLRAEDTAV YYCASGVYSFDYRGQGTLVTVSSESKYGPPCPPCPAPEAAGGPSVF LFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLSCAVKGFYPSDIAVEWES NGQPENNYKTTPPVLDSDGSFFLVSRLTVDKSRWQEGNVFSCSVMH EALHNHYTQKSLSLSLG (SEQ ID NO: 78) |
| CD19 bivalent GS1 heavy chain + silenced IgG4 Fc hinge CH CH3, hole (S228P, F234A, L235A, T366S, L368A, Y407V, with C-terminal Lysine (K) | EVQLVESGGGLVQPGGSLRLSCAASGFSFSDFWMSWVRQAPGKGLE WVATISQAGSEKDYVDSVKGRFTISRDNAKKSLYLQMNSLRAEDTAV YYCASGVYSFDYRGQGTLVTVSSGGGGSEVQLVESGGGLVQPGGSLR LSCAASGFSFSDFWMSWVRQAPGKGLEWVATISQAGSEKDYVDSVK GRFTISRDNAKKSLYLQMNSLRAEDTAVYYCASGVYSFDYRGQGTLV TVSSESKYGPPCPPCPAPEAAGGPSVFLFPPKPKDTLMISRTPEVTCV VVDVSQEDPEVQFNWYVDGVEVHNAKTKPREEQFNSTYRVVSVLTV LHQDWLNGKEYKCKVSNKGLPSSIEKTISKAKGQPREPQVYTLPPSQE EMTKNQVSLSCAVKGFYPSDIAVEWESNGQPENNYKTTPPVLDSDG SFFLVSRLTVDKSRWQEGNVFSCSVMHEALHNHYTQKSLSLSLGK (SEQ ID NO: 68) |
| CD19 bivalent GS1 heavy chain + silenced IgG4 Fc hinge CH CH3, hole (S228P, F234A, L235A, T366S, L368A, Y407V, without C-terminal Lysine (K) | EVQLVESGGGLVQPGGSLRLSCAASGFSFSDFWMSWVRQAPGKGLE WVATISQAGSEKDYVDSVKGRFTISRDNAKKSLYLQMNSLRAEDTAV YYCASGVYSFDYRGQGTLVTVSSGGGGSEVQLVESGGGLVQPGGSLR LSCAASGFSFSDFWMSWVRQAPGKGLEWVATISQAGSEKDYVDSVK GRFTISRDNAKKSLYLQMNSLRAEDTAVYYCASGVYSFDYRGQGTLV TVSSESKYGPPCPPCPAPEAAGGPSVFLFPPKPKDTLMISRTPEVTCV VVDVSQEDPEVQFNWYVDGVEVHNAKTKPREEQFNSTYRVVSVLTV LHQDWLNGKEYKCKVSNKGLPSSIEKTISKAKGQPREPQVYTLPPSQE EMTKNQVSLSCAVKGFYPSDIAVEWESNGQPENNYKTTPPVLDSDG SFFLVSRLTVDKSRWQEGNVFSCSVMHEALHNHYTQKSLSLSLG (SEQ ID NO: 79) |
| CD19 bivalent GS2 heavy chain + silenced IgG4 Fc hinge CH CH3, hole (S228P, F234A, L235A, T366S, L368A, Y407V, with C-terminal Lysine (K) | EVQLVESGGGLVQPGGSLRLSCAASGFSFSDFWMSWVRQAPGKGLE WVATISQAGSEKDYVDSVKGRFTISRDNAKKSLYLQMNSLRAEDTAV YYCASGVYSFDYRGQGTLVTVSSGGGGSGGGGSEVQLVESGGGLVQ PGGSLRLSCAASGFSFSDFWMSWVRQAPGKGLEWVATISQAGSEKDY VDSVKGRFTISRDNAKKSLYLQMNSLRAEDTAVYYCASGVYSFDYR GQGTLVTVSSESKYGPPCPPCPAPEAAGGPSVFLFPPKPKDTLMISR TPEVTCVVVDVSQEDPEVQFNWYVDGVEVHNAKTKPREEQFNSTYR VVSVLTVLHQDWLNGKEYKCKVSNKGLPSSIEKTISKAKGQPREPQV YTLPPSQEEMTKNQVSLSCAVKGFYPSDIAVEWESNGQPENNYKTTP PVLDSDGSFFLVSRLTVDKSRWQEGNVFSCSVMHEALHNHYTQKSL SLSLGK (SEQ ID NO: 69) |
| CD19 bivalent GS2 heavy chain + silenced IgG4 Fc hinge CH CH3, hole (S228P, F234A, L235A, T366S, L368A, Y407V, without C-terminal Lysine (K) | EVQLVESGGGLVQPGGSLRLSCAASGFSFSDFWMSWVRQAPGKGLE WVATISQAGSEKDYVDSVKGRFTISRDNAKKSLYLQMNSLRAEDTAV YYCASGVYSFDYRGQGTLVTVSSGGGGSGGGGSEVQLVESGGGLVQ PGGSLRLSCAASGFSFSDFWMSWVRQAPGKGLEWVATISQAGSEKDY VDSVKGRFTISRDNAKKSLYLQMNSLRAEDTAVYYCASGVYSFDYR GQGTLVTVSSESKYGPPCPPCPAPEAAGGPSVFLFPPKPKDTLMISR TPEVTCVVVDVSQEDPEVQFNWYVDGVEVHNAKTKPREEQFNSTYR VVSVLTVLHQDWLNGKEYKCKVSNKGLPSSIEKTISKAKGQPREPQV YTLPPSQEEMTKNQVSLSCAVKGFYPSDIAVEWESNGQPENNYKTTP PVLDSDGSFFLVSRLTVDKSRWQEGNVFSCSVMHEALHNHYTQKSL SLSLG (SEQ ID NO: 80) |

In some embodiments, bispecific or multi-specific antibodies are provided, which may have any of the configurations discussed herein, including, without limitation, a bispecific three-chain antibody like molecule. In some embodiments, a bispecific antibody can comprise at least one heavy chain variable region having binding specificity for BCMA, PSMA, or CD19, and at least one heavy chain variable region having binding specificity for a different protein, e.g., CD3. In some embodiments, a bispecific antibody can comprise a heavy chain/light chain pair that has binding specificity for a first antigen, and a heavy chain from a heavy chain-only antibody, comprising an Fc portion comprising CH2 and/or CH3 and/or CH4 domains, in the absence of a CH1 domain, and an antigen binding domain that binds an epitope of a second antigen or a different epitope of the first antigen, in a monovalent or bivalent configuration. In one particular embodiment, a bispecific antibody comprises a heavy chain/light chain pair that has binding specificity for an antigen on an effector cell (e.g., a CD3 protein on a T-cell), and a heavy chain from a heavy chain-only antibody comprising an antigen-binding domain that has binding specificity for BCMA, PSMA, or CD19, in a monovalent or bivalent configuration.

In some embodiments, where an antibody of the invention is a bispecific antibody, one arm of the antibody (one binding moiety, or one binding unit) is specific for human BCMA, human PSMA, or human CD19, while the other arm may be specific for target cells, tumor-associated antigens, targeting antigens, e.g., integrins, etc., pathogen antigens, checkpoint proteins, and the like. Target cells specifically include cancer cells, including, without limitation, cells from solid tumors, e.g., prostate tumors, as discussed below. In some embodiments, one arm of the antibody (one binding moiety, or one binding unit) is specific for human BCMA, human PSMA, or human CD19, while the other arm is specific for CD3.

In some embodiments, an antibody comprises an anti-CD3 light chain polypeptide comprising the sequence of SEQ ID NO: 43 linked to the sequence of SEQ ID NO: 48, an anti-CD3 heavy chain polypeptide comprising the sequence of any one of SEQ ID NOs: 44, 45, 46, 47, 50, 51, 52, 53, 56 or 57, and an anti-BCMA heavy chain polypeptide comprising the sequence of any one of SEQ ID NOs: 58, 59 or 60. In one preferred embodiment, an antibody is a TCA comprising a first polypeptide comprising SEQ ID NO: 49, a second polypeptide comprising SEQ ID NO: 56, and a third polypeptide comprising SEQ ID NO: 58, 59 or 60. In one preferred embodiment, an antibody is a TCA comprising a first polypeptide comprising SEQ ID NO: 49, a second polypeptide comprising SEQ ID NO: 56, and a third polypeptide comprising SEQ ID NO: 58. In one preferred embodiment, an antibody is a TCA consisting of a first polypeptide consisting of SEQ ID NO: 49, a second polypeptide consisting of SEQ ID NO: 56, and a third polypeptide consisting of SEQ ID NO: 58. In one preferred embodiment, an antibody is a TCA comprising a first polypeptide comprising SEQ ID NO: 49, a second polypeptide comprising SEQ ID NO: 56, and a third polypeptide comprising SEQ ID NO: 59. In one preferred embodiment, an antibody is a TCA consisting of a first polypeptide consisting of SEQ ID NO: 49, a second polypeptide consisting of SEQ ID NO: 56, and a third polypeptide consisting of SEQ ID NO: 59. In one preferred embodiment, an antibody is a TCA comprising a first polypeptide comprising SEQ ID NO: 49, a second polypeptide comprising SEQ ID NO: 56, and a third polypeptide comprising SEQ ID NO: 60. In one preferred embodiment, an antibody is a TCA consisting of a first polypeptide consisting of SEQ ID NO: 49, a second polypeptide consisting of SEQ ID NO: 56, and a third polypeptide consisting of SEQ ID NO: 60.

In some embodiments, an antibody comprises an anti-CD3 light chain polypeptide comprising the sequence of SEQ ID NO: 43 linked to the sequence of SEQ ID NO: 48, an anti-CD3 heavy chain polypeptide comprising the sequence of any one of SEQ ID NOs: 44, 45, 46, 47, 50, 51, 52, 53, 56 or 57, and an anti-PSMA heavy chain polypeptide comprising the sequence of any one of SEQ ID NOs: 61, 62, 63, 64, 65 or 66. In one preferred embodiment, an antibody is a TCA comprising a first polypeptide comprising SEQ ID NO: 49, a second polypeptide comprising SEQ ID NO: 56, and a third polypeptide comprising SEQ ID NO: 61. In one preferred embodiment, an antibody is a TCA consisting of a first polypeptide consisting of SEQ ID NO: 49, a second polypeptide consisting of SEQ ID NO: 56, and a third polypeptide consisting of SEQ ID NO: 61. In one preferred embodiment, an antibody is a TCA comprising a first polypeptide comprising SEQ ID NO: 49, a second polypeptide comprising SEQ ID NO: 56, and a third polypeptide comprising SEQ ID NO: 62. In one preferred embodiment, an antibody is a TCA consisting of a first polypeptide consisting of SEQ ID NO: 49, a second polypeptide consisting of SEQ ID NO: 56, and a third polypeptide consisting of SEQ ID NO: 62. In one preferred embodiment, an antibody is a TCA comprising a first polypeptide comprising SEQ ID NO: 49, a second polypeptide comprising SEQ ID NO: 56, and a third polypeptide comprising SEQ ID NO: 63. In one preferred embodiment, an antibody is a TCA consisting of a first polypeptide consisting of SEQ ID NO: 49, a second polypeptide consisting of SEQ ID NO: 56, and a third polypeptide consisting of SEQ ID NO: 63. In one preferred embodiment, an antibody is a TCA comprising a first polypeptide comprising SEQ ID NO: 49, a second polypeptide comprising SEQ ID NO: 56, and a third polypeptide comprising SEQ ID NO: 64. In one preferred embodiment, an antibody is a TCA consisting of a first polypeptide consisting of SEQ ID NO: 49, a second polypeptide consisting of SEQ ID NO: 56, and a third polypeptide consisting of SEQ ID NO: 64. In one preferred embodiment, an antibody is a TCA comprising a first polypeptide comprising SEQ ID NO: 49, a second polypeptide comprising SEQ ID NO: 56, and a third polypeptide comprising SEQ ID NO: 65. In one preferred embodiment, an antibody is a TCA consisting of a first polypeptide consisting of SEQ ID NO: 49, a second polypeptide consisting of SEQ ID NO: 56, and a third polypeptide consisting of SEQ ID NO: 65. In one preferred embodiment, an antibody is a TCA comprising a first polypeptide comprising SEQ ID NO: 49, a second polypeptide comprising SEQ ID NO: 56, and a third polypeptide comprising SEQ ID NO: 66. In one preferred embodiment, an antibody is a TCA consisting of a first polypeptide consisting of SEQ ID NO: 49, a second polypeptide consisting of SEQ ID NO: 56, and a third polypeptide consisting of SEQ ID NO: 66.

In some embodiments, an antibody comprises an anti-CD3 light chain polypeptide comprising the sequence of SEQ ID NO: 43 linked to the sequence of SEQ ID NO: 48, an anti-CD3 heavy chain polypeptide comprising the sequence of any one of SEQ ID NOs: 44, 45, 46, 47, 50, 51, 52, 53, 56 or 57, and an anti-CD19 heavy chain polypeptide comprising the sequence of any one of SEQ ID NOs: 67, 68 or 69. In one preferred embodiment, an antibody is a TCA comprising a first polypeptide comprising SEQ ID NO: 49, a second polypeptide comprising SEQ ID NO: 56, and a third polypeptide comprising SEQ ID NO: 67. In one preferred embodiment, an antibody is a TCA consisting of a first polypeptide consisting of SEQ ID NO: 49, a second polypeptide consisting of SEQ ID NO: 56, and a third polypeptide consisting of SEQ ID NO: 67. In one preferred embodiment, an antibody is a TCA comprising a first polypeptide comprising SEQ ID NO: 49, a second polypeptide comprising SEQ ID NO: 56, and a third polypeptide comprising SEQ ID NO: 68. In one preferred embodiment, an antibody is a TCA consisting of a first polypeptide consisting of SEQ ID NO: 49, a second polypeptide consisting of SEQ ID NO: 56, and a third polypeptide consisting of SEQ ID NO: 68. In one preferred embodiment, an antibody is a TCA comprising a first polypeptide comprising SEQ ID NO: 49, a second polypeptide comprising SEQ ID NO: 56, and a third polypeptide comprising SEQ ID NO: 69. In one preferred embodiment, an antibody is a TCA consisting of a first polypeptide consisting of SEQ ID NO: 49, a second polypeptide consisting of SEQ ID NO: 56, and a third polypeptide consisting of SEQ ID NO: 69.

Various formats of multi-specific antibodies are within the ambit of the invention, including, without limitation, single chain polypeptides, two chain polypeptides, three chain polypeptides, four chain polypeptides, and multiples thereof. The multi-specific antibodies herein specifically include T-cell multi-specific (e.g., bispecific) antibodies binding to BCMA, PSMA, or 19, and CD3 (anti-BCMA×anti-CD3 antibodies, anti-PSMA×anti-CD3 antibodies, anti-CD19× anti-CD3 antibodies), and which contain a variant human IgG4 Fc domain comprising a first heavy chain constant region sequence comprising an S228P mutation, an F234A mutation, an L235A mutation, and a T366W mutation (knob), and a second heavy chain constant region sequence comprising an S228P mutation, an F234A mutation, an L235A mutation, a T366S mutation, an L368A mutation, and a Y407V mutation (hole). This variant, or modified, IgG4 Fc domain prevents unwanted Fab exchange, reduces effector function of the antibody, and also facilitates heterodimerization of the heavy chain polypeptide subunits to form the bispecific antibody. Such antibodies induce potent T-cell mediated killing of cells expressing BCMA, PSMA, or CD19, respectively.

Preparation of Antibodies

The multispecific antibodies of the present invention can be prepared by methods known in the art. In a preferred embodiment, the heavy chain antibodies herein are produced by transgenic animals, including transgenic mice and rats, preferably rats, in which the endogenous immunoglobulin genes are knocked out or disabled. In a preferred embodiment, the heavy chain antibodies herein are produced in UniRat™ UniRat™ have their endogenous immunoglobulin genes silenced and use a human immunoglobulin heavy-chain translocus to express a diverse, naturally optimized repertoire of fully human HCAbs. While endogenous immunoglobulin loci in rats can be knocked out or silenced using a variety of technologies, in UniRat™ the zinc-finger (endo) nuclease (ZNF) technology was used to inactivate the endogenous rat heavy chain J-locus, light chain Cκ locus and light chain Cλ locus. ZNF constructs for microinjection into oocytes can produce IgH and IgL knock out (KO) lines. For details see, e.g., Geurts et al., 2009, Science 325:433. Characterization of Ig heavy chain knockout rats has been reported by Menoret et al., 2010, Eur. J. Immunol. 40:2932-2941. Advantages of the ZNF technology are that non-homologous end joining to silence a gene or locus via deletions up to several kb can also provide a target site for homologous integration (Cui et al., 2011, Nat Biotechnol 29:64-67). Human heavy chain antibodies produced in Uni-Rat™ are called UniAbs™ and can bind epitopes that cannot be attacked with conventional antibodies. Their high specificity, affinity, and small size make them ideal for mono- and poly-specific applications.

In addition to UniAbs™, specifically included herein are heavy chain-only antibodies lacking the camelid VHH framework and mutations, and their functional VH regions. Such heavy chain-only antibodies can, for example, be produced in transgenic rats or mice which comprise fully human heavy chain-only gene loci as described, e.g., in WO2006/008548, but other transgenic mammals, such as rabbit, guinea pig, rat can also be used, rats and mice being preferred. Heavy chain-only antibodies, including their VHH or VH functional fragments, can also be produced by recombinant DNA technology, by expression of the encoding nucleic acid in a suitable eukaryotic or prokaryotic host, including, for example, mammalian cells (e.g., CHO cells), E. coli or yeast.

Domains of heavy chain-only antibodies combine advantages of antibodies and small molecule drugs: can be mono- or multi-valent; have low toxicity; and are cost-effective to manufacture. Due to their small size, these domains are easy to administer, including oral or topical administration, are characterized by high stability, including gastrointestinal stability; and their half-life can be tailored to the desired use or indication. In addition, VH and VHH domains of HCAbs can be manufactured in a cost effective manner.

In a particular embodiment, the heavy chain antibodies of the present invention, including UniAbs™, have the native amino acid residue at the first position of the FR4 region (amino acid position 101 according to the Kabat numbering system), substituted by another amino acid residue, which is capable of disrupting a surface-exposed hydrophobic patch comprising or associated with the native amino acid residue at that position. Such hydrophobic patches are normally buried in the interface with the antibody light chain constant region but become surface exposed in HCAbs and are, at least partially, for the unwanted aggregation and light chain association of HCAbs. The substituted amino acid residue preferably is charged, and more preferably is positively charged, such as lysine (Lys, K), arginine (Arg, R) or histidine (His, H), preferably arginine (R). In a preferred embodiment the heavy chain-only antibodies derived from the transgenic animals contain a Trp to Arg mutation at position 101. The resultant HCAbs preferably have high antigen-binding affinity and solubility under physiological conditions in the absence of aggregation.

As part of the present invention, human heavy chain antibodies with unique sequences from UniRat™ animals (UniAb™) were identified that bind human CD3, BCMA, PSMA, or CD19 in ELISA protein and cell-binding assays. The identified heavy chain variable region (VH) sequences (see, e.g., Tables 1 and 2) are positive for protein binding and/or for binding to cells expressing the target protein (e.g., CD3, BCMA, PSMA, or CD19), and are all negative for binding to cells that do not express the target protein.

Heavy chain antibodies binding to non-overlapping epitopes on a target protein, e.g., UniAbs™ can be identified by competition binding assays, such as enzyme-linked immunoassays (ELISA assays) or flow cytometric competitive binding assays. For example, one can use competition between known antibodies binding to the target antigen and the antibody of interest. By using this approach, one can divide a set of antibodies into those that compete with the reference antibody and those that do not. The non-competing antibodies are identified as binding to a distinct epitope that does not overlap with the epitope bound by the reference antibody. Often, one antibody is immobilized, the antigen is bound, and a second, labeled (e.g., biotinylated) antibody is tested in an ELISA assay for ability to bind the captured antigen. This can be performed also by using surface plasmon resonance (SPR) platforms, including ProteOn XPR36 (BioRad, Inc), Biacore 2000 and Biacore T200 (GE Healthcare Life Sciences), and MX96 SPR imager (Ibis technologies B.V.), as well as on biolayer interferometry platforms, such as Octet Red384 and Octet HTX (ForteBio, Pall Inc). For further details see the examples herein.

Typically, an antibody "competes" with a reference antibody if it causes about 15-100% reduction in the binding of the reference antibody to the target antigen, as determined by standard techniques, such as by the competition binding assays described above. In various embodiments, the relative inhibition is at least about 15%, at least about 20%, at least about 25%, at least about 30%, at least about 35%, at least about 40%, at least about 45%, at least about 50% at least about 55%, at least about 60%, at least about 65%, at least about 70%, at least about 75%, at least about 80%, at least about 85%, at least about 90%, at least about 95% or higher.

Pharmaceutical Compositions, Uses and Methods of Treatment

It is another aspect of the present invention to provide pharmaceutical compositions comprising one or more multispecific binding compounds of the present invention in admixture with a suitable pharmaceutically acceptable carrier. Pharmaceutically acceptable carriers as used herein are exemplified, but not limited to, adjuvants, solid carriers, water, buffers, or other carriers used in the art to hold therapeutic components, or combinations thereof.

In one embodiment, a pharmaceutical composition comprises a heavy chain antibody (e.g., UniAb™) that binds to a target protein (e.g., CD3, BCMA, PSMA, or CD19). In another embodiment, a pharmaceutical composition comprises a multi-specific (including bispecific) heavy chain antibody (e.g., UniAb™) with binding specificity for two or more non-overlapping epitopes on a target protein (e.g., CD3, BCMA, PSMA, or CD19). In a preferred embodiment, a pharmaceutical composition comprises a multi-specific (including bispecific) heavy chain antibody (e.g., UniAb™) with binding specificity to a target protein (e.g., BCMA, PSMA, or CD19) and with binding specificity to a binding target on an effector cell (e.g., a binding target on a T-cell, such as, e.g., a CD3 protein on a T-cell).

Pharmaceutical compositions of the antibodies used in accordance with the present invention are prepared for storage by mixing proteins having the desired degree of purity with optional pharmaceutically acceptable carriers, excipients or stabilizers (see, e.g. Remington's Pharmaceutical Sciences 16th edition, Osol, A. Ed. (1980)), such as in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Pharmaceutical compositions for parenteral administration are preferably sterile and substantially isotonic and manufactured under Good Manufacturing Practice (GMP) conditions. Pharmaceutical compositions can be provided in unit dosage form (i.e., the dosage for a single administration). The formulation depends on the route of administration chosen. The antibodies herein can be administered by intravenous injection or infusion or subcutaneously. For injection administration, the antibodies herein can be formulated in aqueous solutions, preferably in physiologically-compatible buffers to reduce discomfort at the site of injection. The solution can contain carriers, excipients, or stabilizers as discussed above. Alternatively, antibodies can be in lyophilized form for constitution with a suitable vehicle, e.g., sterile pyrogen-free water, before use.

Antibody formulations are disclosed, for example, in U.S. Pat. No. 9,034,324. Similar formulations can be used for the heavy chain antibodies, including UniAbs™, of the present invention. Subcutaneous antibody formulations are described, for example, in US20160355591 and US20160166689.

Methods of Use

The heavy chain-only antibodies, multi-specific antibodies, and pharmaceutical compositions described herein can be used for the treatment of diseases and conditions characterized by the expression of a target protein (e.g., CD3, BCMA, PSMA, or CD19), including, without limitation, the conditions and diseases described further herein.

The pharmaceutical compositions herein comprising anti-BCMA antibodies can be used for the treatment of B-cell related disorders, including B-cell and plasma cell malignancies and autoimmune disorders characterized by the expression or overexpression of BCMA.

Such B-cell related disorders include B-cell and plasma cell malignancies and autoimmune disorders, including, without limitation, plasmacytoma, Hodgkins' lymphoma, follicular lymphomas, small non-cleaved cell lymphomas, endemic Burkitt's lymphoma, sporadic Burkitt's lymphoma, marginal zone lymphoma, extranodal mucosa-associated lymphoid tissue lymphoma, nodal monocytoid B-cell lymphoma, splenic lymphoma, mantle cell lymphoma, large cell lymphoma, diffuse mixed cell lymphoma, immunoblastic lymphoma, primary mediastinal B-cell lymphoma, pulmonary B-cell angiocentric lymphoma, small lymphocytic lymphoma, B-cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, or monoclonal gammopathy.

The plasma cell disorders characterized by the expression of BCMA include Multiple Myeloma (MM). MM is a B-cell malignancy characterized by a monoclonal expansion and accumulation of abnormal plasma cells in the bone marrow compartment. Current therapies for MM often cause remissions, but nearly all patients eventually relapse and die. There is substantial evidence of an immune-mediated elimination of myeloma cells in the setting of allogeneic hematopoietic stem cell transplantation; however, the toxicity of this approach is high, and few patients are cured. Although some monoclonal antibodies have shown promise for treating MM in preclinical studies and early clinical trials, consistent clinical efficacy of any monoclonal antibody therapy for MM has not been conclusively demonstrated. There is therefore a great need for new therapies, including immunotherapies for MM (see, e.g., Carpenter et al., Clin Cancer Res 2013, 19(8):2048-2060).

Overexpression or activation of BCMA by its proliferation-inducing ligand, APRIL it known to promote human Multiple Myeloma (MM) progression in vivo. BCMA has also been shown to promote in vivo growth of xenografted MM cells harboring p53 mutation in mice. Since activity of the APRIL/BCMA pathway plays a central role in MM pathogenesis and drug resistance via bidirectional interactions between tumor cells and their supporting bone marrow microenvironment, BCMA has been identified as a target for the treatment of MM. For further details see, e.g., Yu-Tsu Tai et al., Blood 2016; 127(25):3225-3236.

Another B-cell disorder involving plasma cells i.e. expressing BCMA is systemic lupus erythematosus (SLE), also known as lupus. SLE is a systemic, autoimmune disease that can affect any part of the body and is represented with the immune system attacking the body's own cells and tissue, resulting in chronic inflammation and tissue damage. It is a Type III hypersensitivity reaction in which antibody-immune complexes precipitate and cause a further immune response (Inaki & Lee, Nat Rev Rheumatol 2010; 6: 326-337).

The anti-BCMA heavy chain-only antibodies (UniAb) of the present invention can be used to develop therapeutic agents for the treatment of MM, SLE, and other B-cell disorders or plasma cell disorders characterized by the expression of BCMA, such as those listed above. In particular, the anti-BCMA heavy chain-only antibodies (UniAb) of the present invention are candidates for the treatment of MM, alone or in combination with other MM treatments.

PSMA is a type II transmembrane protein that is expressed on prostate epithelium tissue and is upregulated in prostate cancer and the neovasculature of solid tumors. It is also expressed at low levels in healthy tissues such as the brain, kidney, and salivary glands but its overexpression in malignant prostate tissue makes it an attractive target for the therapeutic treatment of prostate cancer. It may also be relevant for therapy or imaging of solid tumors, given its high expression in malignant neovasculature. Monoclonal antibodies, antibody drug conjugates and chimeric antigen receptor T-cells targeting PSMA have been described for treatment of metastatic prostate cancer (Hernandez-Hoyos et al., 2016, PMID: 27406985, DiPippo et al., 2014, PMID: 25327986, Serganova et al., 2016, PMID: 28345023). In addition, radionuclide conjugates specific to PSMA are being investigated for imaging and treatment of prostate cancer (e.g., Hofman et al., 2018 PMID: 29752180).

In one aspect, the PSMA heavy chain antibodies (e.g., UniAbs™) and pharmaceutical compositions herein can be used to treat disorders characterized by the expression of PSMA, including, without limitation, prostate cancer and solid tumors.

CD19 is a cell surface receptor that is expressed on all human B-cells, but is not found on plasma cells. It has a relatively large, 240 amino acid, cytoplasmic tail. The extracellular Ig-like domains are divided by a potential disulfide linked non-Ig-like domain and N-linked carbohydrate addition sites. The cytoplasmic tail contains at least nine tyrosine residues near the C-terminus, some of which have been shown to be phosphorylated. Along with CD20 and CD22, the restricted expression of CD19 to the B-cell lineage makes it an attractive target for the therapeutic treatment of B-cell malignancies. Due to its observed expression in a number of hematological malignancies, CD19 is a promising target for antibody-based therapeutics.

In one aspect, the CD19 heavy chain antibodies (e.g., UniAbs™) and pharmaceutical compositions herein can be used to treat hematological malignancies characterized by the expression of CD19, including, without limitation, diffuse large B-cell lymphoma (DLBCL), non-Hodgkin's lymphoma, B-cell chronic lymphocylic leukemia (CLL), and B-cell acute lymphoblastic leukemia (ALL).

Diffuse large B-cell lymphoma (DLBCL or DLBL) is the most common form of non-Hodgkin's lymphoma among adults (Blood 1997 89 (11): 3909-18), with an estimated annual incidence of 7 to 8 cases per 100,000 people per year in the US and the UK. It is characterized as an aggressive cancer that can arise in virtually any part of the body. The causes of DLBCL are not well understood, and it can arise from normal B-cells as well as malignant transformation of other types of lymphoma or leukemia cells. Treatment approaches generally involve chemotherapy and radiation, and have resulted in an overall five-year survival rate average of approximately 58% for adults. Although some monoclonal antibodies have shown promise for treating DLBCL, consistent clinical efficacy has not yet been conclusively demonstrated. There is therefore a great need for new therapies, including immunotherapies, for DLBCL.

In another aspect, the CD19 heavy chain antibodies (e.g., UniAbs™) and pharmaceutical compositions herein can be used to treat autoimmune disorders characterized by pathogenic B-cells that express CD19, including, without limitation, systemic lupus erythematosus (SLE), rheumatoid arthritis (RA), and multiple sclerosis (MS).

Effective doses of the compositions of the present invention for the treatment of disease vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g., companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subject's response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage the agent may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months.

Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

Typically, compositions are prepared as injectables, either as liquid solutions or suspensions; solid forms suitable for solution in, or suspension in, liquid vehicles prior to injection can also be prepared. The pharmaceutical compositions herein are suitable for intravenous or subcutaneous administration, directly or after reconstitution of solid (e.g., lyophilized) compositions. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the antibodies and antibody structures described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in humans. The dosage of the antibodies described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The compositions for administration will commonly comprise an antibody or other agent (e.g., another ablative agent) dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents and formulations thereof, of the invention and instructions for use. The kit can further contain a least one additional reagent, e.g., a chemotherapeutic drug, etc. Kits typically include a label indicating the intended use of the contents of the kit. The term "label" as used herein includes any writing, or recorded material supplied on or with a kit, or which otherwise accompanies a kit.

The invention now being fully described, it will be apparent to one of ordinary skill in the art that various changes and modifications can be made without departing from the spirit or scope of the invention.

EXAMPLES

Example 1: Heterodimer Formation

Heterodimer formation was analyzed by non-reducing and reducing SDS-PAGE analyses to determine whether antibodies in accordance with embodiments of the invention, comprising various mutations in their hinge and Fc regions, as well as knobs-in-holes mutations, could be successfully expressed and assembled into desired heterodimer combinations. To test this, antibody constructs were expressed in recombinant CHO cell cultures. Harvested cell culture fluid was then purified via protein A affinity chromatography to analyze the different antibody fragments produced. The Protein A elution pools were then analyzed on reducing and non-reducing gels to visualize the different species.

Figure 2:
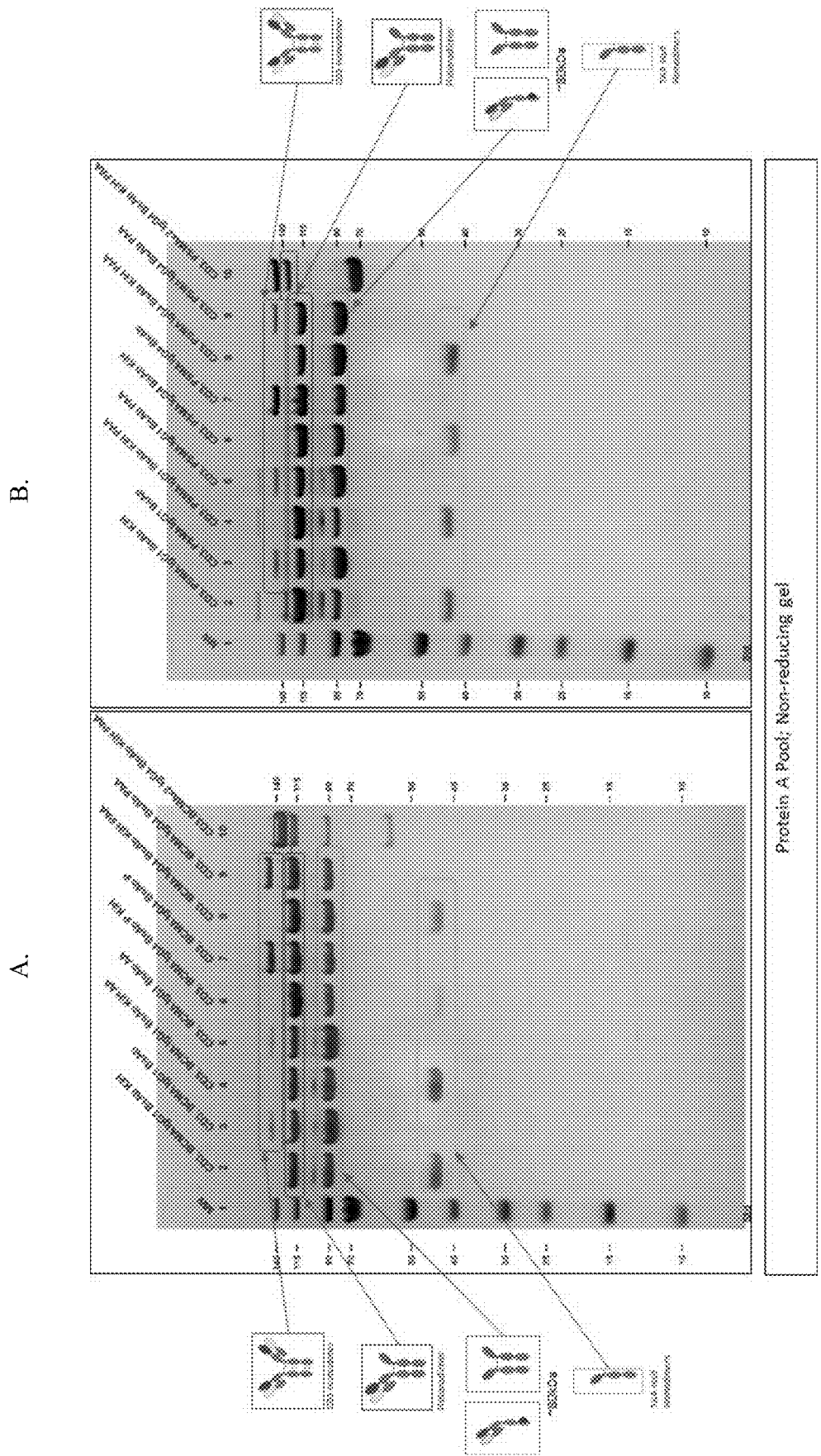
FIG. 2, panels A-B, show images of non-reducing SDS-PAGE analyses of various antibody species purified via protein A chromatography.
Figure 3:
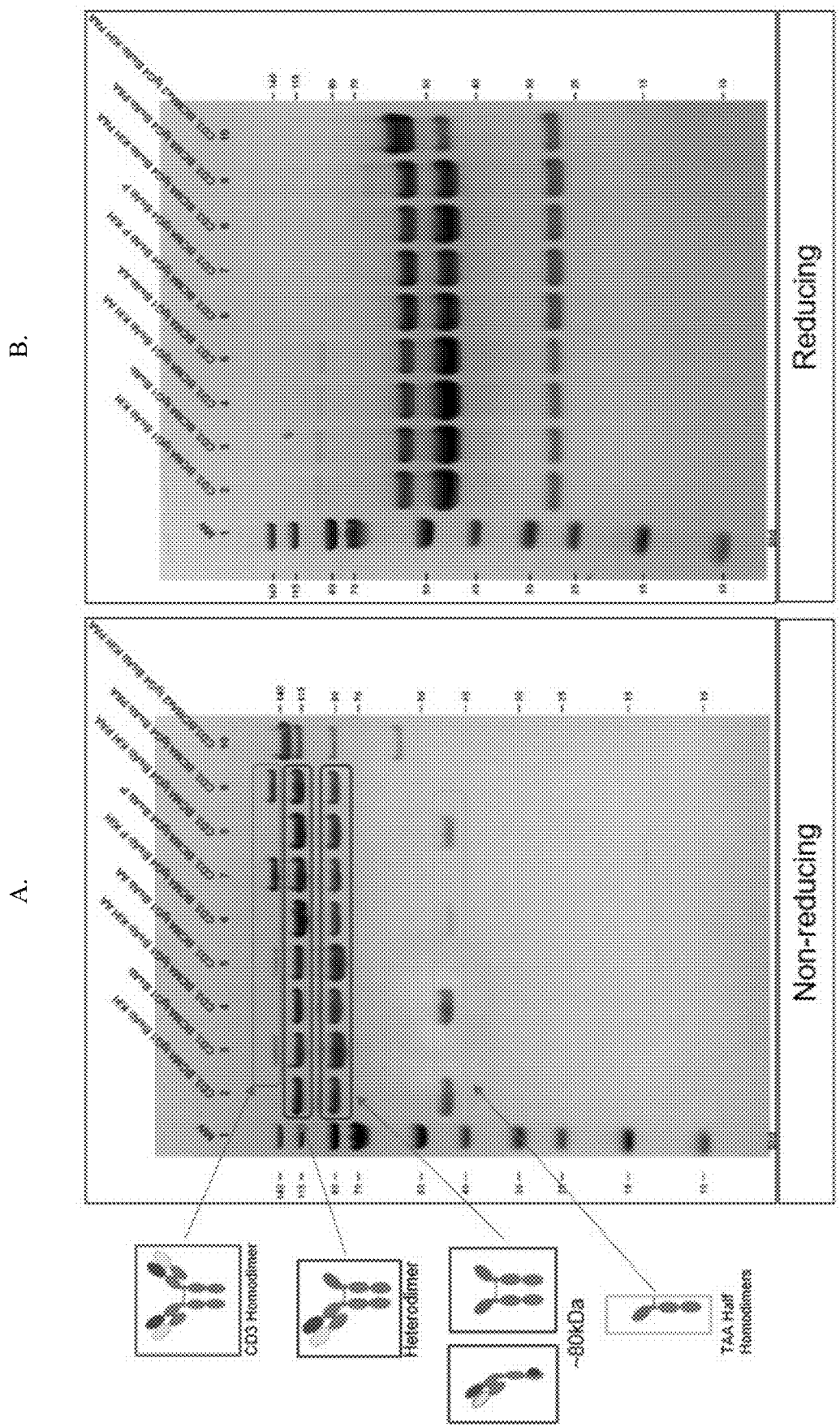
FIG. 3, panel A, shows an image of non-reducing SDS-PAGE analysis of various antibody species purified via protein A chromatography. Panel B shows an image of a reducing SDS-PAGE analysis of the same antibody species shown in panel A.
Figure 24:
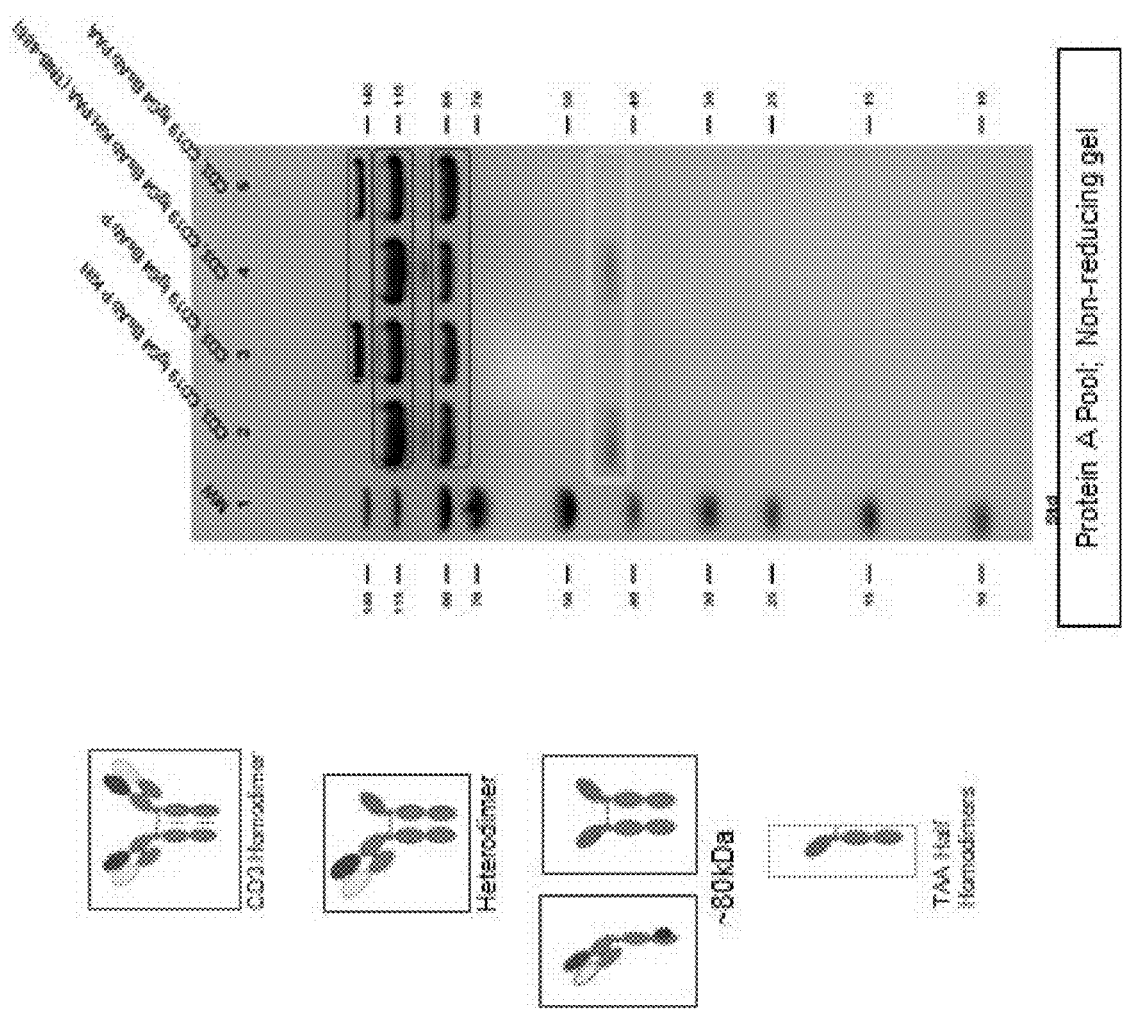
FIG. 24 is an image of a non-reducing SDS-PAGE analysis of various antibody species purified via protein A chromatography.

The results of these analyses are shown in FIG. 2, panels A and B, in FIG. 3, panels A and B, and in FIG. 24, and demonstrate that the percentage of heterodimer formation for the antibody species that include knobs-in-holes mutations is superior, even when effector function silencing mutations (F234A, L235A) and Fab arm exchange-preventing mutations (S228P) are also present in the heavy chain sequences. As provided in FIG. 25, purified CD19 constructs were evaluated to analyze the percentage of high molecular weight (HMW) and low molecular weight (LMW) species, as well as the percentage of monomers.

Example 2: Fc Gamma Receptor Binding by Biolayer Interferometry (BLI)

Fc gamma receptor-IgG interactions were analyzed on the Octet platform using an Ni-NTA biosensor (ForteBio). Ni-NTA biosensors have QIAGEN's Tris-NTA charged with nickel (Ni2+) pre-immobilized onto the tip. Ni-NTA will bind to a HIS-tag attached to recombinant proteins. In this format, the Fc gamma receptor protein is loaded onto the biosensor as the ligand, followed by association with IgG. Antibodies in accordance with embodiments of the invention were investigated to analyze the extent of interactions between their Fc regions and the Fc gamma receptor proteins immobilized on the biosensor.

Here, the Fc gamma receptor was human Fc gamma receptor I/CD64 (Acro Biosystems). Antibody concentrations tested included a 2× serial dilution from 100 nM to 1.6 nM. The results of these studies are shown in FIG. 4, panels A-D, FIG. 5, panels A-E, FIG. 6, panels A-D, FIG. 7, panels A-E, and FIG. 26, panels A-D, and demonstrate that binding of the silenced Fc receptor antibodies to human Fc gamma R1 is suppressed significantly, even when knobs-in-holes mutations and Fab arm exchange mutations are also present in the Fc region.

Figure 4:
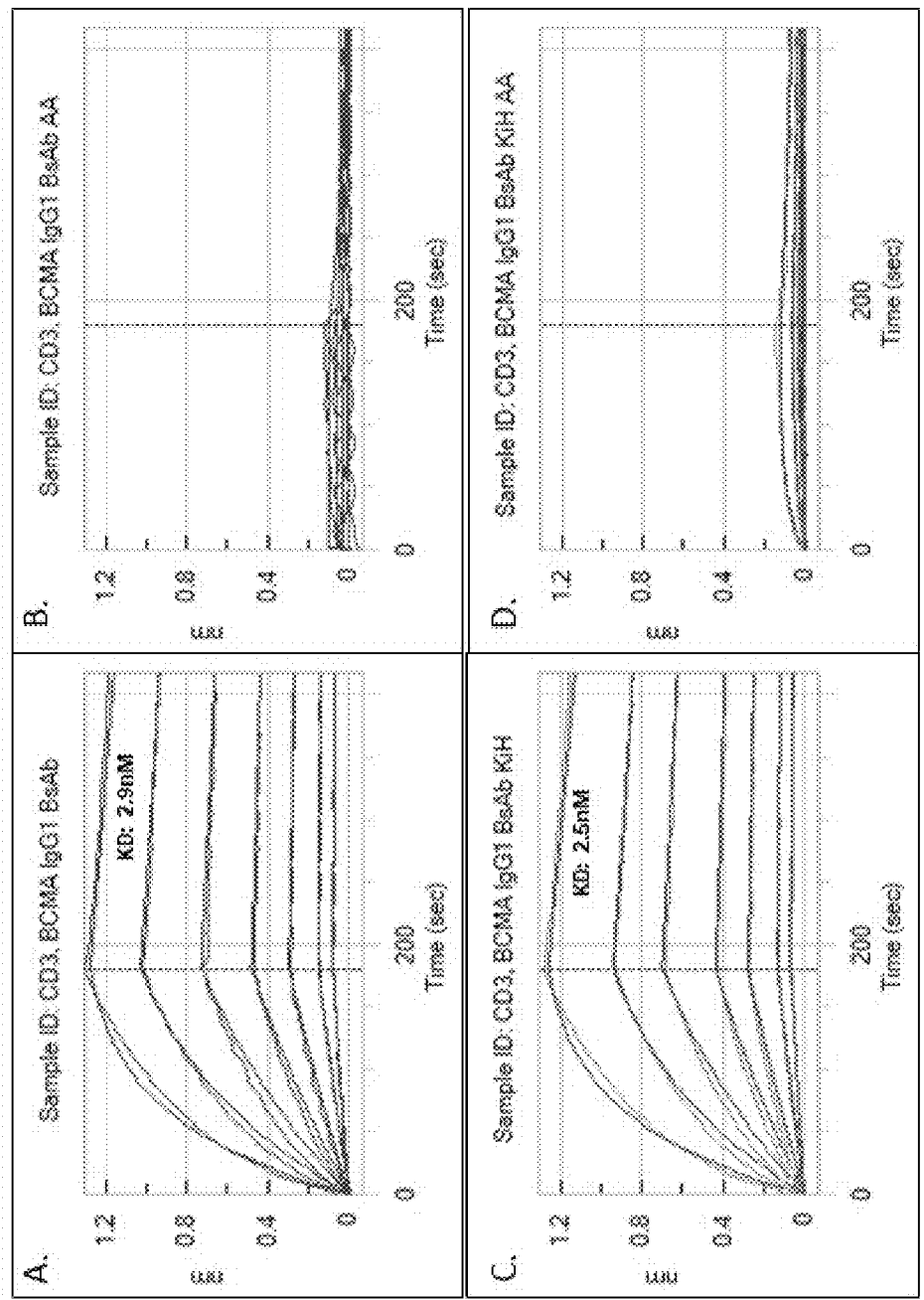
FIG. 4, panels A-D are graphs depicting Fc gamma receptor—antibody interactions for various IgG1 antibody species in accordance with embodiments of the invention.

Specifically, FIG. 4, panel A shows the results from a bispecific CD3×BCMA (monovalent) IgG1 antibody that does not comprise KiH mutations or silencing mutations.

The data demonstrate that the antibody interacts with the Fc gamma receptor immobilized on the biosensor. FIG. 4, panel B shows the results from the same bispecific antibody used in panel A, but now including silencing mutations in the CH2 domain. These results demonstrate that interaction between the antibody and the Fc gamma receptor on the biosensor is significantly reduced due to the presence of the silencing mutations. FIG. 4, panel C shows the results from a bispecific CD3×BCMA (monovalent) IgG1 antibody that does include KiH mutations, but does not include silencing mutations. These data demonstrate that the antibody interacts with the Fc gamma receptor immobilized on the biosensor in a manner that is very similar to what was observed with the antibody in panel A. FIG. 4, panel D shows the results from the same bispecific antibody used in panel C, but now including silencing mutations in the CH2 domain. These results demonstrate that interaction between the antibody and the Fc gamma receptor on the biosensor is significantly reduced due to the presence of the silencing mutations, even when the KiH mutations are included.

Figure 5:
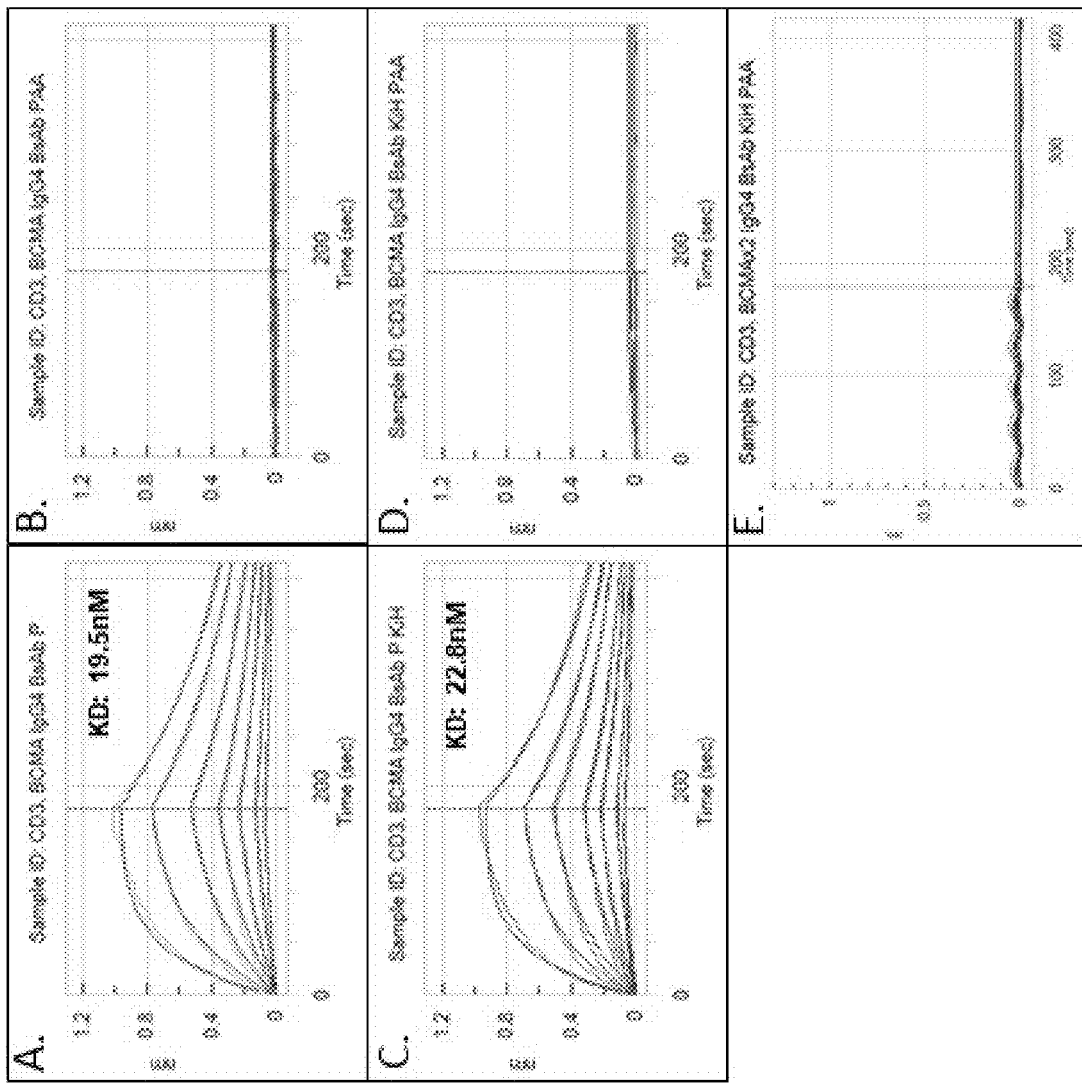
FIG. 5, panels A-E are graphs depicting Fc gamma receptor—antibody interactions for various IgG4 antibody species in accordance with embodiments of the invention.

FIG. 5, panel A shows the results from a bispecific CD3×BCMA (monovalent) IgG4 antibody that does not comprise KiH mutations or silencing mutations, but that does include an S228P mutation to prevent Fab arm exchange. The data demonstrate that the antibody interacts with the Fc gamma receptor immobilized on the biosensor. FIG. 5, panel B shows the results from the same bispecific antibody used in panel A, but now including silencing mutations in the CH2 domain (F234A, L235A). These results demonstrate that interaction between the antibody and the Fc gamma receptor on the biosensor is significantly reduced due to the presence of the silencing mutations, even when the S228P mutation is present. FIG. 5, panel C shows the results from a bispecific CD3×BCMA (monovalent) IgG4 antibody that does include KiH mutations and the S228P mutation, but does not include silencing mutations. These data demonstrate that the antibody interacts with the Fc gamma receptor immobilized on the biosensor in a manner that is very similar to what was observed with the antibody in panel A. FIG. 5, panel D shows the results from the same bispecific antibody used in panel C, but now including silencing mutations in the CH2 domain (F234A, L235A), in addition to the S228P and KiH mutations. These results demonstrate that interaction between the antibody and the Fc gamma receptor on the biosensor is significantly reduced due to the presence of the silencing mutations, even when the S228P and KiH mutations are included. Panel E shows the results from a bispecific CD3×BCMA (bivalent) IgG4 antibody that inludes the S228P mutation, the silencing mutations F234A and L235A, as well as the KiH mutations in the CH3 domain. These data demonstrate that interaction between this antibody and the Fc gamma receptor immobilized on the biosensor was significantly reduced, even with S228P and the KiH mutations present.

Figure 6:
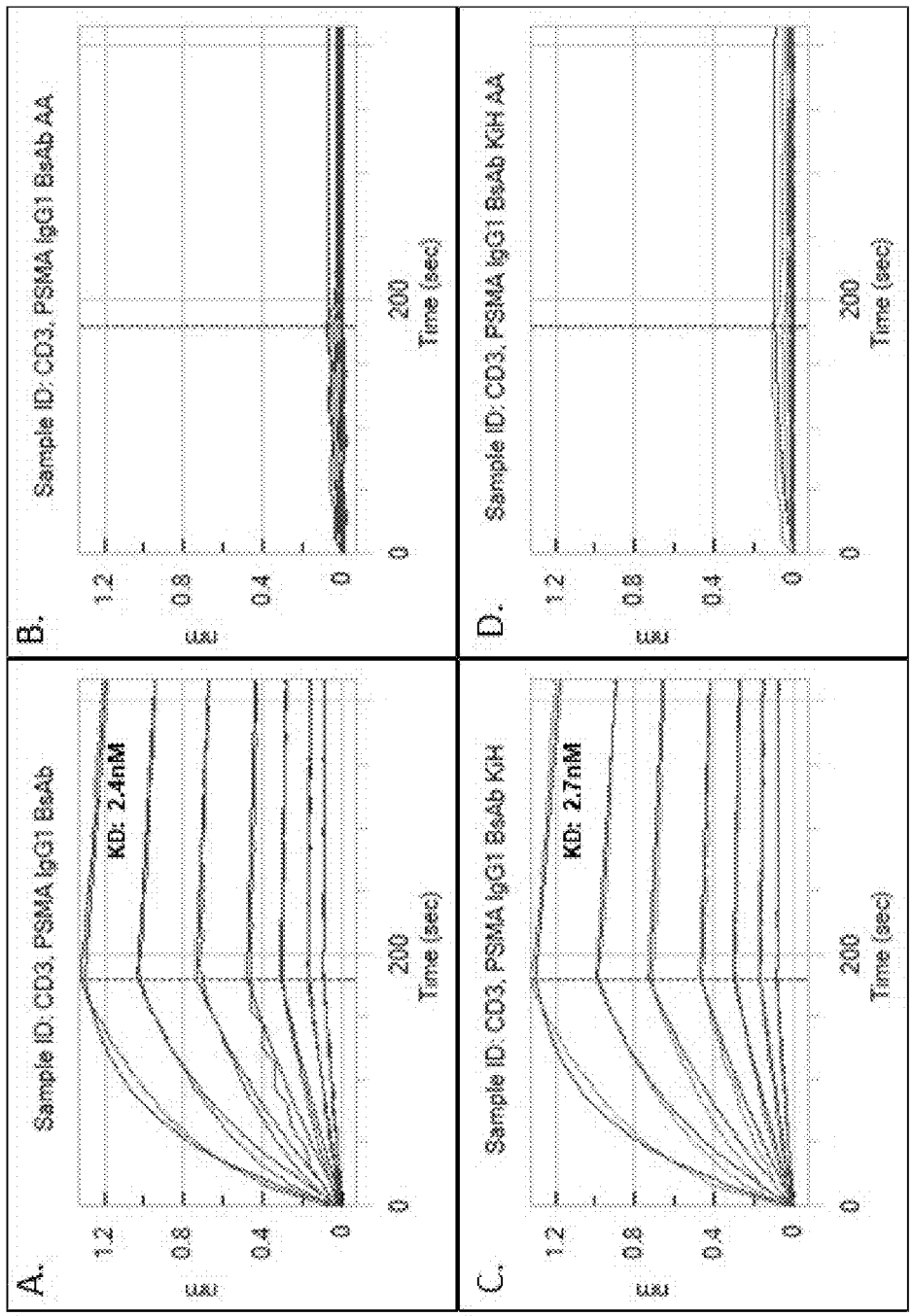
FIG. 6, panels A-D, are graphs depicting Fc gamma receptor—antibody interactions for various IgG1 antibody species in accordance with embodiments of the invention.

FIG. 6, panel A shows the results from a bispecific CD3×PSMA (monovalent) IgG1 antibody that does not comprise KiH mutations or silencing mutations. The data demonstrate that the antibody interacts with the Fc gamma receptor immobilized on the biosensor. FIG. 6, panel B shows the results from the same bispecific antibody used in panel A, but now including silencing mutations in the CH2 domain. These results demonstrate that interaction between the antibody and the Fc gamma receptor on the biosensor is significantly reduced due to the presence of the silencing mutations. FIG. 6, panel C shows the results from a bispecific CD3×PSMA (monovalent) IgG1 antibody that does include KiH mutations, but does not include silencing mutations. These data demonstrate that the antibody interacts with the Fc gamma receptor immobilized on the biosensor in a manner that is very similar to what was observed with the antibody in panel A. FIG. 6, panel D shows the results from the same bispecific antibody used in panel C, but now including silencing mutations in the CH2 domain. These results demonstrate that interaction between the antibody and the Fc gamma receptor on the biosensor is significantly reduced due to the presence of the silencing mutations, even when the KiH mutations are included.

Figure 7:
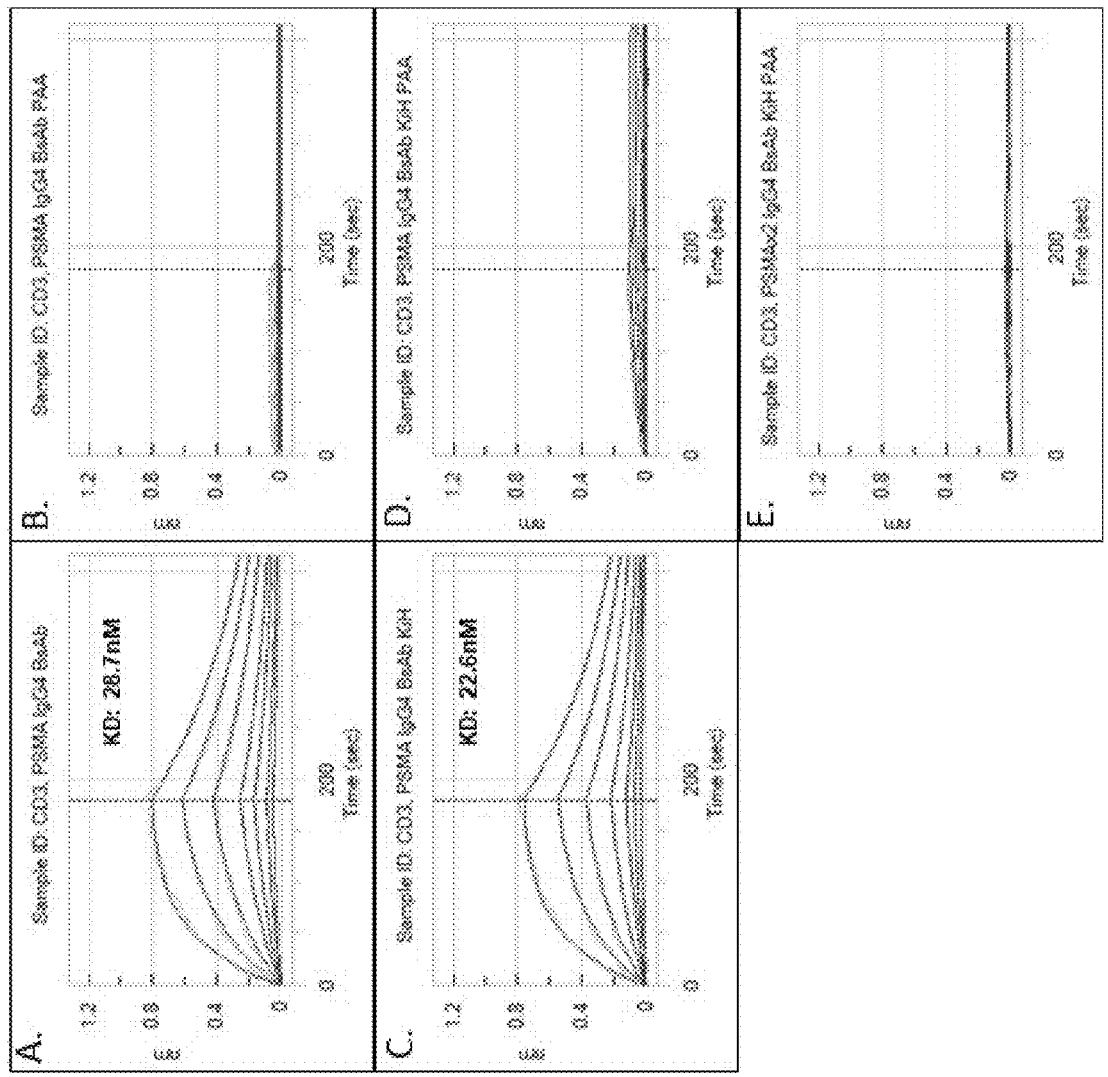
FIG. 7, panels A-E are graphs depicting Fc gamma receptor—antibody interactions for various IgG4 antibody species in accordance with embodiments of the invention.

FIG. 7, panel A shows the results from a bispecific CD3×PSMA (monovalent) IgG4 antibody that does not comprise KiH mutations or silencing mutations, but that does include an S228P mutation to prevent Fab arm exchange. The data demonstrate that the antibody interacts with the Fc gamma receptor immobilized on the biosensor. FIG. 7, panel B shows the results from the same bispecific antibody used in panel A, but now including silencing mutations in the CH2 domain (F234A, L235A). These results demonstrate that interaction between the antibody and the Fc gamma receptor on the biosensor is significantly reduced due to the presence of the silencing mutations, even when the S228P mutation is present. FIG. 7, panel C shows the results from a bispecific CD3×PSMA (monovalent) IgG4 antibody that does include KiH mutations and the S228P mutation, but does not include silencing mutations. These data demonstrate that the antibody interacts with the Fc gamma receptor immobilized on the biosensor in a manner that is very similar to what was observed with the antibody in panel A. FIG. 7, panel D shows the results from the same bispecific antibody used in panel C, but now including silencing mutations in the CH2 domain (F234A, L235A), in addition to the S228P and KiH mutations. These results demonstrate that interaction between the antibody and the Fc gamma receptor on the biosensor is significantly reduced due to the presence of the silencing mutations, even when the S228P and KiH mutations are included. Panel E shows the results from a bispecific CD3×PSMA (bivalent) IgG4 antibody that inludes the S228P mutation, the silencing mutations F234A and L235A, as well as the KiH mutations in the CH3 domain. These data demonstrate that interaction between this antibody and the Fc gamma receptor immobilized on the biosensor was significantly reduced, even with S228P and the KiH mutations present.

Figure 26:
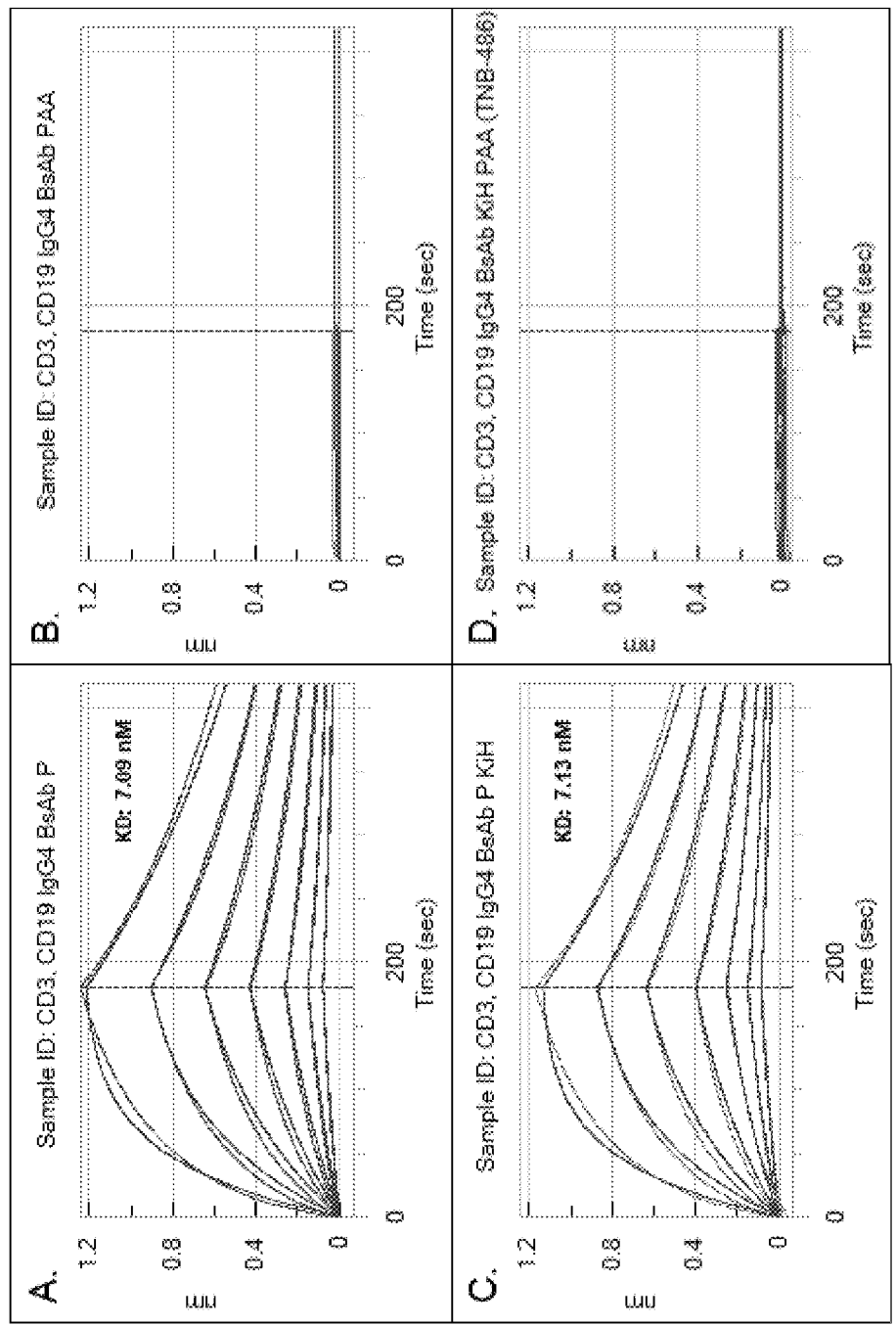
FIG. 26, panels A-D, are graphs depicting Fc gamma receptor—antibody interactions for various IgG4 antibody species in accordance with embodiments of the invention.

FIG. 26, panel A, shows the results from a bispecific CD3× CD19 (monovalent) IgG4 antibody that does not comprise KiH mutations or silencing mutations, but that does include an S228P mutation to prevent Fab arm exchange. The data demonstrate that the antibody interacts with the Fc gamma receptor immobilized on the biosensor. FIG. 26, panel B, shows the results from the same bispecific antibody used in panel A, but now including silencing mutations in the CH2 domain (F234A, L235A). These results demonstrate that interaction between the antibody and the Fc gamma receptor on the biosensor is significantly reduced due to the presence of the silencing mutations, even when the S228P mutation is present. FIG. 26, panel C, shows the results from a bispecific CD3× CD19 (monovalent) IgG4 antibody that does include KiH mutations and the S228P mutation, but does not include silencing mutations. These data demonstrate that the antibody interacts with the Fc gamma receptor immobilized on the biosensor in a manner that is very similar to what was observed with the antibody in panel A. FIG. 26, panel D, shows the results from the same bispecific antibody used in panel C, but now including silencing mutations in the CH2 domain (F234A, L235A), in addition to the S228P and KiH mutations. These results demonstrate that interaction between the antibody and the Fc gamma receptor on the biosensor is significantly reduced due to the presence of the silencing mutations, even when the S228P and KiH mutations are included.

Together, the data provided in FIGS. 4, 5, 6, 7, and 26 demonstrate that the $V_H$ region sequence of a bispecific antibody has no impact on the functional properties of the IgG4 Fc mutations described herein. As such, the IgG4 Fc modifications described herein (S228P; F234A, L235A; T366W, T366S, L368A, and Y407V) can be implemented in antibodies having different $V_H$ sequences (i.e., different binding targets) to achieve reduced Fab arm exchange (S228P), reduced effector function activity (F234A, L235A), and proper heterodimerization (T366W; T366S, L368A, and Y407V).

Example 3: Flow Cytometry Analysis of Binding to PSMA Positive and Negative Cells by Anti-PSMA UniAbs™

Binding to PSMA-positive cells was assessed by flow cytometry (Guava easyCyte 8HT, EMD Millipore) using the LNCaP cell line (ATCC: CRL-1740), 22Rv1 cell line (ATCC CRL-2505), a PC3 cell line (ATCC CRL-1435) stably transfected to express human PSMA, or the DU-145 cell line (ATCC HTB-81). Briefly, 50,000 target cells were stained with a dilution series of purified UniAbs™ for 30 minutes at 4° C. Following incubation, the cells were washed twice with flow cytometry buffer (1×PBS, 1% BSA, 0.1% $NaN_3$) and stained with goat F(ab')$_2$ anti-human IgG conjugated to R-phycoerythrin (PE) (Southern Biotech, cat. #2042-09) to detect cell-bound antibodies. After a 20-minute incubation at 4° C., the cells were washed twice with flow cytometry buffer and the mean fluorescence intensity (MFI) was measured by flow cytometry. The MFI of cells stained with secondary antibody alone were used for determination of background signal and binding of each antibody was converted to fold over background. Binding to cynomolgus PSMA positive cells was determined using the same protocol with the following modifications: the target cells were from Freestyle 293-F cells (ThermoFisher R79007) transiently transfected to express the extracellular domain of cynomolgus PSMA. In some experiments EC50 values were calculated using GraphPad Prism 7.

Table 8 summarizes target binding activity of the anti-PSMA heavy-chain antibodies (HCAb) described herein. Column 1 indicates the clone ID of the HCAb. Column 2 indicates binding to LNCaP cells measured as fold over the background MFI signal.

TABLE 8

Binding to PSMA-expressing cell line

| Column 1: CLONE_ID | Column 2: LNCaP |
|---|---|
| 325920 | 282 |
| 346181 | 264 |
| 346165 | 243 |
| 346172 | 216 |
| 326109 | 25 |
| 325867 | 210 |
| 325742 | 200 |
| 325748 | 193 |
| 325940 | 169 |
| 325836 | 163 |
| 326027 | 138 |
| 326087 | 129 |

TABLE 8-continued

Binding to PSMA-expressing cell line

| Column 1: CLONE_ID | Column 2: LNCaP |
|---|---|
| 326084 | 125 |
| 326028 | 117 |
| 345497 | 112 |
| 326029 | 109 |
| 345461 | 102 |
| 345493 | 101 |
| 345436 | 87 |
| 345443 | 84 |
| 345490 | 80 |
| 345482 | 80 |
| 345485 | 71 |
| 345463 | 68 |
| 325932 | 64 |
| 345505 | 59 |
| 345508 | 55 |
| 345480 | 47 |
| 326116 | 38 |
| 345509 | 37 |
| 345444 | 23 |
| 345421 | 22 |
| 345447 | 14 |
| 345510 | 13 |
| 345438 | 13 |

Figure 8:
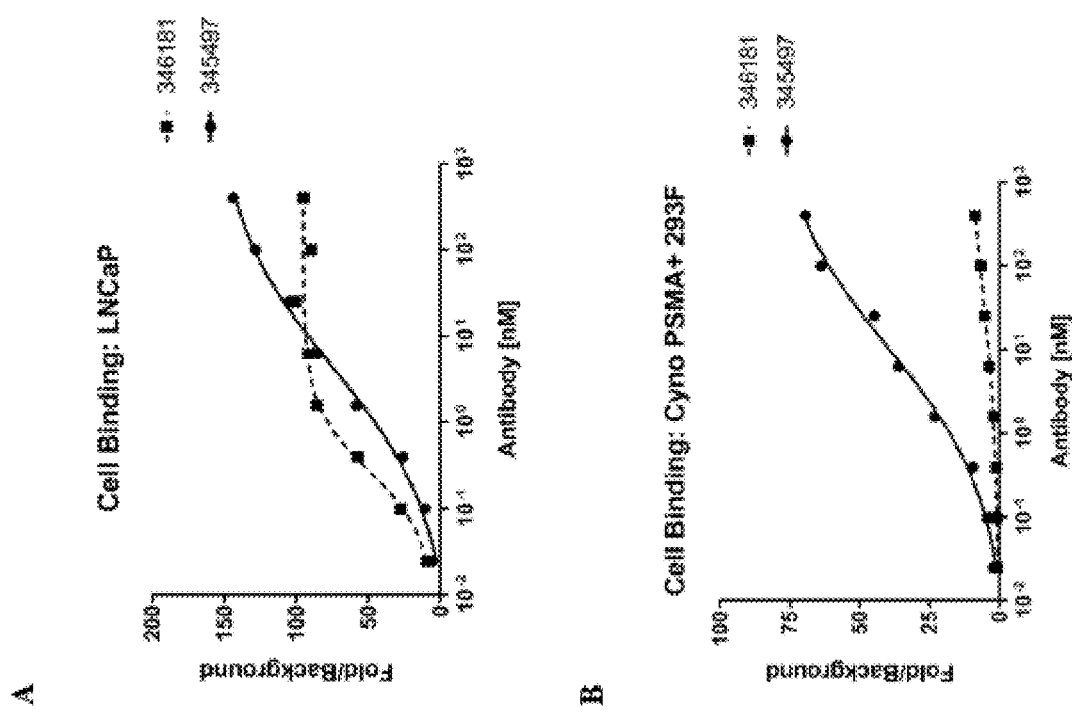
FIG. 8, panel A is a graph showing cell binding to human PSMA.

The differences in binding to cynomolgus PSMA, as shown in FIG. 8, panels A and B, supports the difference in human PSMA epitope recognized by HCAbs 346181 and 345497.

Example 4: Composition of Biparatopic and Bivalent Anti-PSMA Antibodies

As shown in Table 9, anti-PSMA clone ID 350123 is composed of clone ID 346181 sequence linked to clone ID 345497 sequence with the bridging sequence GGGGSGGGGS (SEQ ID NO: 71). Clone ID 350122 is composed of two repeats of clone ID 346181 joined by the same linker sequence. Clone ID 350123 is biparatopic as it is composed of two anti-PSMA domains recognizing different epitopes on PSMA. Clone ID 350122 is bivalent but not biparatopic, as it is composed of the same anti-PSMA domain in tandem. Schematic illustrations of various three-chain antibody-like molecules (TCAs) are depicted in FIG. 1, panels A-C.

TABLE 9

Description of amino acid sequence of biparatopic and bivalent anti-PSMA antibodies

| Clone ID | Sequence 1 | Linker sequence | Sequence 2 |
|---|---|---|---|
| 350123 | 346181 | GGGGSGGGGS (SEQ ID NO: 71) | 345497 |
| 350122 | 346181 | GGGGSGGGGS (SEQ ID NO: 71) | 346181 |

Example 5: Multi-Specific Antibody Mediated Killing of PSMA Positive Prostate Tumor Cells Through T-Cell Redirection Assays Using Resting T-Cells Target cells were seeded at 15,000 cells per well in a 96-well plate and grown overnight at 37° C. Following incubation, increasing amounts of multi-specific antibody were added together with resting human T-cells at a 10:1 effector to target cell ratio and incubated for an additional 48 or 72 hours at 37° C. (48 hours for assays with LNCaP, MDA-PCa-2b and PC3-PSMA cells and 72 hours for assays with 22Rv1 cells). Cell death was measured using either the cell proliferation reagent WST-1 (Sigma Cat No.: 11644807001) or flow cytometry. In some experiments, a small sample of each supernatant was collected after incubation but prior to analysis of target cell viability and saved for analysis of cytokine production. When cell viability was analyzed with WST-1 reagent, the reagent stock was added to each well at a 1:10 dilution and incubated for 90 minutes at 37° C. The absorbance was then measured at 450 nm (reference 690 nm), and the percent specific lysis was calculated.

If target cell viability was analyzed by flow cytometry, then the target cells were labeled before initiating the assay with the membrane dye DiR (ThermoFisher D12731). After incubation with T-cells and antibody, the supernatants were either saved for cytokine analysis or disposed of. Wells were then washed once to collect dead tumor cells and T-cells, which were transferred to a flow cytometry plate. The remaining attached tumor cells were trypsinized and then added to the corresponding wells in the flow cytometry plate. Annexin-V reagent was used to stain dead cells and flow cytometry was conducted (BD FACSCelesta) to quantitate the percent of dead tumor cells in each sample, gated by DiR staining. Wells containing untreated target cells were used to normalize for spontaneous cell death. In some experiments, a negative control antibody was used, consisting of the same CD3-targeting arm as in the PSMA×CD3 multi-specific molecules, but replacing the tumor-targeting arm with a VH specific to the HIV protein gp120.

Figure 9:
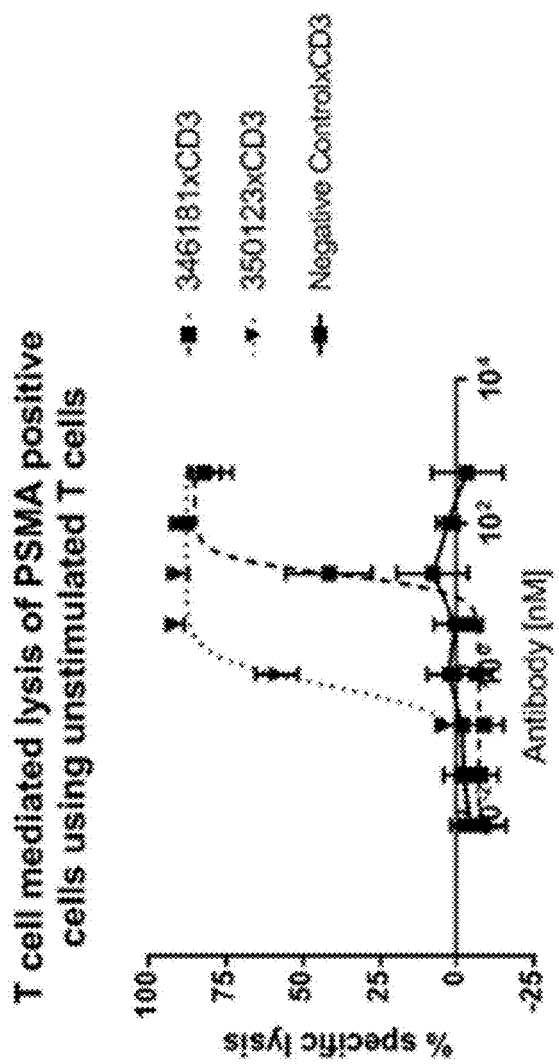
FIG. 9 is a graph depicting T-cell mediated lysis of PSMA positive cells using unstimulated T-cells.

FIG. 9 shows T-cell mediated lysis of PSMA positive cells using unstimulated T-cells. Unstimulated human T-cells were incubated with PSMA-expressing cells (LNCaP) and different concentrations of multi-specific antibodies. The biparatopic anti-PSMA×CD3 antibody (350123×CD3) outperformed the monoparatopic PSMA×CD3 antibody (346181×CD3).

Assays Using Pre-Activated T-Cells

Human pan T-cells were pre-activated with plate-bound OKT3 and IL-2 for three days, followed by an additional day of incubation in fresh IL-2. Target cells were trypsinized, loaded with Calcein-AM (ThermoFisher C3100MP), mixed with activated T-cells to an E:T ratio of 20:1, and added to the wells of a 96-well plate. Dilution series of different multi-specific antibodies were added, followed by incubation for 4 hours at 37° C. Supernatants were then transferred to black 96-well plates and absorbance was measured at 480 nm/520 nm ex/em to quantify release of calcein. Target cells incubated without T-cells were used to normalize for spontaneous calcein release of intact tumor cells. Addition of 2% Triton-X to control wells containing target cells allowed for calculation of the calcein signal corresponding to maximum cell lysis. Using this value, each experimental well was reported as percent of maximum cell lysis. Data analysis was conducted using GraphPad prism 7.

Figure 10:
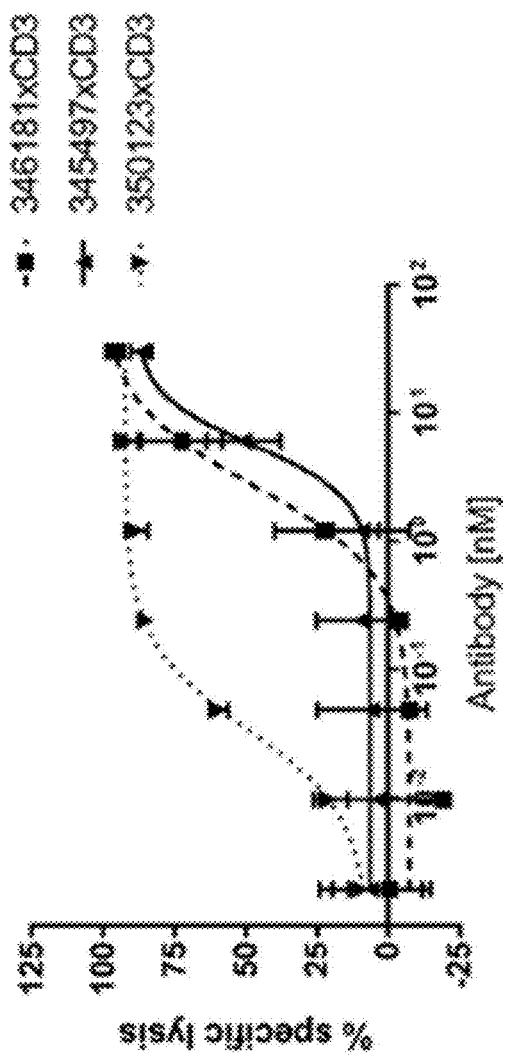
FIG. 10 is a graph depicting T-cell mediated lysis of PSMA positive cells using pre-activated T-cells.

FIG. 10 shows T-cell mediated lysis of PSMA positive cells using pre-activated T-cells. Pre-activated human T-cells were incubated with human PSMA-expressing cells (LNCaP) and different concentrations of multi-specific antibodies. Tumor cell death was measured by calcein release and normalized to spontaneous release of tumor cells in the absence of T-cells. The biparatopic anti-PSMA×CD3 antibody (350123×CD3) outperformed both monoparatopic PSMA×CD3 antibodies.

Figure 11:
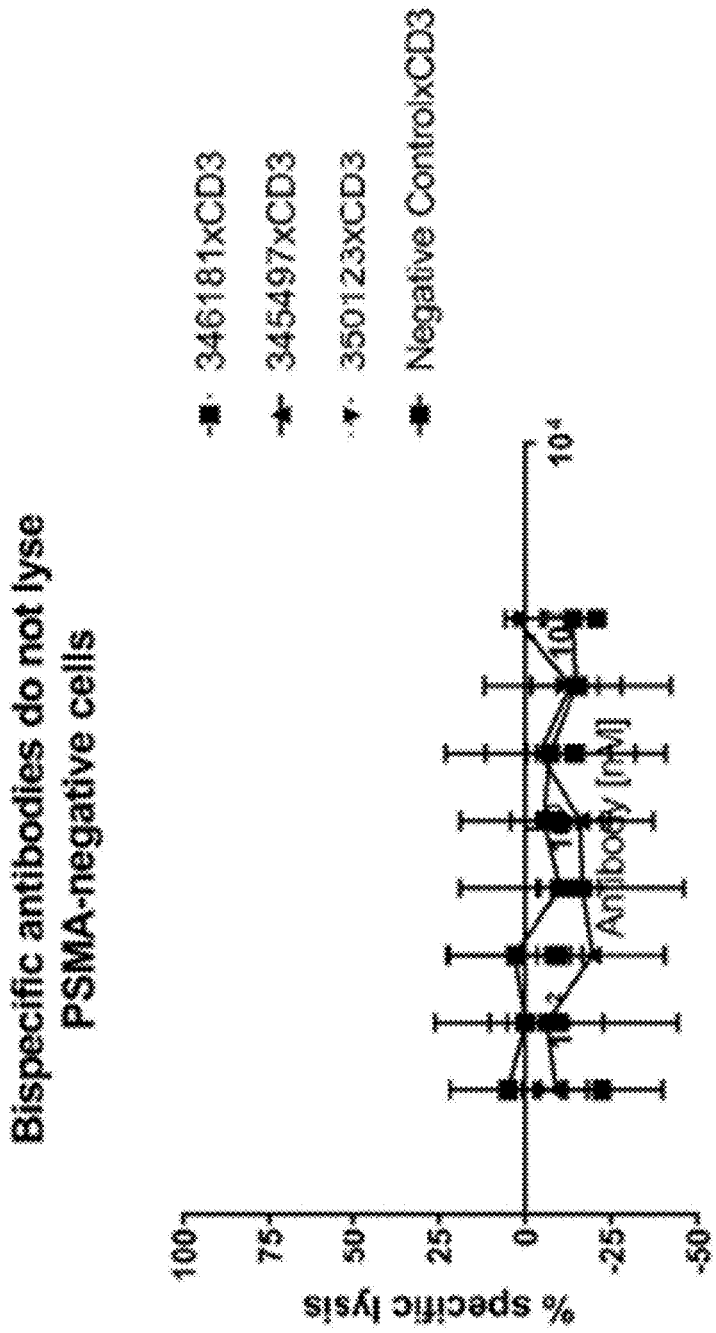
FIG. 11 is a graph depicting percent specific lysis of PSMA negative DU145 cells as a function of multi-specific antibody concentration in the presence of pre-activated T-cells.

FIG. 11 shows that multi-specific antibodies do not lyse PSMA-negative cells. Pre-activated human T-cells were incubated with PSMA-negative prostate cancer cells (DU145) and different concentrations of multi-specific antibodies. No lysis of these cells occurred by any of the antibodies tested.

Figure 12:
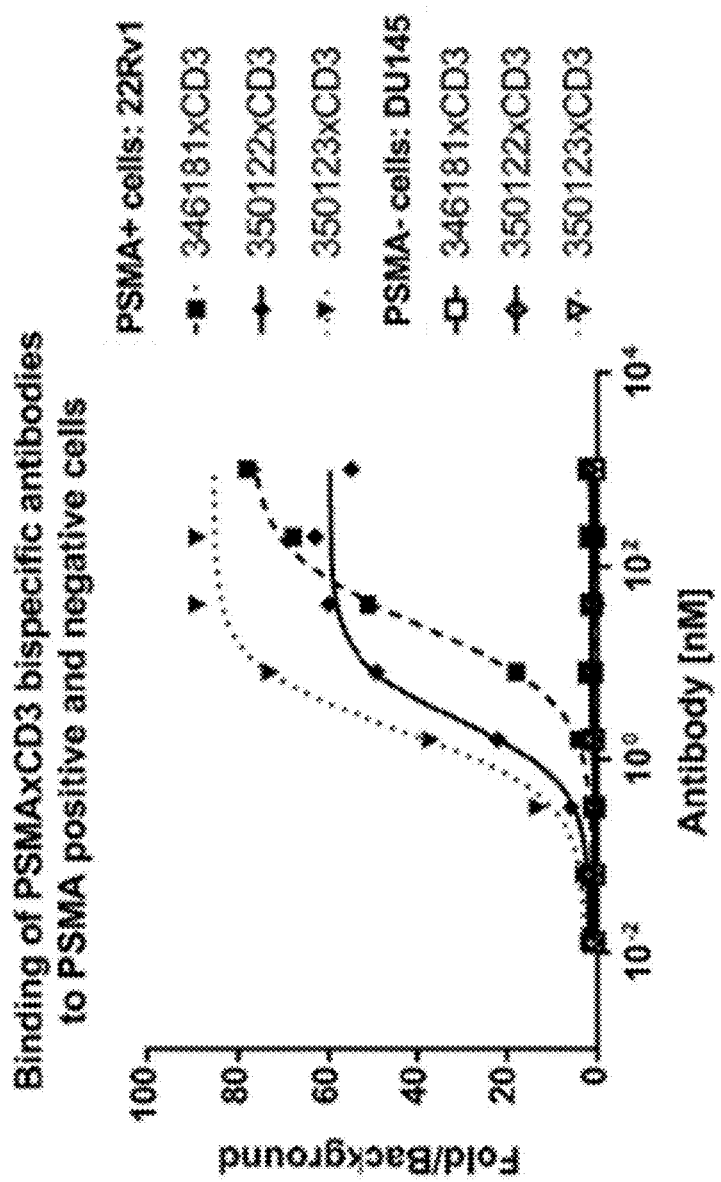
FIG. 12 is a graph showing binding of PSMA×CD3 bispecific antibodies to PSMA positive and negative cells.

FIG. 12 shows binding of PSMA×CD3 multi-specific antibodies to PSMA positive and negative cells. Multi-specific anti-PSMA×anti-CD3 antibodies show binding to PSMA positive prostate tumor cells (22Rv1), but no binding to PSMA negative prostate tumor cells (DU145). The biparatopic molecule (350123) showed the strongest on-target cell binding.

Figure 13:
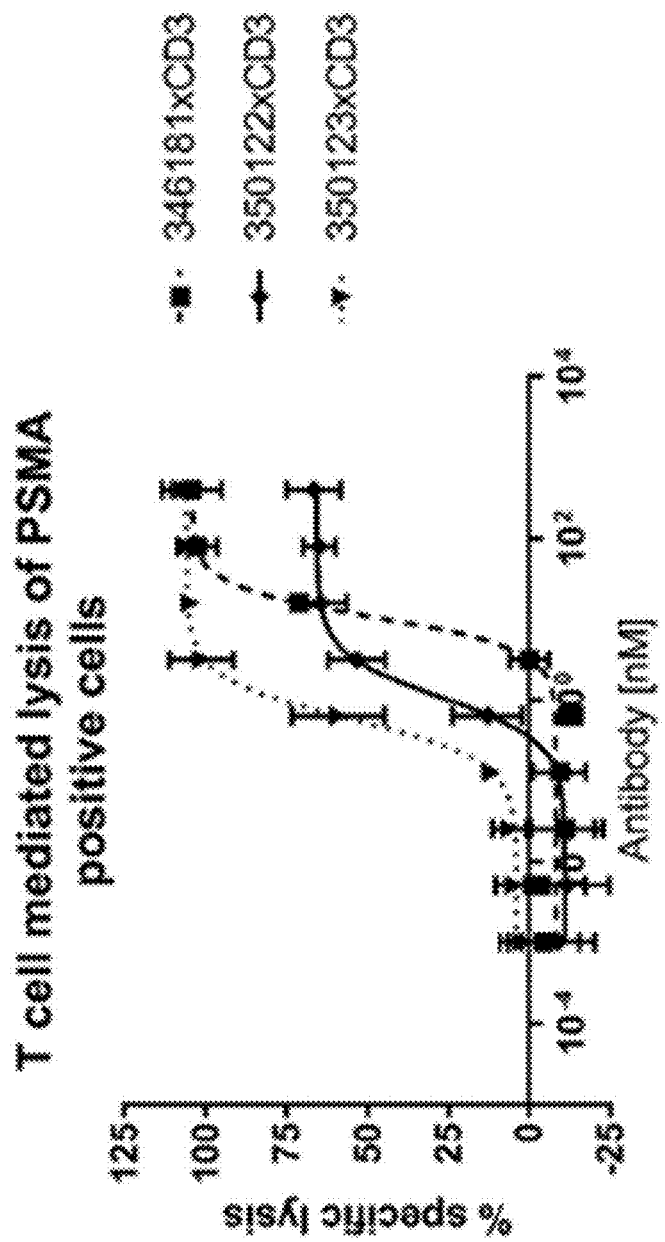
FIG. 13 is a graph showing T-cell mediated lysis of PSMA positive cells.

FIG. 13 depicts T-cell mediated lysis of PSMA positive cells. The data in FIG. 13 demonstrates that binding to PSMA via two different epitopes results in increased cell killing as compared to a bivalent but monospecific version of the antibody.

Example 6: A Monoparatopic PSMA×CD3 Bispecific Antibody Induces Less Cytokine Production than a Biparatopic PSMA×CD3 Multi-Specific Antibody Cytokine production was analyzed in tumor cytotoxicity assays with resting T-cells. The design of these assays is detailed elsewhere. Supernatants were collected upon completion of the assays (after 72 hours of incubation for assays using 22Rv1 cells, 48 hours for all other cell lines). ELISA kits were used for detection of IL-2 (Biolegend 431804) and IFNγ (Biolegend 430104) according to the manufacturer's protocol. Experimental supernatants were diluted before analysis in the ELISAs such that the levels of cytokines would fall within the linear portion of the standard curve supplied with each kit. In some cases, no cytokines could be detected in the experiment wells, and values were reported as less than or equal to the lower limit of quantification for the assay.

Figure 14:
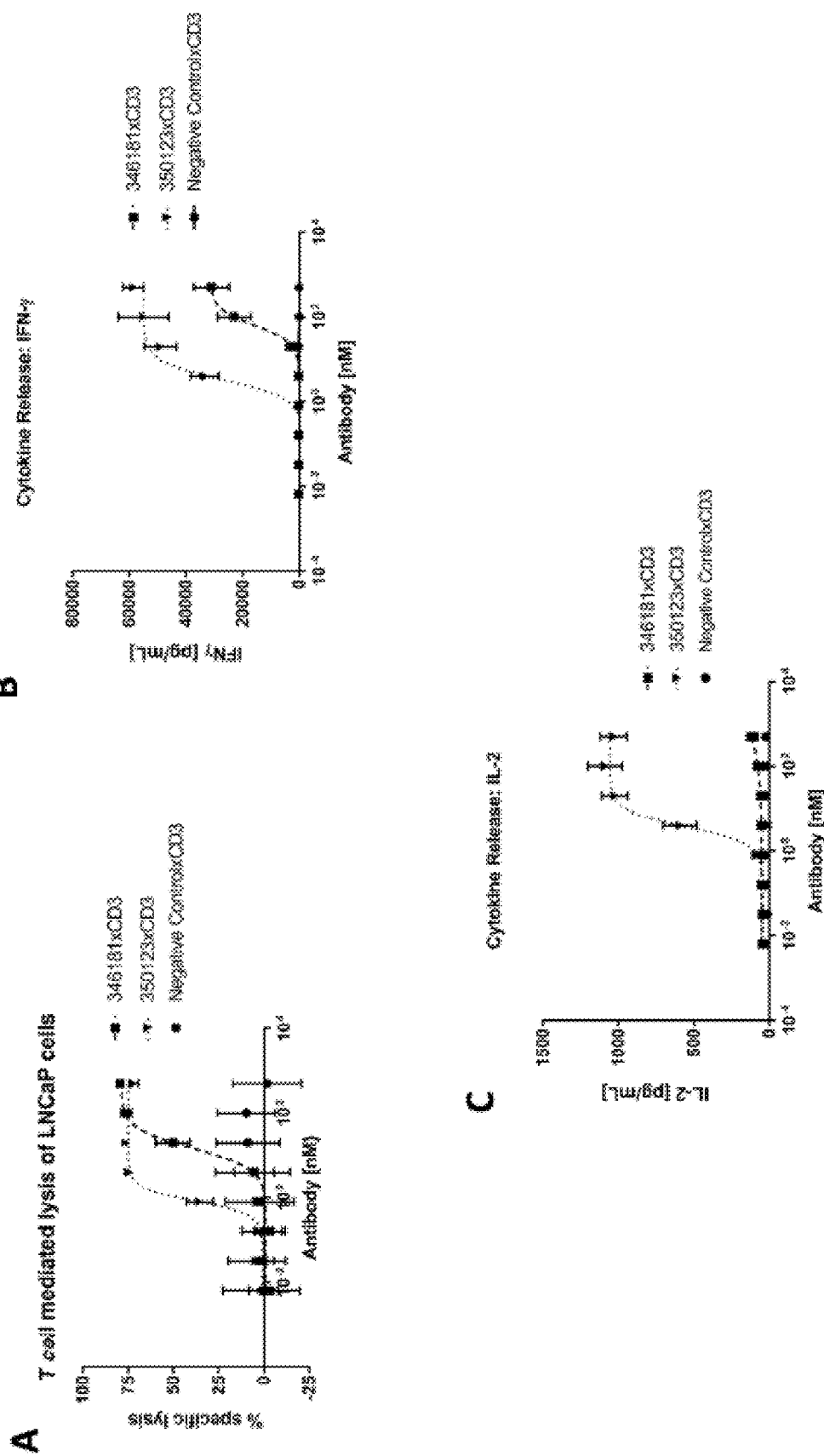
FIG. 14, panel A, is a graph depicting T-cell mediated lysis of PSMA positive cells as a function of antibody concentration. Panel B, is a graph depicting cytokine (IFNγ) release as a function of antibody concentration. Panel C, is a graph depicting cytokine (IL-2) release as a function of antibody concentration.

FIG. 14 (Panels A, B, and C) shows T-cell mediated lysis of PSMA positive cells and comparison with cytokine production. Multi-ispecific PSMA×CD3 antibodies induce T-cell mediated lysis of the PSMA positive prostate cancer cell line LNCaP. The biparatopic molecule (350123) stimulated more potent tumor cell killing as compared to the monoparatopic molecule (346181), but also caused production of higher levels of the cytokines interferon gamma (IFNγ) and interleukin 2 (IL-2), as exemplified by FIG. 14, panels B and C.

Table 10 shows T-cell mediated lysis and cytokine production against four PSMA positive prostate tumor cell lines. The PSMA×CD3 multi-specific antibodies were tested in in vitro tumor cell cytotoxicity assays using unstimulated T-cells and a dose series of antibody against a panel of four PSMA positive tumor cell lines. After 72 hours (22Rv1) or 48 hours (MDA-PCa-2b, LNCAP, PC3-PSMA) the percent of tumor cell death was calculated and reported by EC50 as well as the highest percent killing achieved. Supernatants from these experiment wells were collected and analyzed by ELISA for the cytokines interferon-gamma (IFNγ) or interleukin-2 (IL-2). The monoparatopic molecule (3461881) induced approximately equivalent levels of tumor cytotoxicity against all four cell lines tested as compared to the biparatopic molecule, but had higher EC50s for cytokine production and in most cases stimulated lower levels of maximum cytokine production.

TABLE 10

T-cell mediated lysis and cytokine production against four PSMA positive prostate tumor cell lines.

| Cell line | Antibody | Cell binding EC50 (nM) | Max Cytoxicity (% lysis) | Kill EC50 (nM) | Max IFNγ (pg/mL) | IFNγ EC50 (nM) | Max IL-2 (pg/ml) | IL-2 EC50 (nM) |
|---|---|---|---|---|---|---|---|---|
| 22Rv1 | 346181xCD3 | 58 | 45 | 52.8 | 21,150 | 173.8 | ≤LLOQ | NA |
|  | 350123xCD3 | 3 | 53 | 0.42 | 73,031 | 380.2 | ≤LLOQ | NA |
| MDA-PCa-2b | 346181xCD3 | 28 | 26 | 23.6 | 14,309 | 116.5 | 524 | 38.5 |
|  | 350123xCD3 | 2 | 29 | 0.41 | 12,026 | 0.90 | 1111 | 1.11 |
| LNCAP | 346181xCD3 | 17 | 79 | 14.6 | 32,237 | 63.0 | 183 | 575 |
|  | 350123xCD3 | 2 | 75 | 0.84 | 60,397 | 3.29 | 1057 | 3.73 |
| PC3-PSMA | 346181xCD3 | 30 | 42 | 3.7 | 7,340 | 10.1 | 1569 | 4.1 |
|  | 350123xCD3 | 6 | 51 | 0.40 | 10,136 | 1.01 | 3480 | 1.1 |

Example 7: PSMAxCD3 Multi-Specific Antibodies Induce T-Cell Proliferation

PSMA positive tumor cells were seeded at 25,000 cells per well in a 96-well plate and grown overnight at 37° C. Human pan T-cells isolated from resting PBMCs (Miltenyi 130-096-535) were labeled with the lineage tracing dye CFSE according to manufacturer's instructions (ThermoFisher C34554). 100,000 labeled pan T-cells were then added to the wells containing the tumor cells, followed by a dilution series of antibodies, and incubated at 37° C., 8% $CO_2$. After 5 days of incubation, the cells were mixed gently and transferred to a flow cytometry plate. The cells were pelleted, and the supernatant removed, followed by staining with anti-CD8 conjugated to APC (Biolegend 301049) and anti-CD4 conjugated to PE (Biolegend 317410) for 20 minutes on ice. The cells were then washed and resuspending in flow cytometry buffer for analysis (BD FACSCelesta). Cells were gated on forward and side scatter, and CD4 or CD8 expression. The percent of T-cells that had proliferated, as indicated by CD4 or CD8 positive staining and low or negative CFSE signal, was calculated for the entire T-cell population, as well as the CD4 and CD8 subsets. Flow cytometry data was analyzed using FlowJo and plotted in GraphPad Prism 7.

Figure 15:
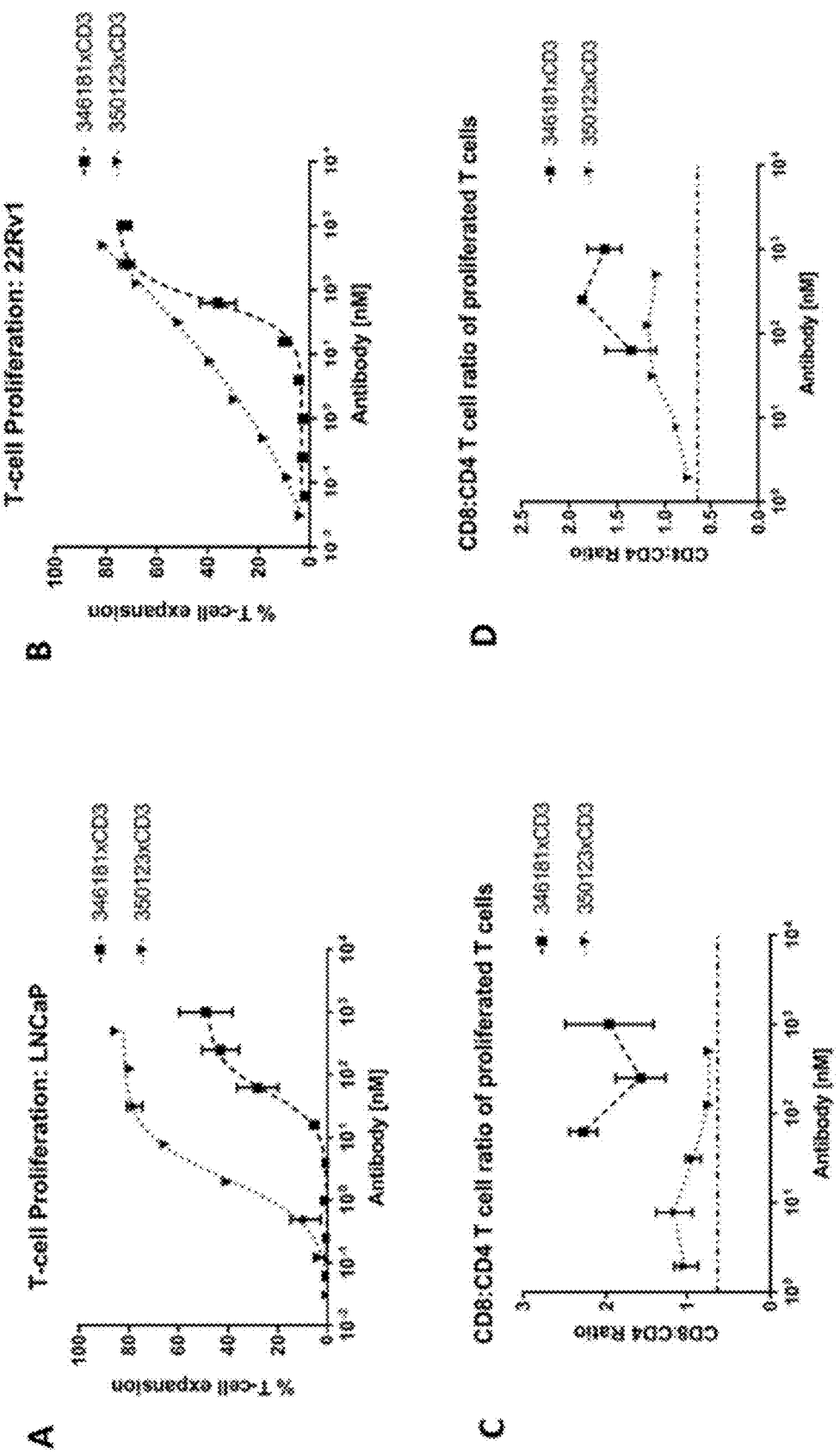
FIG. 15, panel A, is a graph depicting T-cell proliferation as a function of antibody concentration. Panel B, is a graph depicting T-cell proliferation as a function of antibody concentration. Panel C, is a graph depicting the ratio of CD8 to CD4 of proliferated T-cells. Panel D, is a graph depicting the ratio of CD8 to CD4 of proliferated T-cells.

FIG. 15 (Panels A, B, C, and D) shows that PSMAxCD3 multi-specific antibodies stimulated T-cell proliferation in the presence of PSMA positive tumor cells, and that monoparatopic PSMA bispecfic antibodies preferentially activate CD3 T-cells. Multi-specific antibodies were incubated together with PSMA expressing tumor cells and T-cells labeled with the lineage tracing dye CFSE. After 5 days of incubation, T-cell proliferation and the composition of proliferated T-cells (CD8+ versus CD4+) were analyzed by flow cytometry. Panels A and B show total T-cell proliferation, while panels C and D indicate the ratio of CD8+ to CD4+ T-cells in the proliferated wells. A dashed horizontal line indicates that CD8:CD4 ratio of the unstimulated T-cells and is approximately 1:2 (actual value=0.64). The monoparatopic PSMAxCD3 bispecific antibody (346181) preferentially activates CD8 T-cells (CD8:CD4 ratio after expansion of approximately 2:1) whereas the biparatopic PSMAxCD3 multi-specific antibody (350123) less preferentially activates CD8+ T-cells (CD8:CD4 ratio of about 1:1).

Example 8: A Multi-Specific Antibody Causes Suppression of Prostate Tumor Growth in a Xenograft Model 5-6 week old male immune-deficient CIEA-NOG mice (Taconic) were implanted with 10 million 22Rv1 cells subcutaneously into their lower right flanks, followed by addition of 10 million human PBMCs via tail vein injection one day following tumor implantation. The animals received treatment with 100 μg of multi-specific antibody or vehicle by tail vein injection starting one day after tumor implantation on days 1, 5, 9 and 13. Tumor volume was quantified using calipers and was recorded for 25 days.

Figure 16:
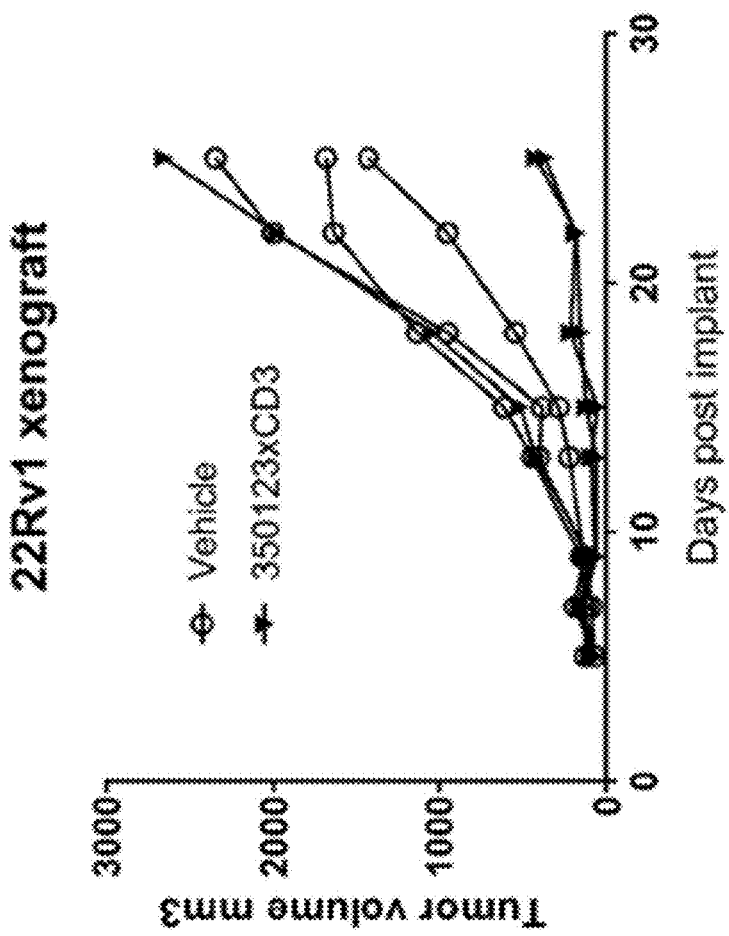
FIG. 16 is a graph depicting inhibition of 22Rv1 tumor growth in a tumor xenograft model.

FIG. 16 shows the results of the 22Rv1 tumor xenograft model. The biparatopic PSMAxCD3 molecule (350123) showed inhibition of 22Rv1 tumor growth in a tumor xenograft model. Three mice were tested for each treatment group, and the change in tumor volume for each animal was plotted in millimeters cubed. Animals received PBMCs on day 1 post tumor implantation and were treated with antibody on days 1, 5, 9, and 13. Two out of the three animals treated with multispecific antibody showed delay in tumor progression.

Example 9: Analysis of T-Cell Activation

CD69 is a cell surface marker on T-cells that is upregulated upon stimulation, thereby serving as an indicator of T-cell activation. In this experiment, CD69 activation was evaluated under 3 different conditions: 1) total peripheral blood mononuclear cells (PBMCs) without BCMA coating; 2) Pan T-cells with BCMA coating; and 3) Pan T-cells without BCMA coating. PBMCs were isolated from buffy coats using Ficoll (1.077 g/ml density) and cryopreserved PBMCs were thawed and rested for 24 hours at $2\times10^6$ cells/mL in RPMI1640 supplemented with 10% FBS at 37° C. On day 2, pan T cells were isolated from the rested PBMCs using a Miltenyi negative selection kit, and the isolated cells were used in the $2^{nd}$ and $3^{rd}$ assay conditions. For the first assay condition, PBMCs were counted and plated in the assay plates.

For cells that were evaluated under antigen coating conditions, 96-well plates were coated with recombinant BCMA protein at a concentration of 1 μg/mL (Human BCMA Protein, Fc Tag, Acro Biosystems, Catalog No—BC7-H5254), recombinant PSMA protein at a concentration of 1 μg/mL (Recombinant Human PSMA/FOLH1 Protein, from RND systems, Catalog No—4234-ZN-0101)), or recombinant CD19 protein at a concentration of 10 μg/mL (Human CD19 Protein, His Tag, Acro Biosystems, Catalog No—CD9-H52H2). Bispecific antibodies were analyzed using a 12-point dose curve with 3-fold dilutions, the highest dose being 300 nM. Bispecific antibodies and T-cells were resuspended in RPMI1640 supplemented with 10% FBS and incubated for 18 hours. Pan T-cells were the effector cells and were plated at 100K cells/well.

For cells that were evaluated without antigen coating conditions, bispecific antibodies were incubated with the cells using a 12-point dose curve with 3-fold dilutions. 300 nM of bispecific antibody was the highest concentration tested in this assay. Samples were incubated for 18 hours in RPMI1640 supplemented with 10% FBS at 37° C. Pan T-cells isolated from PBMCs were the effector cells that were plated at 100K cells/well.

For all experimental conditions, cells were washed and labeled with cell surface T-cell antibodies. The following antibodies were used to label (1) CD4 positive T-cells (FITC anti-human CD4 antibody), (2) CD8 positive T-cells (PE anti-human CD8a antibody), (3) CD69 activation (Alexa Fluor 647 anti-human CD69 antibody) (Biolegend). Cells were then analyzed on a BD Celesta using the appropriate templates to measure CD69 activation.

Figure 17:
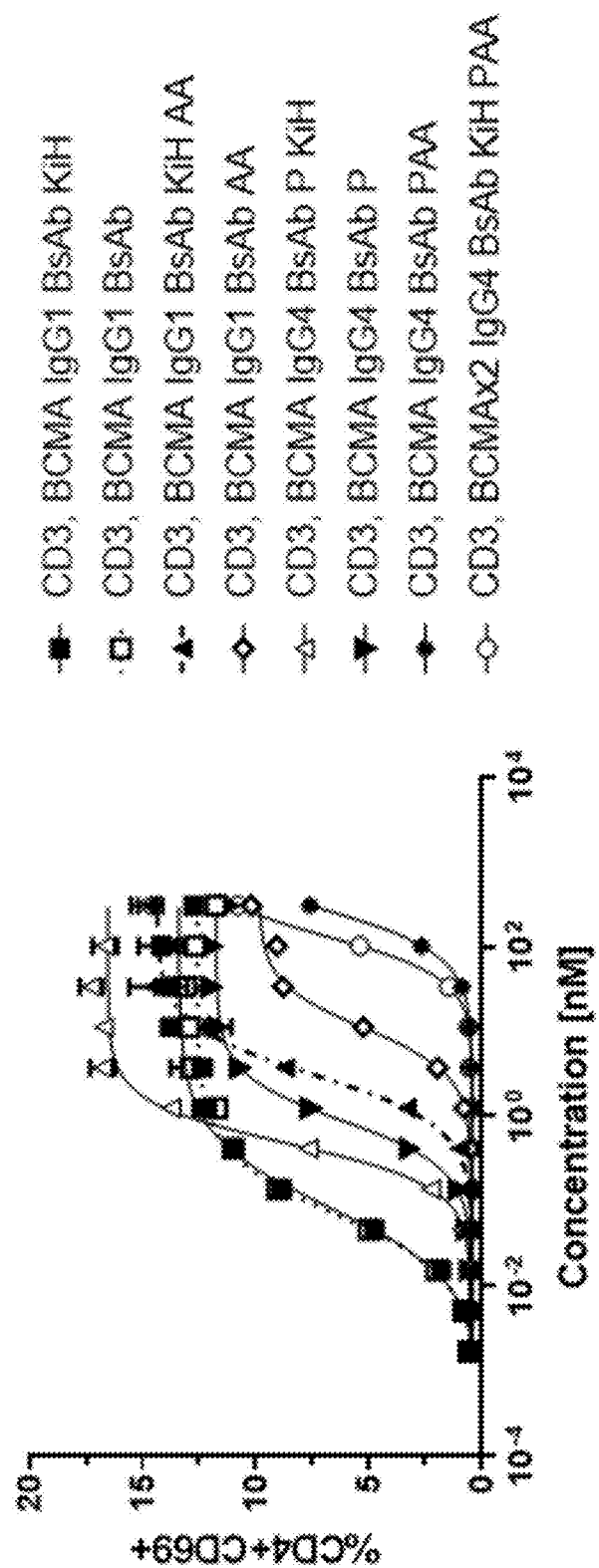
FIG. 17 is a graph depicting % CD4+CD69+ T-cells as a function of bispecific antibody concentration for the bispecific antibodies shown in the legend.
Figure 18:
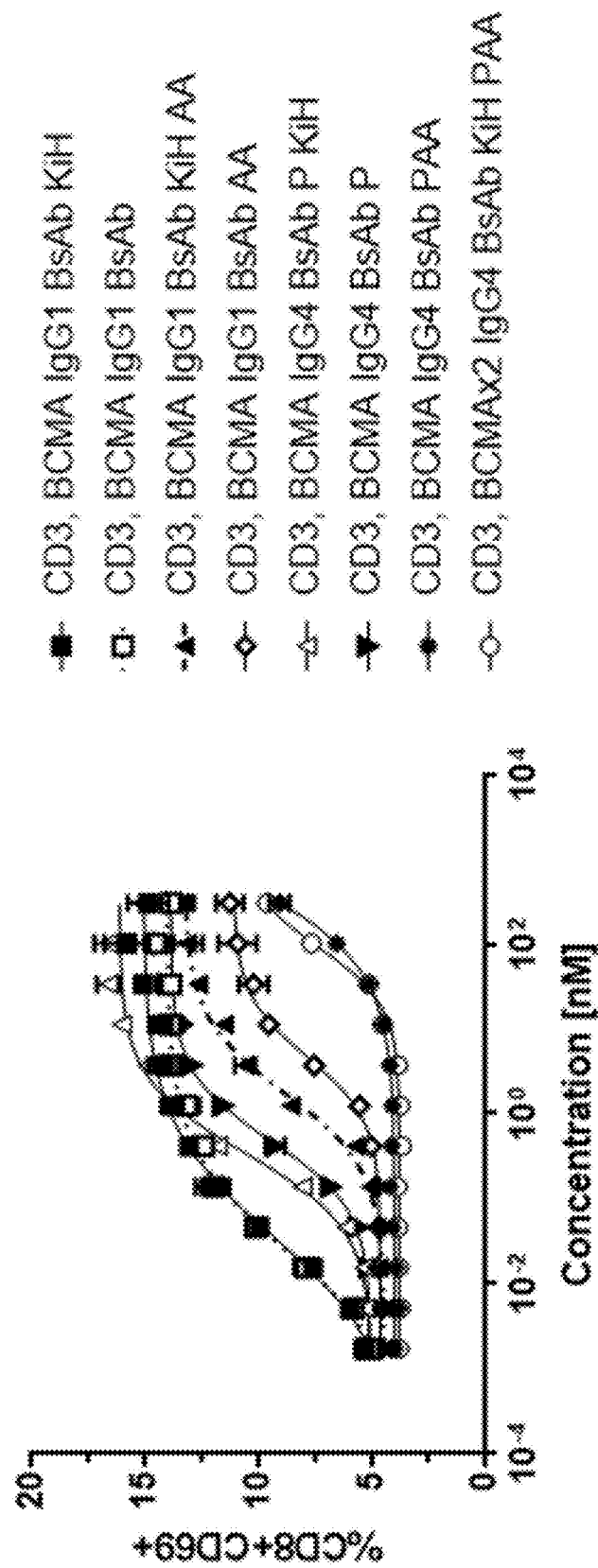
FIG. 18 is a graph depicting % CD8+CD69+ T-cells as a function of bispecific antibody concentration for the bispecific antibodies shown in the legend.
Figure 27:
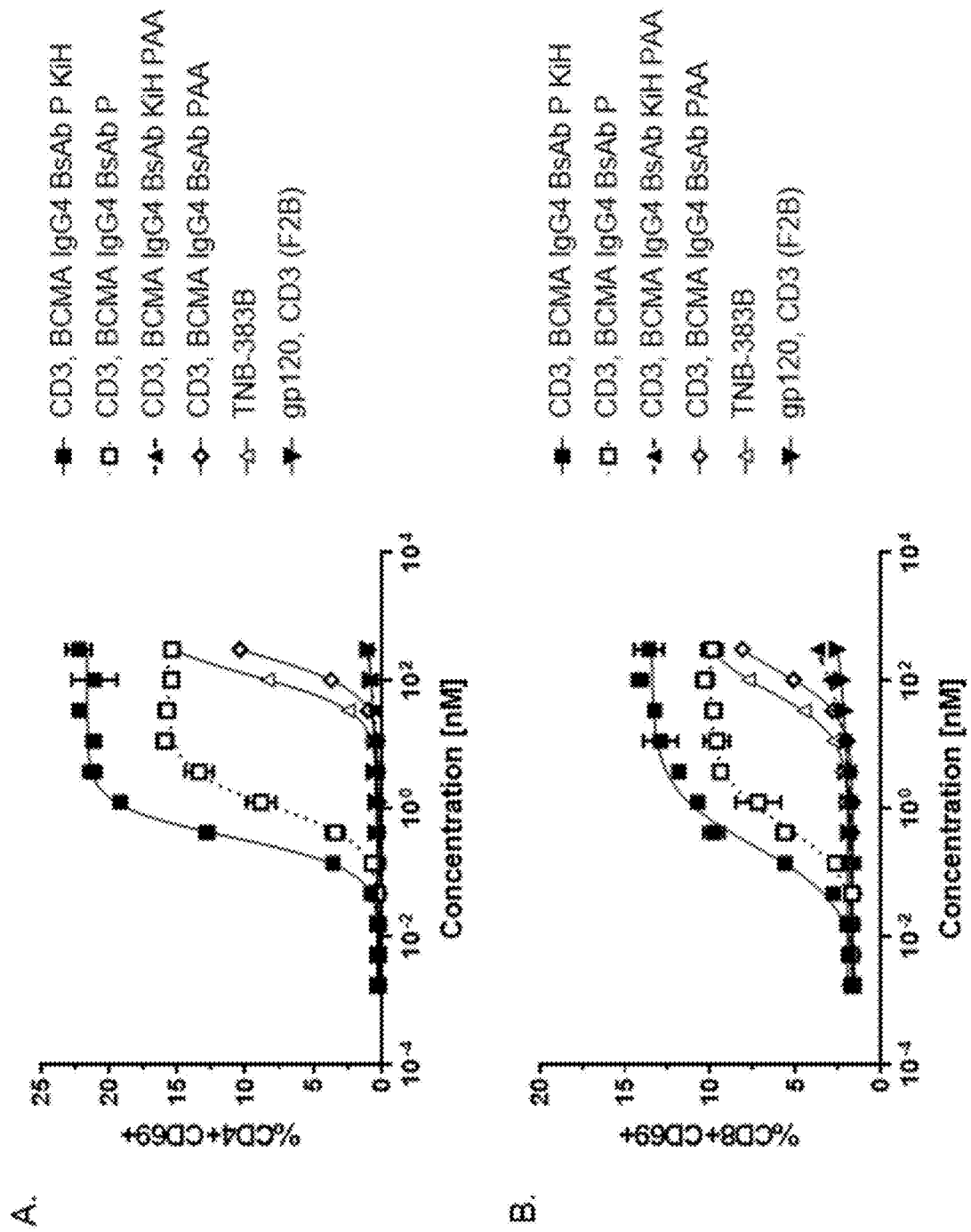
FIG. 27, panels A and B, are graphs depicting % CD4+ CD69+ T-cells (panel A) and % CD8+CD69+ T-cells (panel B) as a function of bispecific antibody concentration for the CD3×BCMA bispecific antibodies shown in the legend.
Figure 30:
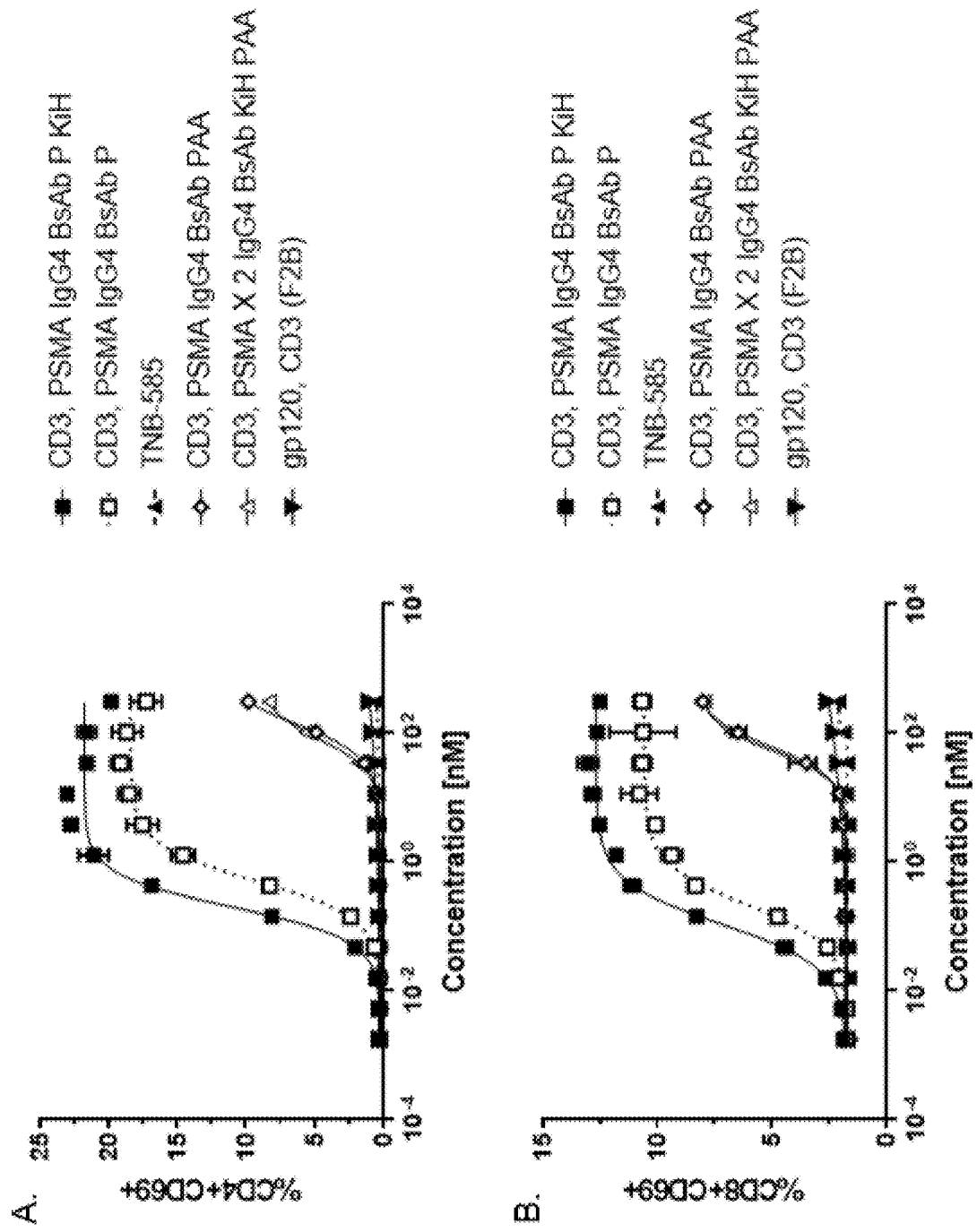
FIG. 30, panels A and B, are graphs depicting % CD4+ CD69+ T-cells (panel A) and % CD8+CD69+ T-cells (panel B) as a function of bispecific antibody concentration for the CD3×PSMA bispecific antibodies shown in the legend.

Results of T-cell activation studies are shown in the following figures: FIGS. 17-18, FIG. 27, panels A-B (without BCMA antigen coating, using PBMCs); FIG. 30, panels A-B (without PSMA coating); and FIG. 33, panels A-B (without CD19 coating).

FIG. 17 is a graph showing % CD4+CD69+ T-cells as a function of bispecific antibody concentration for the bispecific antibody constructs shown in the legend. In general, the bispecific antibodies containing IgG1 Fc sequences exhibited CD4+ T-cell activation at lower concentrations of bispecific antibody. The bispecific antibodies containing IgG4 Fc sequences exhibited CD4+ T-cell activation at higher concentrations of bispecific antibody. Notably, CD4+ T-cell activation achieved by the IgG4 Fc bispecific antibodies that contained the PAA and KiH mutations was low, demonstrating that the introduction of the PAA and KiH mutations reduces the BCMA independent activation of the T-cells by these bispecific antibodies.

FIG. 18 is a graph showing % CD8+CD69+ T-cells as a function of bispecific antibody concentration for the bispecific antibody constructs shown in the legend. As was the case for CD4+ T-cells, the bispecific antibodies containing IgG1 Fc sequences exhibited CD8+ T-cell activation at lower concentrations of bispecific antibody. The bispecific antibodies containing IgG4 Fc sequences exhibited CD8+ T-cell activation at higher concentrations of bispecific antibody. Notably, CD8+ T-cell activation achieved by the IgG4 Fc bispecific antibodies that contained the PAA and KiH mutations was low, demonstrating that the introduction of the PAA and KiH mutations reduces the BCMA independent activation of the T-cells by these bispecific antibodies.

FIG. 27, panel A, is a graph showing % CD4+CD69+ T-cells as a function of bispecific antibody concentration for the bispecific antibody constructs shown in the legend. CD4+ T-cell activation achieved by the IgG4 Fc bispecific antibodies that contained the PAA and KiH mutations was similar to the negative control (gp120, CD3 (F2B)), demonstrating that the introduction of the PAA and KiH mutations reduces the BCMA-independent activation of the T-cells by these bispecific antibodies. FIG. 27, panel B, is a graph showing % CD8+CD69+ T-cells as a function of bispecific antibody concentration for the bispecific antibody constructs shown in the legend. As was the case for CD4+ T-cells, CD8+ T-cell activation achieved by the IgG4 Fc bispecific antibodies that contained the PAA and KiH mutations was similar to the negative control, demonstrating that the introduction of the PAA and KiH mutations reduces the BCMA-independent activation of the T-cells by these bispecific antibodies.

FIG. 30, panel A, is a graph showing % CD4+CD69+ T-cells as a function of bispecific antibody concentration for the bispecific antibody constructs shown in the legend. CD4+ T-cell activation achieved by the IgG4 Fc bispecific antibodies that contained the PAA and KiH mutations was similar to the negative control (gp120, CD3 (F2B)), demonstrating that the introduction of the PAA and KiH mutations reduces the PSMA-independent activation of the T-cells by these bispecific antibodies. FIG. 30, panel B, is a graph showing % CD8+CD69+ T-cells as a function of bispecific antibody concentration for the bispecific antibody constructs shown in the legend. As was the case for CD4+ T-cells, CD8+ T-cell activation achieved by the IgG4 Fc bispecific antibodies that contained the PAA and KiH mutations was similar to the negative control, demonstrating that the introduction of the PAA and KiH mutations reduces the PSMA-independent activation of the T-cells by these bispecific antibodies.

Figure 33:
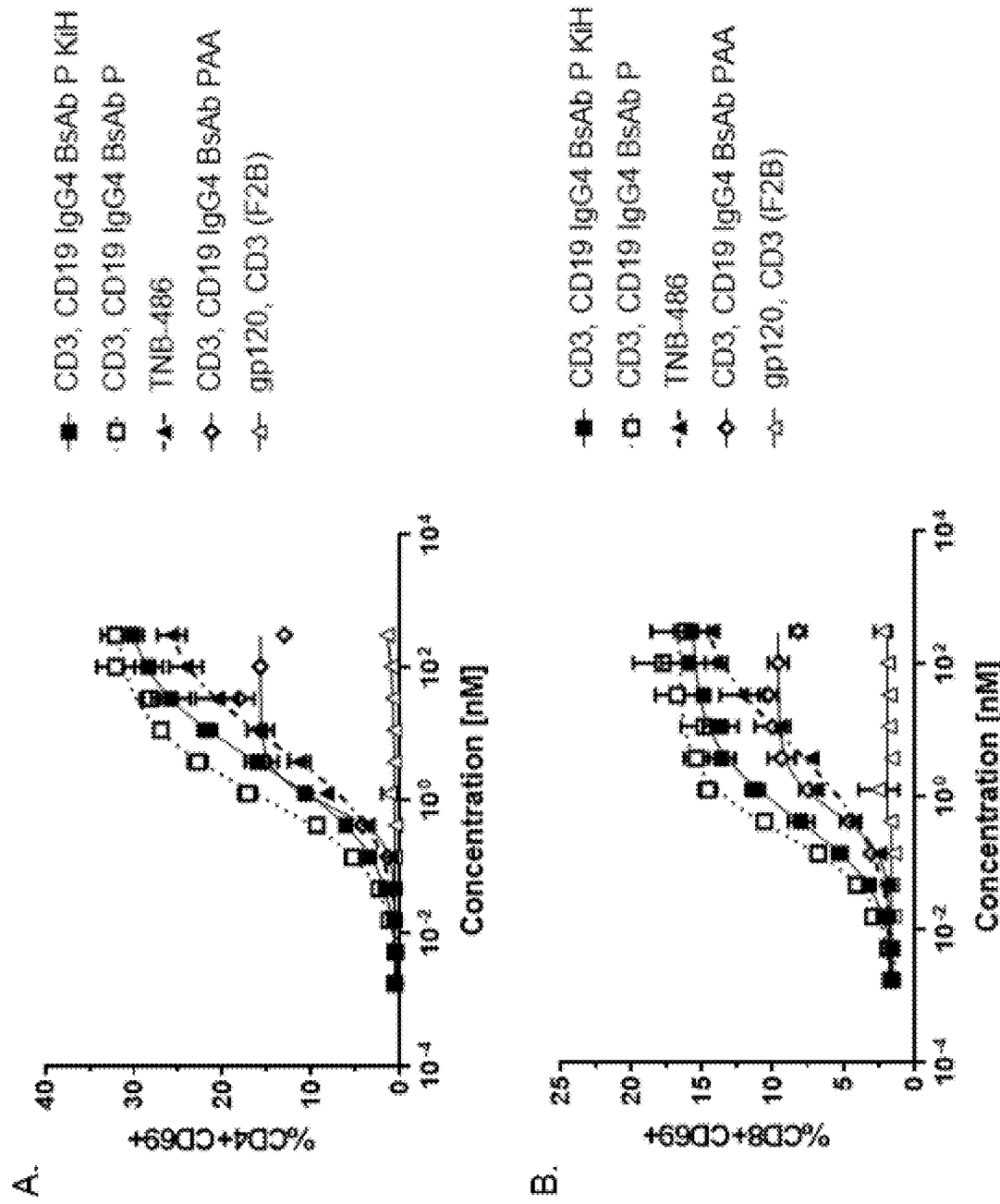
FIG. 33, panels A and B, are graphs depicting % CD4+ CD69+ T-cells (panel A) and % CD8+CD69+ T-cells (panel B) as a function of bispecific antibody concentration for the CD3×CD19 bispecific antibodies shown in the legend.

FIG. 33, panel A, is a graph showing % CD4+CD69+ T-cells as a function of bispecific antibody concentration for the bispecific antibody constructs shown in the legend. CD4+ T-cell activation achieved by the IgG4 Fc bispecific antibodies that contained the PAA and KiH mutations was much lower than what was observed from other antibody constructs that did not contain the PAA and KiH mutations, demonstrating that the introduction of the PAA and KiH mutations reduces the CD19-independent activation of the T-cells by these bispecific antibodies. FIG. 33, panel B, is a graph showing % CD8+CD69+ T-cells as a function of bispecific antibody concentration for the bispecific antibody constructs shown in the legend. As was the case for CD4+ T-cells, CD8+ T-cell activation achieved by the IgG4 Fc bispecific antibodies that contained the PAA and KiH mutations was much lower than what was observed from other antibody constructs that did not contain the PAA and KiH mutations, demonstrating that the introduction of the PAA and KiH mutations reduces the CD19-independent activation of the T-cells by these bispecific antibodies.

Figure 19:
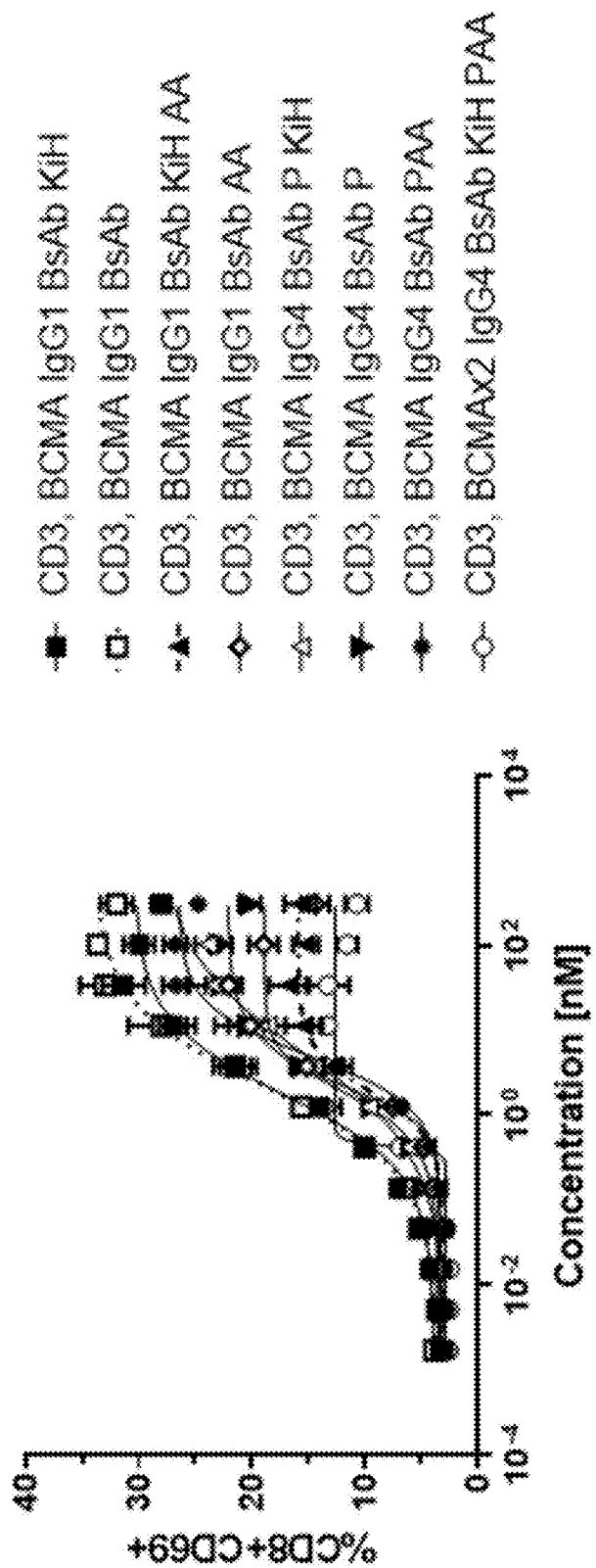
FIG. 19 is a graph depicting % CD8+CD69+ T-cells as a function of bispecific antibody concentration for the bispecific antibodies shown in the legend.
Figure 28:
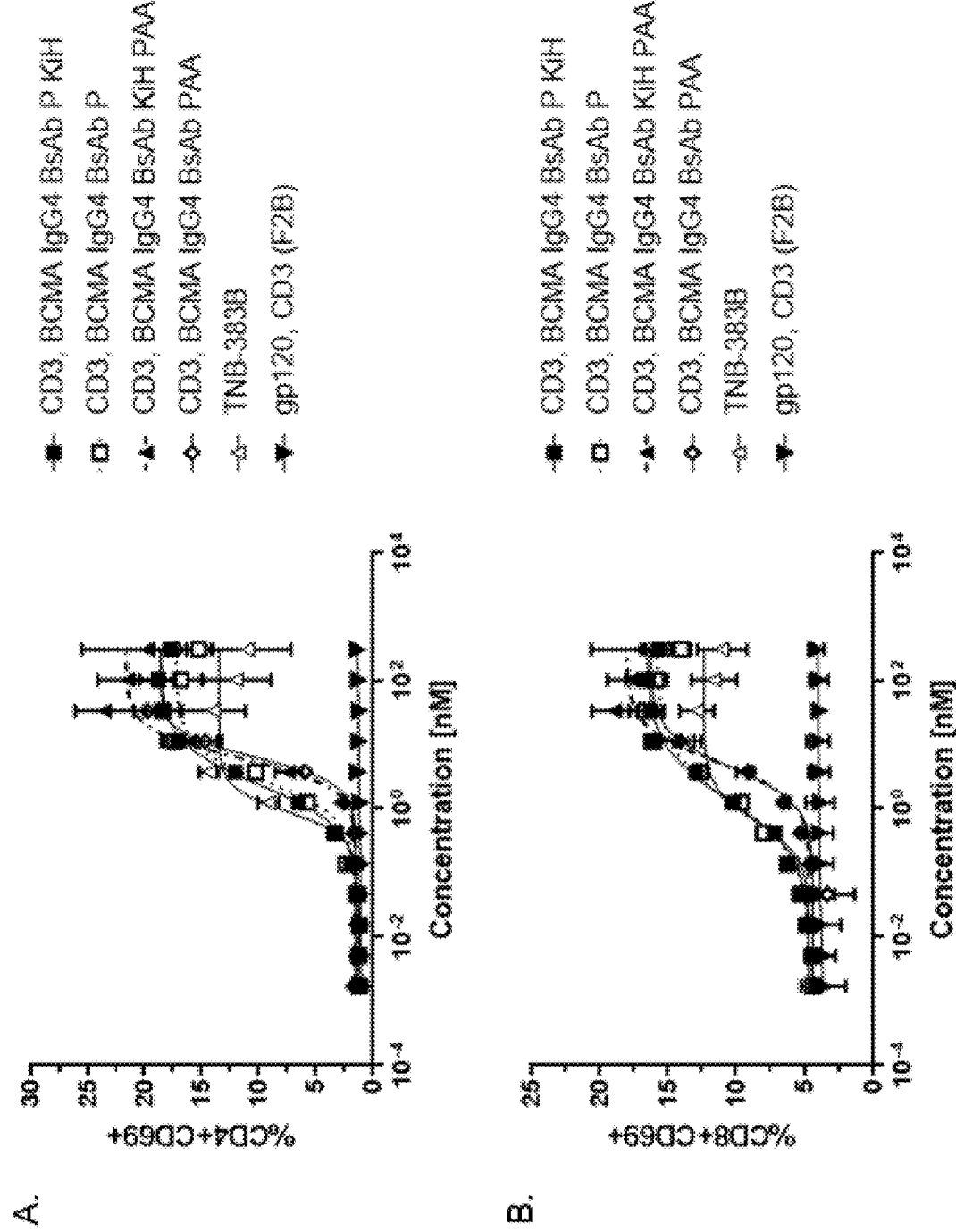
FIG. 28, panels A and B, are graphs depicting % CD4+ CD69+ T-cells (panel A) and % CD8+CD69+ T-cells (panel B) as a function of bispecific antibody concentration for the CD3×BCMA bispecific antibodies shown in the legend.
Figure 31:
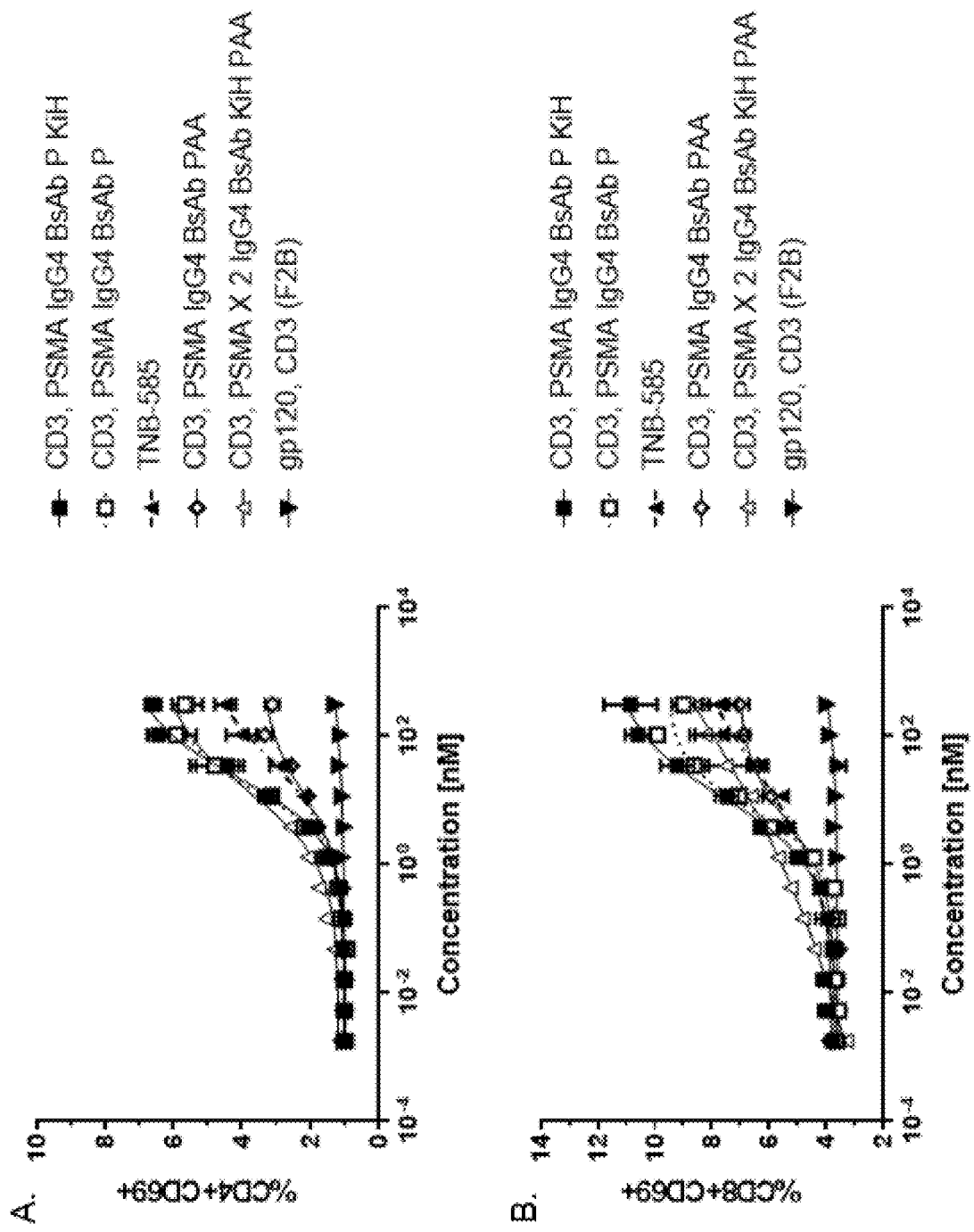
FIG. 31, panels A and B, are graphs depicting % CD4+ CD69+ T-cells (panel A) and % CD8+CD69+ T-cells (panel B) as a function of bispecific antibody concentration for the CD3×PSMA bispecific antibodies shown in the legend.
Figure 34:
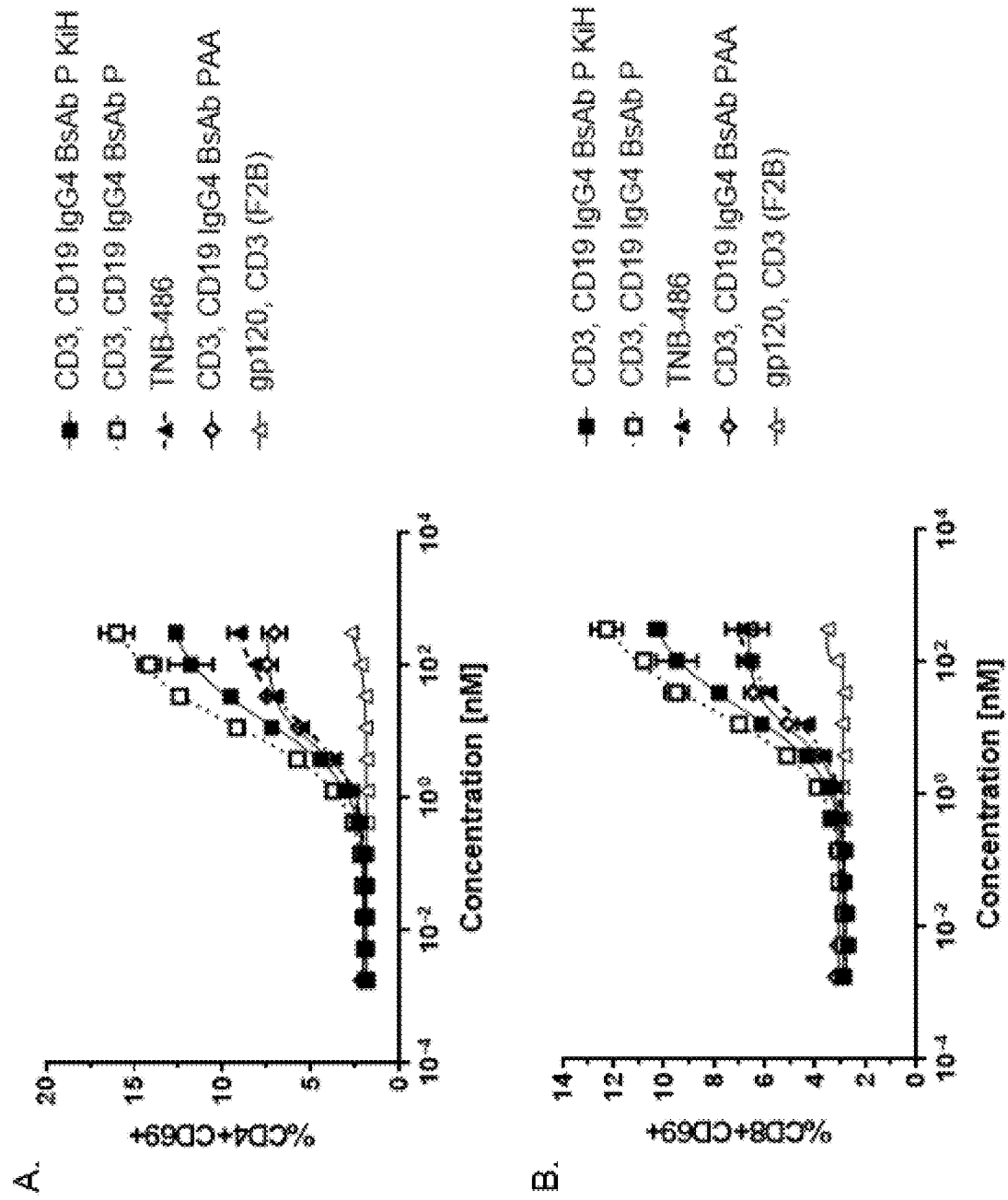
FIG. 34, panels A and B, are graphs depicting % CD4+ CD69+ T-cells (panel A) and % CD8+CD69+ T-cells (panel B) as a function of bispecific antibody concentration for the CD3×CD19 bispecific antibodies shown in the legend.

Results of CD8+ T-cell activation with antigen coating using pan T-cells isolated from resting PBMCs are provided in FIG. 19, FIG. 28, panel B, FIG. 31, panel B, and FIG. 34, panel B. Results of CD4+T-cell activation with antigen coating using pan T-cells isolated from resting PBMCs are provided in FIG. 28, panel A, FIG. 31, panel A, and FIG. 34, panel A. The antigen coating concentration for BCMA and PSMA was 1 µg/mL, whereas the antigen coating concentration for CD19 was 10 µg/mL.

FIG. 19 is a graph showing % CD8+CD69+ T-cells as a function of bispecific antibody concentration for the bispecific antibody constructs shown in the legend. Unlike the case for the experiments without BCMA coating, all the bispecific antibodies exhibited CD8+ T-cell activation at similar concentrations of bispecific antibody for the antigen coated cells. Notably, CD8+ T-cell activation was achieved by the IgG4 Fc bispecific antibodies that contained the PAA and KiH mutations, demonstrating that the introduction of the PAA and KiH mutations did not eliminate the CD8+ T-cell activation activity of these molecules.

FIG. 28, panel B, is a graph showing % CD8+CD69+ T-cells as a function of bispecific antibody concentration for the bispecific antibody constructs shown in the legend. Unlike the case for the experiments without BCMA coating, all the bispecific antibodies exhibited CD8+ T-cell activation at similar concentrations of bispecific antibody for the antigen coated cells. Notably, CD8+ T-cell activation was achieved by the IgG4 Fc bispecific antibodies that contained the PAA and KiH mutations, demonstrating that the introduction of the PAA and KiH mutations did not eliminate the CD8+ T-cell activation activity of these molecules.

FIG. 31, panel B, is a graph showing % CD8+CD69+ T-cells as a function of bispecific antibody concentration for the bispecific antibody constructs shown in the legend. Unlike the case for the experiments without PSMA coating, all the bispecific antibodies exhibited CD8+ T-cell activation at similar concentrations of bispecific antibody for the antigen coated cells. Notably, CD8+ T-cell activation was achieved by the IgG4 Fc bispecific antibodies that contained the PAA and KiH mutations, demonstrating that the introduction of the PAA and KiH mutations did not eliminate the CD8+ T-cell activation activity of these molecules.

FIG. 34, panel B, is a graph showing % CD8+CD69+ T-cells as a function of bispecific antibody concentration for the bispecific antibody constructs shown in the legend. Unlike the case for the experiments without CD19 coating, all the bispecific antibodies exhibited CD8+ T-cell activation at similar concentrations of bispecific antibody for the antigen coated cells. Notably, CD8+ T-cell activation was achieved by the IgG4 Fc bispecific antibodies that contained the PAA and KiH mutations, demonstrating that the introduction of the PAA and KiH mutations did not eliminate the CD8+ T-cell activation activity of these molecules.

FIG. 28, panel A, is a graph showing % CD4+CD69+ T-cells as a function of bispecific antibody concentration for the bispecific antibody constructs shown in the legend. Unlike the case for the experiments without BCMA coating, all the bispecific antibodies exhibited CD4+ T-cell activation at similar concentrations of bispecific antibody for the antigen coated cells. Notably, CD4+ T-cell activation was achieved by the IgG4 Fc bispecific antibodies that contained the PAA and KiH mutations, demonstrating that the introduction of the PAA and KiH mutations did not eliminate the CD4+ T-cell activation activity of these molecules.

FIG. 31, panel A, is a graph showing % CD4+CD69+ T-cells as a function of bispecific antibody concentration for the bispecific antibody constructs shown in the legend. Unlike the case for the experiments without PSMA coating, all the bispecific antibodies exhibited CD4+ T-cell activation at similar concentrations of bispecific antibody for the antigen coated cells. Notably, CD4+ T-cell activation was achieved by the IgG4 Fc bispecific antibodies that contained the PAA and KiH mutations, demonstrating that the introduction of the PAA and KiH mutations did not eliminate the CD4+ T-cell activation activity of these molecules.

FIG. 34, panel A, is a graph showing % CD4+CD69+ T-cells as a function of bispecific antibody concentration for the bispecific antibody constructs shown in the legend. Unlike the case for the experiments without CD19 coating, all the bispecific antibodies exhibited CD4+ T-cell activation at similar concentrations of bispecific antibody for the antigen coated cells. Notably, CD4+ T-cell activation was achieved by the IgG4 Fc bispecific antibodies that contained the PAA and KiH mutations, demonstrating that the introduction of the PAA and KiH mutations did not eliminate the CD4+ T-cell activation activity of these molecules.

Figure 20:
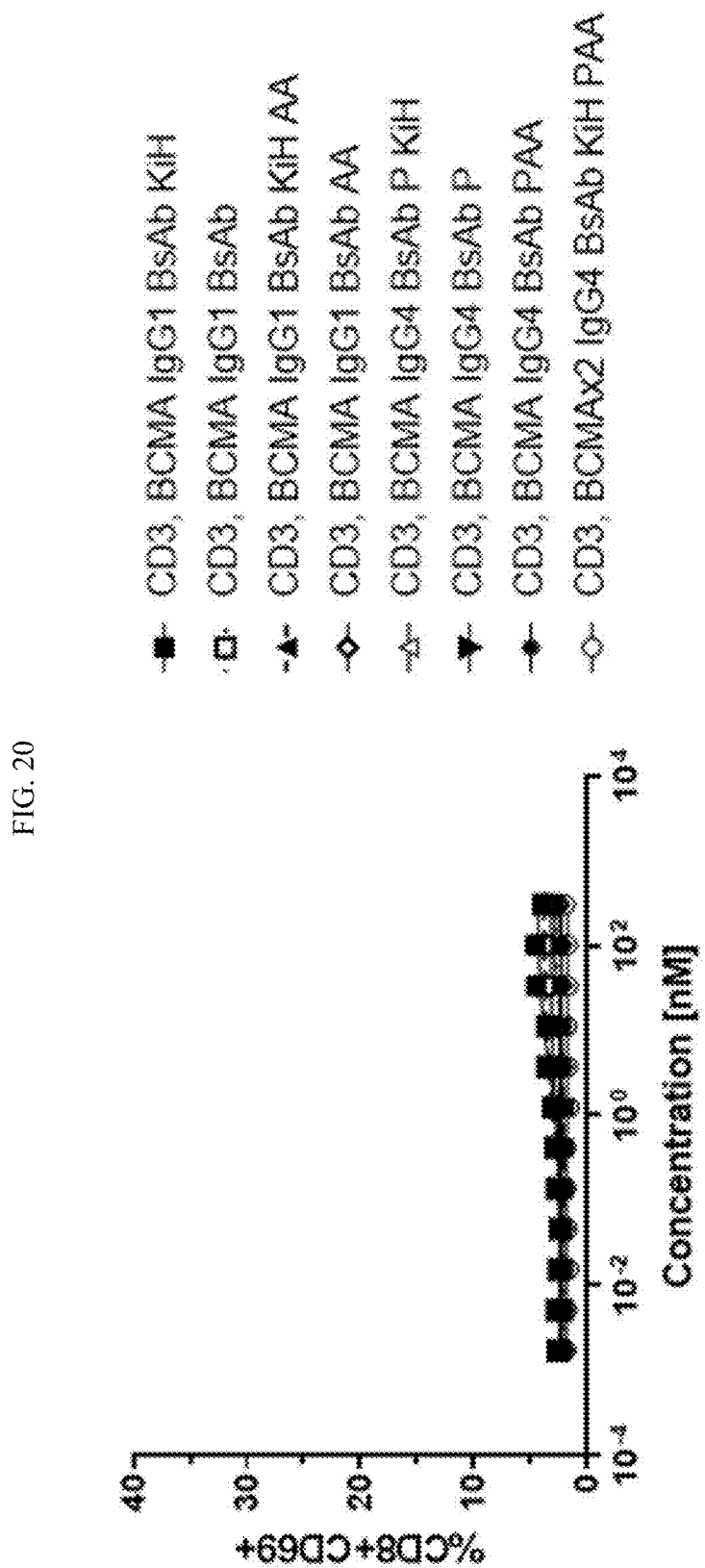
FIG. 20 is a graph depicting % CD8+CD69+ T-cells as a function of bispecific antibody concentration for the bispecific antibodies shown in the legend.
Figure 29:
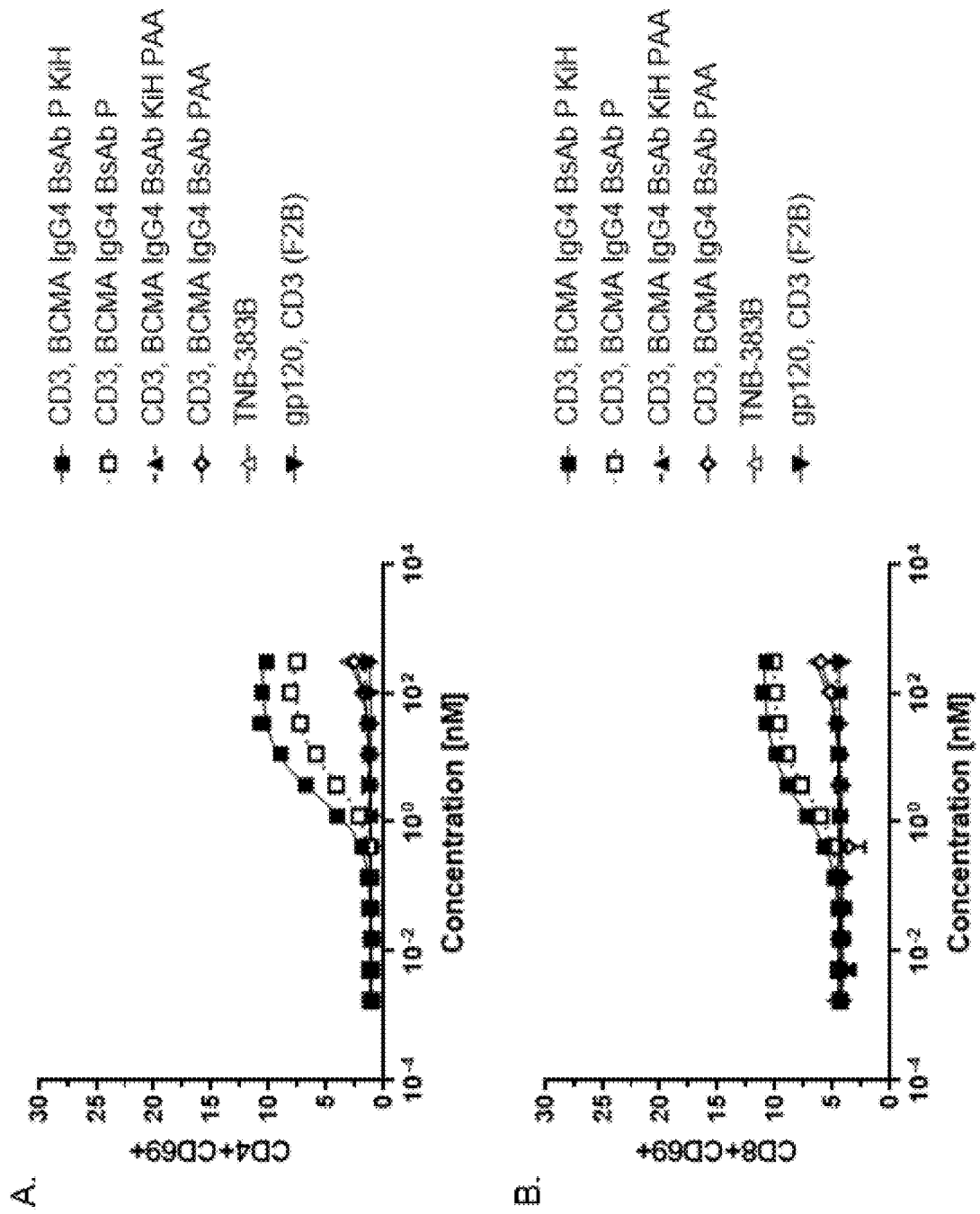
FIG. 29, panels A and B, are graphs depicting % CD4+ CD69+ T-cells (panel A) and % CD8+CD69+ T-cells (panel B) as a function of bispecific antibody concentration for the CD3×BCMA bispecific antibodies shown in the legend.
Figure 32:
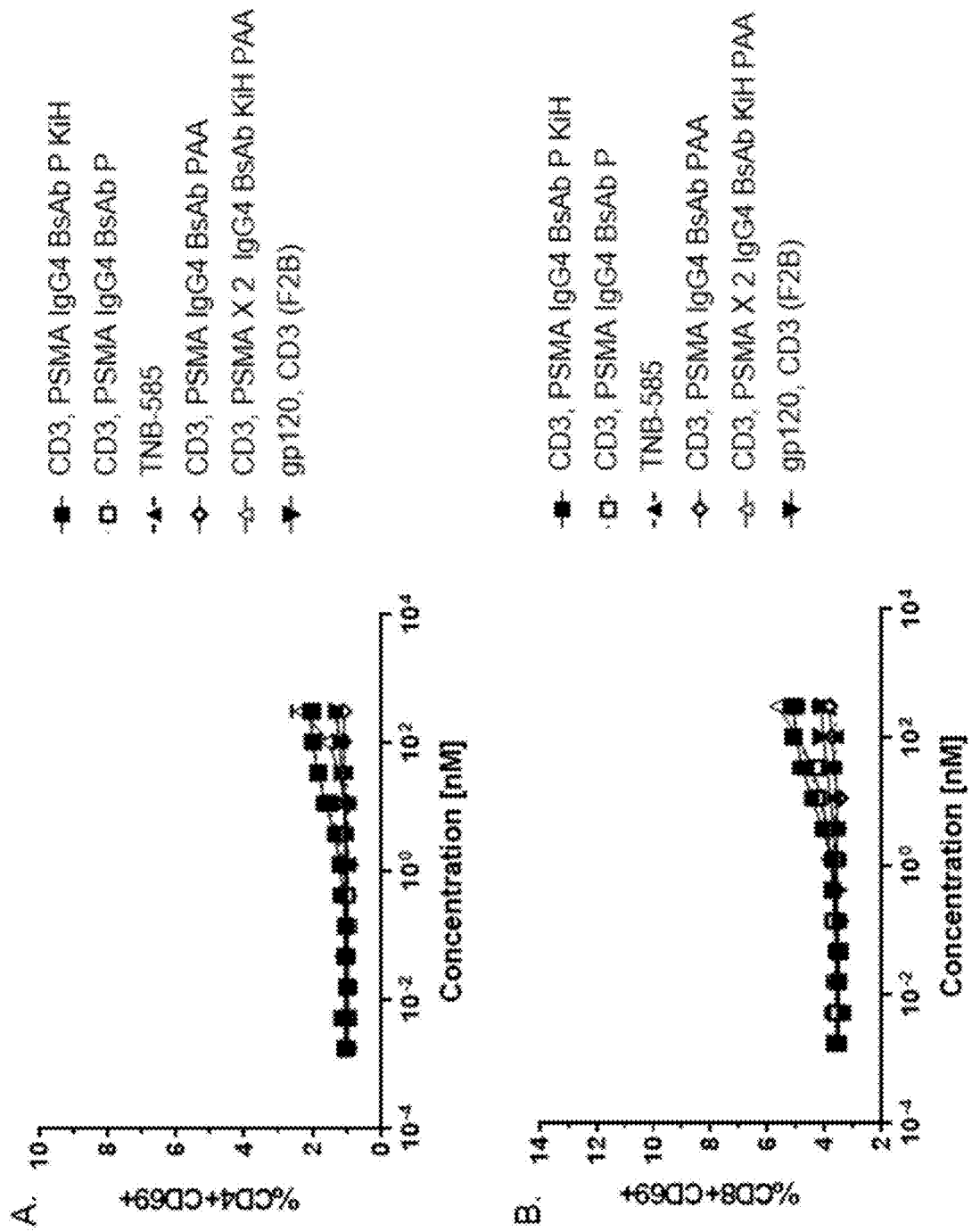
FIG. 32, panels A and B, are graphs depicting % CD4+ CD69+ T-cells (panel A) and % CD8+CD69+ T-cells (panel B) as a function of bispecific antibody concentration for the CD3×PSMA bispecific antibodies shown in the legend.
Figure 35:
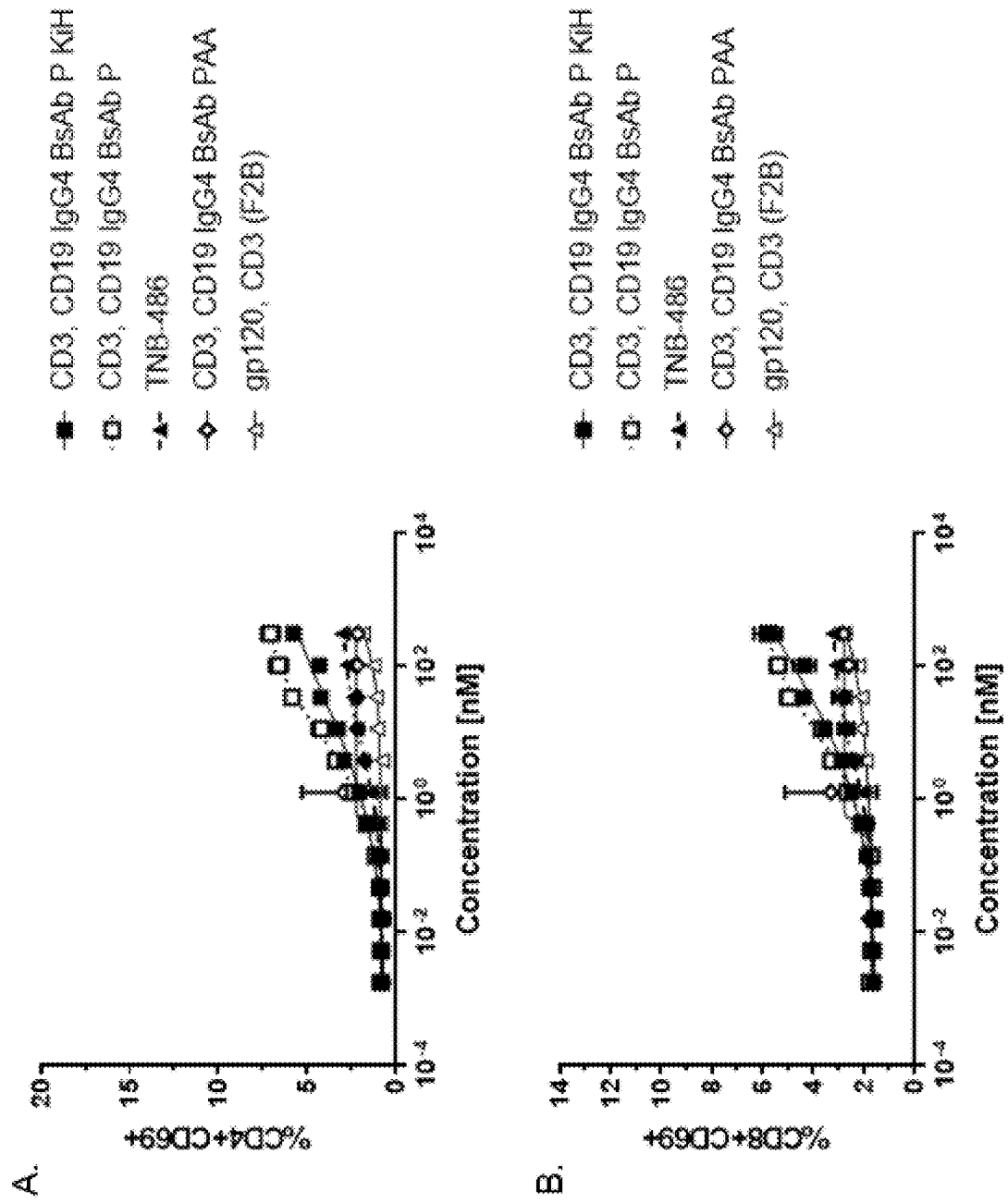
FIG. 35, panels A and B, are graphs depicting % CD4+ CD69+ T-cells (panel A) and % CD8+CD69+ T-cells (panel B) as a function of bispecific antibody concentration for the CD3×CD19 bispecific antibodies shown in the legend.

Results of CD8+ T-cell activation without antigen coating using pan T-cells isolated from resting PBMCs are provided in FIG. 20, FIG. 29, panel B, FIG. 32, panel B, and FIG. 35, panel B. Results of CD4+ T-cell activation without antigen coating using pan T-cells isolated from resting PBMCs are provided in FIG. 29, panel A, FIG. 32, panel A, and FIG. 35, panel A.

FIG. 20 is a graph showing % CD8+CD69+ T-cells as a function of bispecific antibody concentration for the bispecific antibody constructs shown in the legend. These results demonstrate that CD69 activation in CD8+ T-cells is BCMA dependent for all the bispecific antibody molecules tested.

FIG. 29, panels A and B, are graphs showing % CD4+CD69+ and % CD8+CD69+ T-cells, respectively, as a function of bispecific antibody concentration for the bispecific antibody constructs shown in the legend. These results demonstrate that CD69 activation in CD4+ and CD8+ T-cells is BCMA dependent for all the bispecific antibody molecules tested. CD69 activation was slightly increased in both CD4+ and CD8+ T-cells at higher concentrations of the bispecific antibody constructs that did not include silencing mutations.

FIG. 32, panels A and B, are graphs showing % CD4+CD69+ and % CD8+CD69+ T-cells, respectively, as a function of bispecific antibody concentration for the bispecific antibody constructs shown in the legend. These results demonstrate that CD69 activation in CD4+ and CD8+ T-cells is PSMA dependent for all the bispecific antibody molecules tested.

FIG. 35, panels A and B, are graphs showing % CD4+CD69+ and % CD8+CD69+ T-cells, respectively, as a function of bispecific antibody concentration for the bispecific antibody constructs shown in the legend. These results demonstrate that CD69 activation in CD4+ and CD8+ T-cells is CD19 dependent for all the bispecific antibody molecules tested. CD69 activation was slightly increased in both CD4+ and CD8+ T-cells at higher concentrations of the bispecific antibody constructs that did not include silencing mutations.

Example 10: Lysis of Tumor Cells

Figure 21:
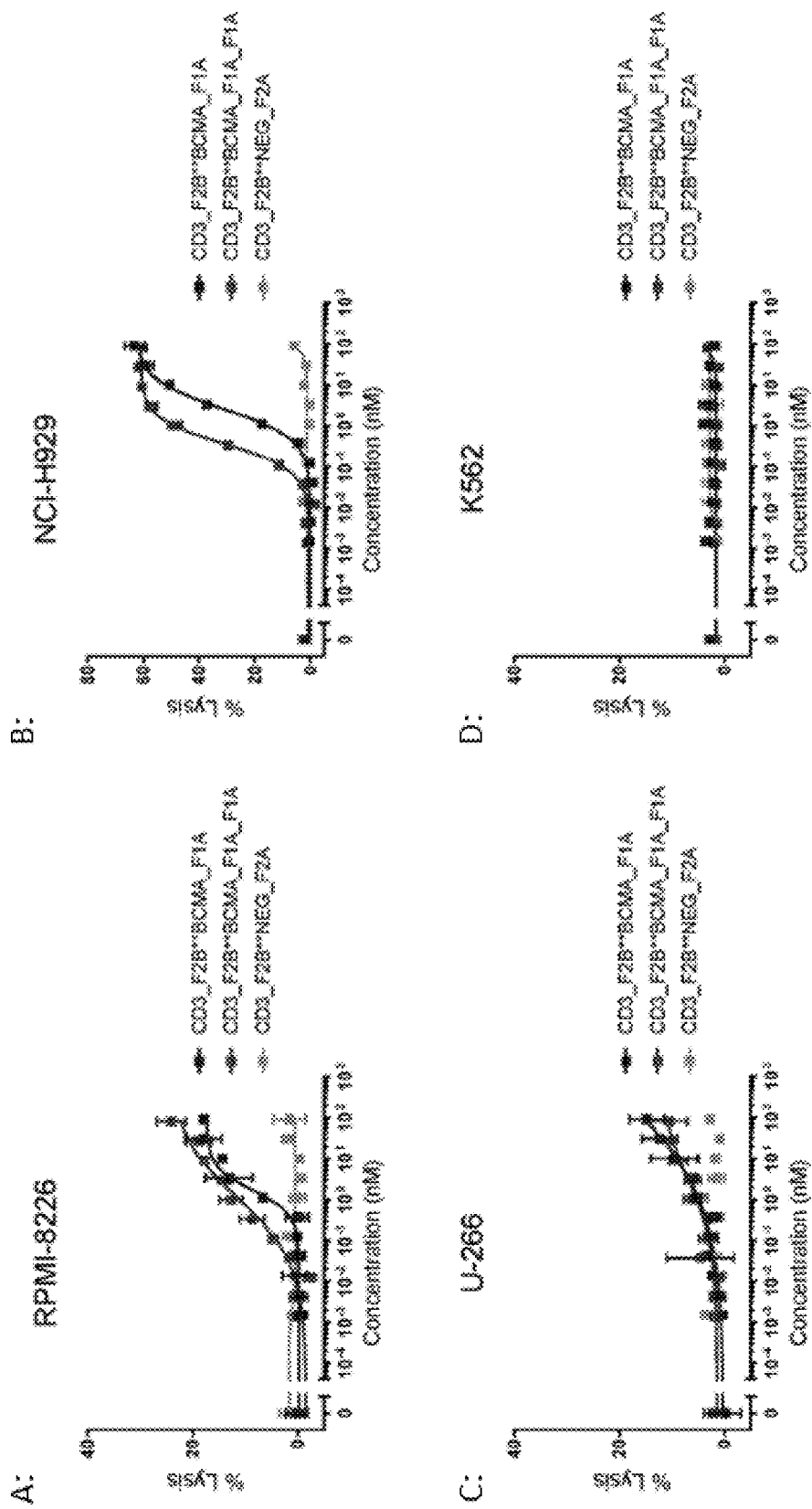
FIG. 21, panels A-D, provide several graphs depicting bispecific antibody-mediated tumor cell lysis. Anti-CD3× anti-BCMA bispecific antibodies were assayed for the ability to kill three different BCMA+ tumor cells and one BCMA-negative cell line through redirection of activated primary T-cells. In this experiment, tumor cells were mixed with activated pan T-cells in a 10:1 E:T ratio along with the addition of bispecific antibody. Panel A shows killing of RPMI-8226 cells, panel B shows killing of NCI-H929 cells, panel C shows killing of U-266 cells, and panel D shows killing of K562 cells, a negative control. The x-axis shows the concentration of antibody used and the y-axis shows the % lysis of tumor cells 6 hours after addition of antibody.

Anti-CD3× anti-BCMA bispecific antibodies were assayed for the ability to kill three different BCMA+ tumor cells and one BCMA-negative cell line through redirection of activated primary T-cells. In this experiment, tumor cells were mixed with activated pan T-cells in a 10:1 E:T ratio along with the addition of bispecific antibody. The results are shown in FIG. 21, Panels A-D. Panel A shows killing of RPMI-8226 cells, panel B shows killing of NCI-H929 cells, panel C shows killing of U-266 cells, and panel D shows killing of K562 cells, a negative control. The x-axis shows the concentration of antibody used and the y-axis shows the % lysis of tumor cells 6 hours after addition of antibody.

Figure 22:
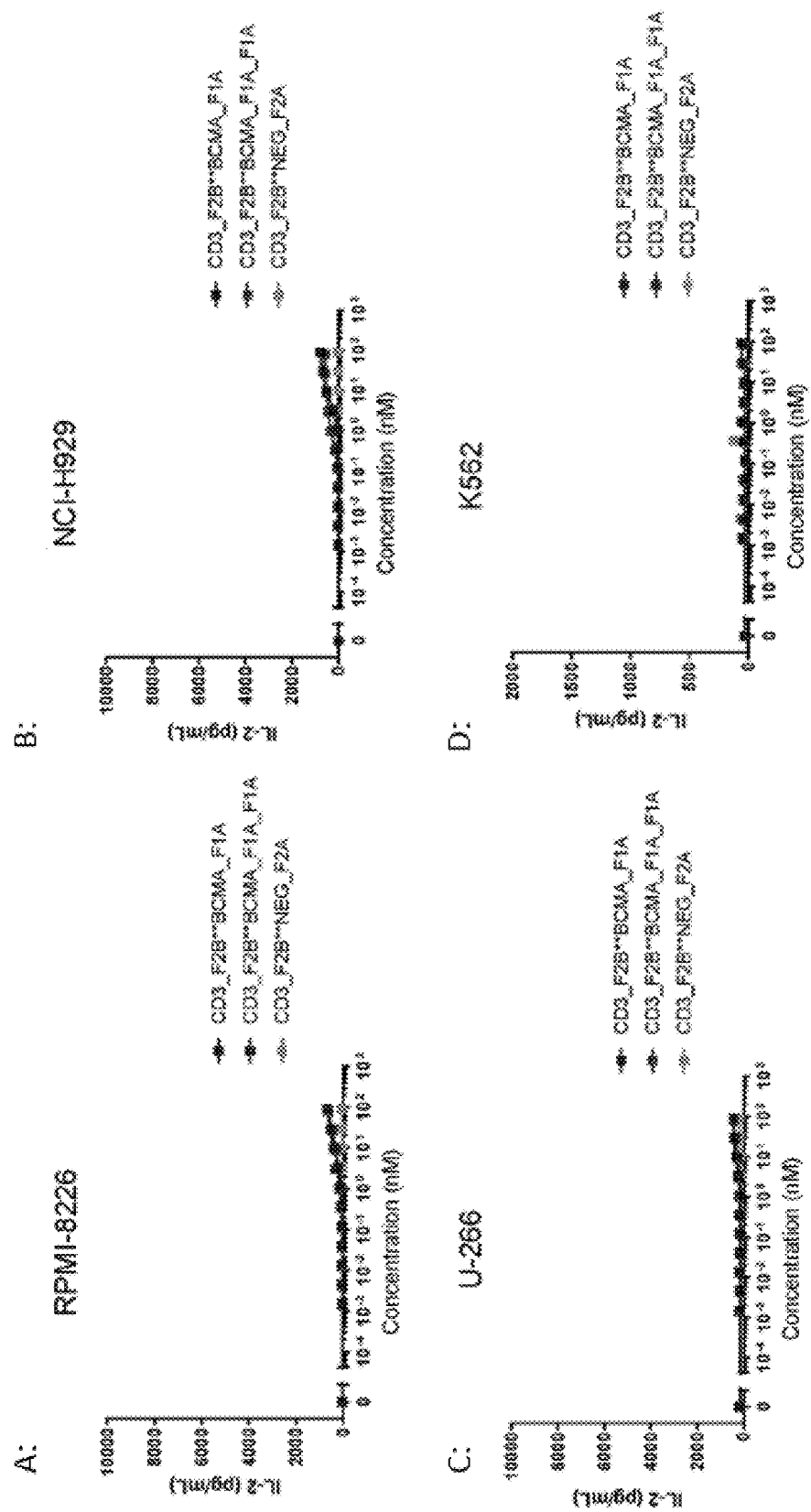
FIG. 22, panels A-D, provide several graphs depicting bispecific antibody-mediated IL-2 release. The level of IL-2 cytokine release was measured after resting human T-cells were cultured with various tumor cell lines and increasing doses of anti-CD3× anti-BCMA bispecific antibody. Panel A shows IL-2 release stimulated by RPMI-8226 cells, panel B shows IL-2 release stimulated by NCI-H929 cells, panel C shows IL-2 release stimulated by U-266 cells, and panel D shows IL-2 release stimulated by K562 cells, a negative control.

The level of IL-2 cytokine release was measured after resting human T-cells were cultured with various tumor cell lines and increasing doses of anti-CD3× anti-BCMA bispecific antibody. FIG. 22, panel A shows IL-2 release stimulated by RPMI-8226 cells, FIG. 22, panel B shows IL-2 release stimulated by NCI-H929 cells. FIG. 22, panel C shows IL-2 release stimulated by U-266 cells, and FIG. 22, panel D shows IL-2 release stimulated by K562 cells, a negative control.

Figure 23:
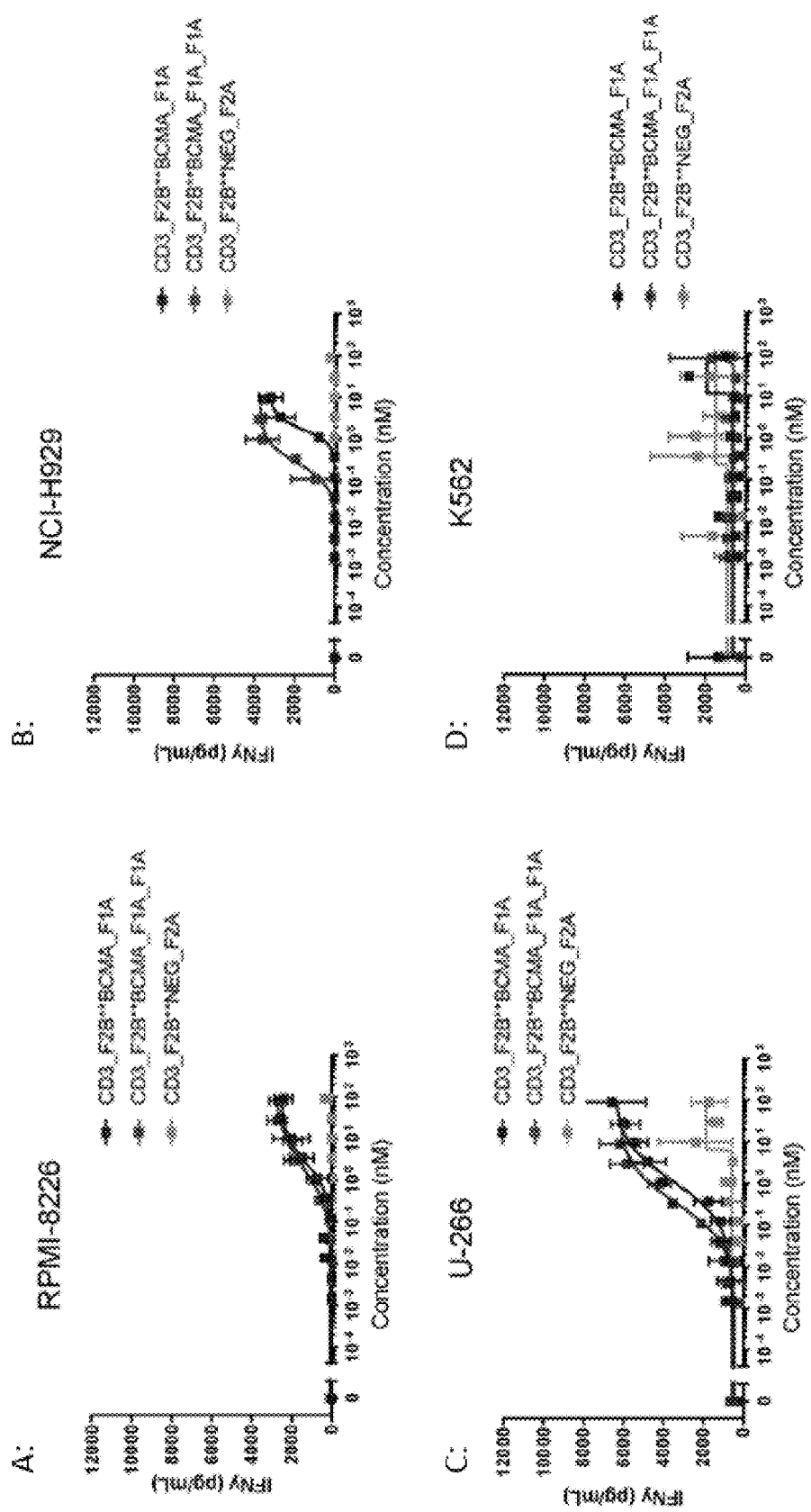
FIG. 23, panels A-D, provide several graphs depicting bispecific antibody-mediated IFN-γ release. The level of IFN-γ cytokine release was measured after resting human T-cells were cultured with various tumor cell lines and increasing doses of anti-CD3× anti-BCMA bispecific antibody. Panel A shows IFN-γ release stimulated by RPMI-8226 cells, panel B shows IFN-γ release stimulated by NCI-H929 cells, panel C shows IFN-γ release stimulated by U-266 cells, and panel D shows IFN-γ release stimulated by K562 cells, a negative control.

The level of IFN-γ cytokine release was measured after resting human T-cells were cultured with various tumor cell lines and increasing doses of anti-CD3× anti-BCMA bispecific antibody. FIG. 23, panel A shows IFN-γ release stimulated by RPMI-8226 cells, FIG. 23, panel B shows IFN-γ release stimulated by NCI-H929 cells, FIG. 23, panel C shows IFN-γ release stimulated by U-266 cells, and FIG. 23, panel D shows IFN-γ release stimulated by K562 cells, a negative control.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A bispecific monoclonal antibody that binds to human CD3 and human BCMA, comprising:
   (i) a first polypeptide subunit comprising the amino acid sequence of SEQ ID NO: 49;
   (ii) a second polypeptide subunit comprising the amino acid sequence of SEQ ID NO: 56,
      wherein the first and second polypeptide subunits together form a first binding moiety that binds to human CD3; and
   (iii) a third polypeptide subunit that binds to human BCMA, comprising the amino acid sequence of SEQ ID NO: 58.

2. The bispecific monoclonal antibody of claim 1, wherein the first polypeptide subunit comprises a light chain.

3. The bispecific monoclonal antibody of claim 1, wherein the second polypeptide subunit comprises a heavy chain.

4. The bispecific monoclonal antibody of claim 1, wherein the third polypeptide subunit comprises a bivalent heavy chain.

5. The bispecific monoclonal antibody of claim 4, wherein the bivalent heavy chain comprises a heavy chain-only variable region in a bivalent configuration.

6. The bispecific monoclonal antibody of claim 4, wherein the bivalent heavy chain lacks a CH1 domain.

7. A bispecific monoclonal antibody that binds to human CD3 and human BCMA, comprising:
   (i) a first polypeptide subunit comprising the amino acid sequence of SEQ ID NO: 49;
   (ii) a second polypeptide subunit comprising the amino acid sequence of SEQ ID NO: 75,
      wherein the first and second polypeptide subunits together form a first binding moiety that binds to human CD3; and
   (iii) a third polypeptide subunit that binds to human BCMA, comprising the amino acid sequence of SEQ ID NO: 76.

8. The bispecific monoclonal antibody of claim 7, wherein the first polypeptide subunit comprises a light chain.

9. The bispecific monoclonal antibody of claim 7, wherein the second polypeptide subunit comprises a heavy chain.

10. The bispecific monoclonal antibody of claim 7, wherein the third polypeptide subunit comprises a bivalent heavy chain.

11. The bispecific monoclonal antibody of claim 10, wherein the bivalent heavy chain comprises a heavy chain-only variable region in a bivalent configuration.

12. The bispecific monoclonal antibody of claim 10, wherein the bivalent heavy chain lacks a CH1 domain.

13. A human, monoclonal IgG4 bispecific antibody comprising:
   (i) a first binding arm that binds to human CD3; and
   (ii) a second binding arm that binds to human BCMA,
      wherein the first binding arm comprises a first heavy chain comprising the amino acid sequence of SEQ ID NO: 56 and a light chain comprising the amino acid sequence of SEQ ID NO: 49; and
      wherein the second binding arm comprises a bivalent second heavy chain comprising the amino acid sequence of SEQ ID NO: 58.

14. The human, monoclonal IgG4 bispecific antibody of claim 13, wherein the second binding arm does not comprise a light chain.

15. The human, monoclonal IgG4 bispecific antibody of claim 13, wherein the bivalent second heavy chain comprises a heavy chain-only variable region in a bivalent configuration.

16. The human, monoclonal IgG4 bispecific antibody of claim 13, wherein the bivalent second heavy chain lacks a CH1 domain.

17. A human, monoclonal IgG4 bispecific antibody comprising:
   (i) a first binding arm that binds to human CD3; and
   (ii) a second binding arm that binds to human BCMA,
      wherein the first binding arm comprises a first heavy chain comprising the amino acid sequence of SEQ ID NO: 75 and a light chain comprising the amino acid sequence of SEQ ID NO: 49; and
      wherein the second binding arm comprises a bivalent second heavy chain comprising the amino acid sequence of SEQ ID NO: 76.

18. The human, monoclonal IgG4 bispecific antibody of claim 17, wherein the second binding arm does not comprise a light chain.

19. The human, monoclonal IgG4 bispecific antibody of claim 17, wherein the bivalent second heavy chain comprises a heavy chain-only variable region in a bivalent configuration.

20. The human, monoclonal IgG4 bispecific antibody of claim 17, wherein the bivalent second heavy chain lacks a CH1 domain.

* * * * *

SEQUENCE LISTING

<160> NUMBER OF SEQ ID NOS: 92

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Asp Tyr Ser Gly Tyr Thr Tyr Tyr Asn Pro Ser
    50                  55                  60

Leu Gln Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser
        115                 120

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Phe Trp Gly Trp Ile Arg Gln Ser Pro Gly Lys Gly Leu Glu
        35                  40                  45

Trp Ile Gly Ser Ile Asp Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser
        115                 120

<210> SEQ ID NO 3
<211> LENGTH: 120
<212> TYPE: PRT
<213> ORGANISM: Artificial Sequence
<220> FEATURE:
<223> OTHER INFORMATION: Description of Artificial Sequence: Synthetic -continued

```
        polypeptide

<400> SEQUENCE: 3

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Val Asp Tyr Ser Gly Tyr Thr Tyr Tyr Asn Pro Ser
    50                  55                  60

Leu Gln Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser
        115                 120

<210> SEQ ID NO 4
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Asp Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser
        115                 120

<210> SEQ ID NO 5
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asn
            20                  25                  30
```

```
Ser Tyr Tyr Trp Gly Trp Ile Arg Gln Ser Pro Gly Lys Gly Leu Glu
            35                  40                  45

Trp Leu Gly Ser Ile Tyr Asp Ser Gly Ser Thr His Tyr Asn Pro Ser
 50                  55                  60

Leu Lys Ser Arg Val Ile Ile Ser Gly Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg His Lys Ala Ala Thr Ala Asp Phe Asp Tyr Arg Gly Gln
                100                 105                 110

Gly Thr Leu Val Thr Val Ser Ser
            115                 120
```

<210> SEQ ID NO 6
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Arg Ser Tyr
                 20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Tyr Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Pro Arg Ile Gly Tyr Tyr Tyr Glu Ser Ser Gly Tyr Asp
                100                 105                 110

Ser Leu Asp Tyr Arg Gly Gln Gly Thr Leu Val Thr Val Ser Ser
            115                 120                 125
```

<210> SEQ ID NO 7
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Ser Tyr
                 20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Tyr Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Asp
            100                 105                 110

Ser Leu Asp Tyr Arg Gly Gln Gly Thr Leu Val Thr Val Ser Ser
        115                 120                 125

<210> SEQ ID NO 8
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 9
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Arg Ser Tyr
            20                  25                  30

Gly Met His Trp Val Arg Gln Ala Pro Gly Lys Gly Pro Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125
```

```
<210> SEQ ID NO 10
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Tyr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Asp Ser Ser Gly Tyr Asp
            100                 105                 110

Ser Leu Asp Tyr Arg Gly Gln Gly Thr Leu Val Thr Val Ser Ser
        115                 120                 125

<210> SEQ ID NO 11
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Arg Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Asp Ser Ser Gly Tyr Asp
            100                 105                 110

Ser Leu Asp Tyr Arg Gly Gln Gly Thr Leu Val Thr Val Ser Ser
        115                 120                 125

<210> SEQ ID NO 12
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 12

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Arg Ser Tyr
            20                  25                  30

Gly Met His Trp Val Arg Gln Ala Pro Gly Lys Gly Pro Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Asp Ser Ser Gly Tyr Asp
            100                 105                 110

Ser Leu Asp Tyr Arg Gly Gln Gly Thr Leu Val Thr Val Ser Ser
        115                 120                 125

<210> SEQ ID NO 13
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Asp Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 14
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Arg Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Tyr Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Asp Ser Ser Gly Tyr Asp
                100                 105                 110

Ser Leu Asp Tyr Arg Gly Gln Gly Thr Leu Val Thr Val Ser Ser
                115                 120                 125

<210> SEQ ID NO 15
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Arg Tyr
                20                  25                  30

Gly Met His Trp Val Arg Gln Ala Pro Gly Lys Gly Leu Glu Gly Val
            35                  40                  45

Ala Val Ile Trp Tyr Asp Gly Ser Asn Arg Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
                100                 105                 110

Ser Leu Asp Tyr Arg Gly Gln Gly Thr Leu Val Thr Val Ser Ser
                115                 120                 125

<210> SEQ ID NO 16
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Arg Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

```
Leu Gln Met Asn Ser Leu Arg Ala Glu Asp Thr Ala Val Tyr Tyr Cys
                85                  90                  95

Ala Arg Glu Pro Arg Val Gly Tyr Tyr Tyr Glu Thr Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 17
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Thr Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 18
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125
```

```
<210> SEQ ID NO 19
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Arg Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 20
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 21
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 21

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125
```

<210> SEQ ID NO 22
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125
```

<210> SEQ ID NO 23
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Arg Ser Tyr
            20                  25                  30

Gly Met His Trp Val Arg Gln Ala Pro Gly Lys Gly Leu Glu Trp Val
```

```
                35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Met Tyr
 65                 70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
            115                 120                 125

<210> SEQ ID NO 24
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ile Phe Arg Ser Tyr
                20                  25                  30

Gly Met His Trp Val Arg Gln Ala Pro Gly Lys Gly Pro Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
            115                 120                 125

<210> SEQ ID NO 25
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Ser Tyr
                20                  25                  30

Gly Met His Trp Val Arg Gln Ala Pro Gly Lys Gly Leu Glu Gly Val
            35                  40                  45

Ala Val Ile Trp Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
```

```
                    85                  90                  95

Ala Arg Glu Pro Arg Ile Gly Tyr Tyr Tyr Glu Ser Ser Gly Tyr Tyr
                100                 105                 110

Ser Leu Asp Tyr Arg Gly Gln Gly Thr Leu Val Thr Val Ser Ser
            115                 120                 125

<210> SEQ ID NO 26
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ile Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
                100                 105                 110

Ser Leu Asp Tyr Arg Gly Gln Gly Thr Leu Val Thr Val Ser Ser
            115                 120                 125

<210> SEQ ID NO 27
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Pro Glu Trp Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
                100                 105                 110

Ser Leu Asp Tyr Arg Gly Gln Gly Thr Leu Val Thr Val Ser Ser
            115                 120                 125
```

```
<210> SEQ ID NO 28
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
                100                 105                 110

Ser Leu Asp Tyr Arg Gly Gln Gly Thr Leu Val Thr Val Ser Ser
            115                 120                 125

<210> SEQ ID NO 29
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Arg Tyr
                20                  25                  30

Gly Met His Trp Val Arg Gln Ala Pro Gly Lys Gly Leu Glu Gly Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Tyr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Asp Ser Ser Gly Tyr Asp
                100                 105                 110

Ser Leu Asp Tyr Arg Gly Gln Gly Thr Leu Val Thr Val Ser Ser
            115                 120                 125

<210> SEQ ID NO 30
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 31
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 32
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Glu Ser Val Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Gly Val
        35                  40                  45

```
Ala Val Ile Trp Tyr Asp Gly Ser Asn Arg Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
            115                 120                 125

<210> SEQ ID NO 33
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Ser Tyr
                20                  25                  30

Gly Met His Trp Val Arg Gln Ala Pro Gly Lys Gly Leu Glu Gly Val
            35                  40                  45

Ala Val Ile Ser Tyr Asp Gly Ser Asn Arg Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
            115                 120                 125

<210> SEQ ID NO 34
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Met Tyr
 65                  70                  75                  80

Leu Gln Met Asn Ser Leu Arg Ala Glu Asp Thr Ala Val Tyr Tyr Cys
                85                  90                  95
```

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 35
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Ser Tyr
                20                  25                  30

Gly Met His Trp Val Arg Gln Ala Pro Gly Lys Gly Pro Glu Trp Val
            35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser
        115                 120                 125

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Phe Thr Phe Asp Asp Tyr Ala
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ile Ser Trp Asn Ser Gly Ser Ile
1               5

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 38

Ala Lys Asp Ser Arg Gly Tyr Gly Asp Tyr Arg Leu Gly Gly Ala Tyr
1               5                   10                  15

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ser Val Ser Ser Asn
1               5

<210> SEQ ID NO 40
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Ala Ser
1

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Gln Tyr Asn Asn Trp Pro Trp Thr
1               5

<210> SEQ ID NO 42
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110
```

-continued

```
Trp Gly Gln Gly Thr Leu Val Thr Val Ser Ser
            115                 120

<210> SEQ ID NO 43
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 44
<211> LENGTH: 329
<212> TYPE: PRT
<213> ORGANISM: Homo sapiens

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
    275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 45
<211> LENGTH: 327
<212> TYPE: PRT
<213> ORGANISM: Homo sapiens

<400> SEQUENCE: 45

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
    115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

-continued

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 46
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn

```
                   260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 47
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
        290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 49
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Asn Trp Pro Trp
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
```

-continued

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 50
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

Glu Val His Asn Ala Lys Thr Lys Pro Arg Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 51
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val

```
                180             185             190
Thr Val Pro Ser Ser Leu Gly Thr Gln Thr Tyr Ile Cys Asn Val
            195             200             205
Asn His Lys Pro Ser Asn Thr Lys Val Asp Lys Val Glu Pro Lys
        210             215             220
Ser Cys Asp Lys Thr His Thr Cys Pro Pro Cys Pro Ala Pro Glu Ala
225             230             235             240
Ala Gly Gly Pro Ser Val Phe Leu Phe Pro Pro Lys Pro Lys Asp Thr
                245             250             255
Leu Met Ile Ser Arg Thr Pro Glu Val Thr Cys Val Val Val Asp Val
            260             265             270
Ser His Glu Asp Pro Glu Val Lys Phe Asn Trp Tyr Val Asp Gly Val
        275             280             285
Glu Val His Asn Ala Lys Thr Lys Pro Arg Glu Glu Gln Tyr Asn Ser
    290             295             300
Thr Tyr Arg Val Val Ser Val Leu Thr Val Leu His Gln Asp Trp Leu
305             310             315             320
Asn Gly Lys Glu Tyr Lys Cys Lys Val Ser Asn Lys Ala Leu Pro Ala
                325             330             335
Pro Ile Glu Lys Thr Ile Ser Lys Ala Lys Gly Gln Pro Arg Glu Pro
                340             345             350
Gln Val Tyr Thr Leu Pro Pro Ser Arg Glu Glu Met Thr Lys Asn Gln
            355             360             365
Val Ser Leu Thr Cys Leu Val Lys Gly Phe Tyr Pro Ser Asp Ile Ala
        370             375             380
Val Glu Trp Glu Ser Asn Gly Gln Pro Glu Asn Asn Tyr Lys Thr Thr
385             390             395             400
Pro Pro Val Leu Asp Ser Asp Gly Ser Phe Phe Leu Tyr Ser Lys Leu
                405             410             415
Thr Val Asp Lys Ser Arg Trp Gln Gln Gly Asn Val Phe Ser Cys Ser
            420             425             430
Val Met His Glu Ala Leu His Asn His Tyr Thr Gln Lys Ser Leu Ser
        435             440             445
Leu Ser Pro Gly Lys
    450

<210> SEQ ID NO 52
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ala Met His Trp Val Arg Gln Ala Pro Gly Lys Gly Leu Glu Trp Val
        35                  40                  45
Ser Gly Ile Ser Trp Asn Ser Gly Ser Ile Gly Tyr Ala Asp Ser Val
    50                  55                  60
Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 53
<211> LENGTH: 450
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 53

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

```
Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 54
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 55
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55
```

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 56
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 57
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr

```
            20                  25                  30
Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
            210                 215                 220

Tyr Gly Pro Pro Cys Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Ser Cys Ala Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445
```

Gly Lys
    450

<210> SEQ ID NO 58
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp His Arg Gly Gln Gly
            100                 105                 110

Thr Leu Val Thr Val Ser Ser Gly Gly Gly Gly Ser Glu Val Gln Leu
        115                 120                 125

Leu Glu Ser Gly Gly Gly Leu Val Gln Pro Gly Gly Ser Leu Arg Leu
    130                 135                 140

Ser Cys Ala Ala Ser Gly Phe Thr Val Ser Ser Tyr Gly Met Ser Trp
145                 150                 155                 160

Val Arg Gln Ala Pro Gly Lys Gly Pro Glu Trp Val Ser Gly Ile Arg
                165                 170                 175

Gly Ser Asp Gly Ser Thr Tyr Tyr Ala Asp Ser Val Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Ala Lys Gln Gly
    210                 215                 220

Glu Asn Asp Gly Pro Phe Asp His Arg Gly Gln Gly Thr Leu Val Thr
225                 230                 235                 240

Val Ser Ser Glu Ser Lys Tyr Gly Pro Pro Cys Pro Pro Cys Pro Ala
                245                 250                 255

Pro Glu Ala Ala Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser Gln Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly

```
                 340                 345                 350
Leu Pro Ser Ser Ile Glu Lys Thr Ile Ser Lys Ala Lys Gly Gln Pro
            355                 360                 365

Arg Glu Pro Gln Val Tyr Thr Leu Pro Pro Ser Gln Glu Glu Met Thr
    370                 375                 380

Lys Asn Gln Val Ser Leu Ser Cys Ala Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Val
            420                 425                 430

Ser Arg Leu Thr Val Asp Lys Ser Arg Trp Gln Glu Gly Asn Val Phe
        435                 440                 445

Ser Cys Ser Val Met His Glu Ala Leu His Asn His Tyr Thr Gln Lys
    450                 455                 460

Ser Leu Ser Leu Ser Leu Gly Lys
465                 470

<210> SEQ ID NO 59
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp His Arg Gly Gln Gly
            100                 105                 110

Thr Leu Val Thr Val Ser Ser Gly Gly Gly Ser Gly Gly Gly Gly
        115                 120                 125

Ser Glu Val Gln Leu Leu Glu Ser Gly Gly Gly Leu Val Gln Pro Gly
    130                 135                 140

Gly Ser Leu Arg Leu Ser Cys Ala Ala Ser Gly Phe Thr Val Ser Ser
145                 150                 155                 160

Tyr Gly Met Ser Trp Val Arg Gln Ala Pro Gly Lys Gly Pro Glu Trp
                165                 170                 175

Val Ser Gly Ile Arg Gly Ser Asp Gly Ser Thr Tyr Tyr Ala Asp Ser
            180                 185                 190

Val Lys Gly Arg Phe Thr Ile Ser Arg Asp Asn Ser Lys Asn Thr Leu
        195                 200                 205

Tyr Leu Gln Met Asn Ser Leu Arg Ala Glu Asp Thr Ala Val Tyr Tyr
    210                 215                 220
```

Cys Ala Lys Gln Gly Glu Asn Asp Gly Pro Phe Asp His Arg Gly Gln
225                 230                 235                 240

Gly Thr Leu Val Thr Val Ser Ser Glu Ser Lys Tyr Gly Pro Pro Cys
            245                 250                 255

Pro Pro Cys Pro Ala Pro Glu Ala Ala Gly Gly Pro Ser Val Phe Leu
        260                 265                 270

Phe Pro Pro Lys Pro Lys Asp Thr Leu Met Ile Ser Arg Thr Pro Glu
    275                 280                 285

Val Thr Cys Val Val Val Asp Val Ser Gln Glu Asp Pro Glu Val Gln
290                 295                 300

Phe Asn Trp Tyr Val Asp Gly Val Glu Val His Asn Ala Lys Thr Lys
305                 310                 315                 320

Pro Arg Glu Glu Gln Phe Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Gly Leu Pro Ser Ser Ile Glu Lys Thr Ile Ser Lys
        355                 360                 365

Ala Lys Gly Gln Pro Arg Glu Pro Gln Val Tyr Thr Leu Pro Pro Ser
370                 375                 380

Gln Glu Glu Met Thr Lys Asn Gln Val Ser Leu Ser Cys Ala Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Val Ser Arg Leu Thr Val Asp Lys Ser Arg Trp Gln
        435                 440                 445

Glu Gly Asn Val Phe Ser Cys Ser Val Met His Glu Ala Leu His Asn
450                 455                 460

His Tyr Thr Gln Lys Ser Leu Ser Leu Gly Lys
465                 470                 475

<210> SEQ ID NO 60
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp His Arg Gly Gln Gly
            100                 105                 110

```
Thr Leu Val Thr Val Ser Ser Glu Ser Lys Tyr Gly Pro Pro Cys Pro
            115                 120                 125

Pro Cys Pro Ala Pro Glu Ala Ala Gly Gly Pro Ser Val Phe Leu Phe
130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
            195                 200                 205

Val Leu His Gln Asp Trp Leu Asn Gly Lys Glu Tyr Lys Cys Lys Val
        210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Ser Cys Ala Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Val Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345

<210> SEQ ID NO 61
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Phe Trp Gly Trp Ile Arg Gln Ser Pro Gly Lys Gly Leu Glu
        35                  40                  45

Trp Ile Gly Ser Ile Asp Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser Glu Ser Lys Tyr Gly Pro Pro Cys
```

```
                    115                 120                 125
Pro Pro Cys Pro Ala Pro Glu Ala Ala Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser Gln Glu Asp Pro Glu Val Gln
                165                 170                 175

Phe Asn Trp Tyr Val Asp Gly Val Glu Val His Asn Ala Lys Thr Lys
            180                 185                 190

Pro Arg Glu Glu Gln Phe Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Gly Leu Pro Ser Ser Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Gln Glu Glu Met Thr Lys Asn Gln Val Ser Leu Ser Cys Ala Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Val Ser Arg Leu Thr Val Asp Lys Ser Arg Trp Gln
305                 310                 315                 320

Glu Gly Asn Val Phe Ser Cys Ser Val Met His Glu Ala Leu His Asn
                325                 330                 335

His Tyr Thr Gln Lys Ser Leu Ser Leu Ser Leu Gly Lys
            340                 345

<210> SEQ ID NO 62
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Phe Trp Gly Trp Ile Arg Gln Ser Pro Gly Lys Gly Leu Glu
        35                  40                  45

Trp Ile Gly Ser Ile Asp Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser Gly Gly Gly Gly Ser Gly Gly Gly
        115                 120                 125
```

Gly Ser Gln Leu Gln Leu Gln Glu Ser Gly Pro Gly Leu Val Lys Pro
    130                 135                 140

Ser Glu Thr Leu Ser Leu Thr Cys Thr Val Ser Gly Ser Ile Ser
145                 150                 155                 160

Ser Ser Asn Tyr Phe Trp Gly Trp Ile Arg Gln Ser Pro Gly Lys Gly
                165                 170                 175

Leu Glu Trp Ile Gly Ser Ile Asp Tyr Ser Gly Tyr Thr Tyr Tyr Asn
            180                 185                 190

Pro Ser Leu Lys Ser Arg Val Thr Ile Ser Val Asp Thr Ser Lys Asn
        195                 200                 205

Gln Phe Ser Leu Lys Leu Ser Ser Val Thr Ala Ala Asp Thr Ala Val
    210                 215                 220

Tyr Asn Cys Ala Arg His Lys Ala Ala Thr Ala Asp Phe Asp Tyr Arg
225                 230                 235                 240

Gly Gln Gly Thr Leu Val Thr Val Ser Ser Glu Ser Lys Tyr Gly Pro
                245                 250                 255

Pro Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Gln Glu Glu Met Thr Lys Asn Gln Val Ser Leu Ser Cys Ala
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Val Ser Arg Leu Thr Val Asp Lys Ser Arg
        435                 440                 445

Trp Gln Glu Gly Asn Val Phe Ser Cys Ser Val Met His Glu Ala Leu
    450                 455                 460

His Asn His Tyr Thr Gln Lys Ser Leu Ser Leu Ser Leu Gly Lys
465                 470                 475

<210> SEQ ID NO 63
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Arg Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser Glu
        115                 120                 125

Ser Lys Tyr Gly Pro Pro Cys Pro Pro Cys Pro Ala Pro Glu Ala Ala
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

Gln Glu Asp Pro Glu Val Gln Phe Asn Trp Tyr Val Asp Gly Val Glu
            180                 185                 190

Val His Asn Ala Lys Thr Lys Pro Arg Glu Glu Gln Phe Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Gly Leu Pro Ser Ser
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Gln Glu Glu Met Thr Lys Asn Gln Val
            260                 265                 270

Ser Leu Ser Cys Ala Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Val Ser Arg Leu Thr
305                 310                 315                 320

Val Asp Lys Ser Arg Trp Gln Glu Gly Asn Val Phe Ser Cys Ser Val
                325                 330                 335

Met His Glu Ala Leu His Asn His Tyr Thr Gln Lys Ser Leu Ser Leu
            340                 345                 350

Ser Leu Gly Lys
        355

<210> SEQ ID NO 64
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Val Glu Ser Gly Gly Gly Val Val Gln Pro Gly Arg

-continued

```
1               5                   10                  15
Ser Leu Arg Leu Ser Cys Ala Ala Ser Gly Phe Ser Phe Ser Arg Tyr
            20                  25                  30
Gly Met His Trp Val Arg Gln Ala Pro Gly Lys Gly Leu Glu Gly Val
            35                  40                  45
Ala Val Ile Trp Tyr Asp Gly Ser Asn Arg Tyr Tyr Ala Asp Ser Val
            50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Pro Arg Ile Gly Tyr Tyr Tyr Glu Ser Ser Gly Tyr Tyr
                100                 105                 110
Ser Leu Asp Tyr Arg Gly Gln Gly Thr Leu Val Thr Val Ser Ser Gly
                115                 120                 125
Gly Gly Gly Ser Gly Gly Gly Ser Gln Val Gln Leu Val Glu Ser
            130                 135                 140
Gly Gly Gly Val Val Gln Pro Gly Arg Ser Leu Arg Leu Ser Cys Ala
145                 150                 155                 160
Ala Ser Gly Phe Ser Phe Ser Arg Tyr Gly Met His Trp Val Arg Gln
                165                 170                 175
Ala Pro Gly Lys Gly Leu Glu Gly Val Ala Val Ile Trp Tyr Asp Gly
                180                 185                 190
Ser Asn Arg Tyr Tyr Ala Asp Ser Val Lys Gly Arg Phe Thr Ile Ser
                195                 200                 205
Arg Asp Asn Ser Lys Asn Thr Leu Tyr Leu Gln Met Asn Ser Leu Arg
            210                 215                 220
Ala Glu Asp Thr Ala Val Tyr Tyr Cys Ala Arg Glu Pro Arg Ile Gly
225                 230                 235                 240
Tyr Tyr Tyr Glu Ser Ser Gly Tyr Tyr Ser Leu Asp Tyr Arg Gly Gln
                245                 250                 255
Gly Thr Leu Val Thr Val Ser Ser Glu Ser Lys Tyr Gly Pro Pro Cys
            260                 265                 270
Pro Pro Cys Pro Ala Pro Glu Ala Ala Gly Gly Pro Ser Val Phe Leu
            275                 280                 285
Phe Pro Pro Lys Pro Lys Asp Thr Leu Met Ile Ser Arg Thr Pro Glu
            290                 295                 300
Val Thr Cys Val Val Val Asp Val Ser Gln Glu Asp Pro Glu Val Gln
305                 310                 315                 320
Phe Asn Trp Tyr Val Asp Gly Val Glu Val His Asn Ala Lys Thr Lys
                325                 330                 335
Pro Arg Glu Glu Gln Phe Asn Ser Thr Tyr Arg Val Val Ser Val Leu
            340                 345                 350
Thr Val Leu His Gln Asp Trp Leu Asn Gly Lys Glu Tyr Lys Cys Lys
            355                 360                 365
Val Ser Asn Lys Gly Leu Pro Ser Ser Ile Glu Lys Thr Ile Ser Lys
            370                 375                 380
Ala Lys Gly Gln Pro Arg Glu Pro Gln Val Tyr Thr Leu Pro Pro Ser
385                 390                 395                 400
Gln Glu Glu Met Thr Lys Asn Gln Val Ser Leu Ser Cys Ala Val Lys
                405                 410                 415
Gly Phe Tyr Pro Ser Asp Ile Ala Val Glu Trp Glu Ser Asn Gly Gln
                420                 425                 430
```

```
Pro Glu Asn Asn Tyr Lys Thr Thr Pro Pro Val Leu Asp Ser Asp Gly
            435                 440                 445

Ser Phe Phe Leu Val Ser Arg Leu Thr Val Asp Lys Ser Arg Trp Gln
    450                 455                 460

Glu Gly Asn Val Phe Ser Cys Ser Val Met His Glu Ala Leu His Asn
465                 470                 475                 480

His Tyr Thr Gln Lys Ser Leu Ser Leu Ser Leu Gly Lys
            485                 490
```

<210> SEQ ID NO 65
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Phe Trp Gly Trp Ile Arg Gln Ser Pro Gly Lys Gly Leu Glu
        35                  40                  45

Trp Ile Gly Ser Ile Asp Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
            85                  90                  95

Cys Ala Arg His Lys Ala Ala Thr Ala Asp Phe Asp Tyr Arg Gly Gln
        100                 105                 110

Gly Thr Leu Val Thr Val Ser Ser Gly Gly Gly Ser Gly Gly Gly Gly
        115                 120                 125

Gly Ser Gln Val Gln Leu Val Glu Ser Gly Gly Val Val Gln Pro
130                 135                 140

Gly Arg Ser Leu Arg Leu Ser Cys Ala Ala Ser Gly Phe Ser Phe Ser
145                 150                 155                 160

Arg Tyr Gly Met His Trp Val Arg Gln Ala Pro Gly Lys Gly Leu Glu
            165                 170                 175

Gly Val Ala Val Ile Trp Tyr Asp Gly Ser Asn Arg Tyr Tyr Ala Asp
        180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Arg Glu Pro Arg Ile Gly Tyr Tyr Glu Ser Ser Gly
225                 230                 235                 240

Tyr Tyr Ser Leu Asp Tyr Arg Gly Gln Gly Thr Leu Val Thr Val Ser
            245                 250                 255

Ser Glu Ser Lys Tyr Gly Pro Pro Cys Pro Pro Cys Pro Ala Pro Glu
        260                 265                 270

Ala Ala Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
```

```
                290                 295                 300
Val Ser Gln Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
                325                 330                 335

Ser Thr Tyr Arg Val Val Ser Val Leu Thr Val Leu His Gln Asp Trp
                340                 345                 350

Leu Asn Gly Lys Glu Tyr Lys Cys Lys Val Ser Asn Lys Gly Leu Pro
                355                 360                 365

Ser Ser Ile Glu Lys Thr Ile Ser Lys Ala Lys Gly Gln Pro Arg Glu
                370                 375                 380

Pro Gln Val Tyr Thr Leu Pro Pro Ser Gln Glu Met Thr Lys Asn
385                 390                 395                 400

Gln Val Ser Leu Ser Cys Ala Val Lys Gly Phe Tyr Pro Ser Asp Ile
                405                 410                 415

Ala Val Glu Trp Glu Ser Asn Gly Gln Pro Glu Asn Asn Tyr Lys Thr
                420                 425                 430

Thr Pro Pro Val Leu Asp Ser Asp Gly Ser Phe Phe Leu Val Ser Arg
                435                 440                 445

Leu Thr Val Asp Lys Ser Arg Trp Gln Glu Gly Asn Val Phe Ser Cys
                450                 455                 460

Ser Val Met His Glu Ala Leu His Asn His Tyr Thr Gln Lys Ser Leu
465                 470                 475                 480

Ser Leu Ser Leu Gly Lys
                485
```

<210> SEQ ID NO 66
<211> LENGTH: 486
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Arg Tyr
                20                  25                  30

Gly Met His Trp Val Arg Gln Ala Pro Gly Lys Gly Leu Glu Gly Val
            35                  40                  45

Ala Val Ile Trp Tyr Asp Gly Ser Asn Arg Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
                100                 105                 110

Ser Leu Asp Tyr Arg Gly Gln Gly Thr Leu Val Thr Val Ser Ser Gly
            115                 120                 125

Gly Gly Gly Ser Gly Gly Gly Ser Gln Leu Gln Leu Gln Glu Ser
        130                 135                 140

Gly Pro Gly Leu Val Lys Pro Ser Glu Thr Leu Ser Leu Thr Cys Thr
145                 150                 155                 160
```

```
Val Ser Gly Gly Ser Ile Ser Ser Asn Tyr Phe Trp Gly Trp Ile
            165                 170                 175

Arg Gln Ser Pro Gly Lys Gly Leu Glu Trp Ile Gly Ser Ile Asp Tyr
        180                 185                 190

Ser Gly Tyr Thr Tyr Tyr Asn Pro Ser Leu Lys Ser Arg Val Thr Ile
        195                 200                 205

Ser Val Asp Thr Ser Lys Asn Gln Phe Ser Leu Lys Leu Ser Ser Val
    210                 215                 220

Thr Ala Ala Asp Thr Ala Val Tyr Asn Cys Ala Arg His Lys Ala Ala
225                 230                 235                 240

Thr Ala Asp Phe Asp Tyr Arg Gly Gln Gly Thr Leu Val Thr Val Ser
                245                 250                 255

Ser Glu Ser Lys Tyr Gly Pro Pro Cys Pro Pro Cys Pro Ala Pro Glu
            260                 265                 270

Ala Ala Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
    290                 295                 300

Val Ser Gln Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Gly Leu Pro
        355                 360                 365

Ser Ser Ile Glu Lys Thr Ile Ser Lys Ala Lys Gly Gln Pro Arg Glu
    370                 375                 380

Pro Gln Val Tyr Thr Leu Pro Pro Ser Gln Glu Glu Met Thr Lys Asn
385                 390                 395                 400

Gln Val Ser Leu Ser Cys Ala Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Val Ser Arg
        435                 440                 445

Leu Thr Val Asp Lys Ser Arg Trp Gln Glu Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Leu Gly Lys
            485

<210> SEQ ID NO 67
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30
```

-continued

```
Trp Met Ser Trp Val Arg Gln Ala Pro Gly Lys Gly Leu Glu Trp Val
        35                  40                  45

Ala Thr Ile Ser Gln Ala Gly Ser Glu Lys Asp Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Val Tyr Ser Phe Asp Tyr Arg Gly Gln Gly Thr Leu Val
            100                 105                 110

Thr Val Ser Ser Glu Ser Lys Tyr Gly Pro Pro Cys Pro Pro Cys Pro
        115                 120                 125

Ala Pro Glu Ala Ala Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser Gln Glu Asp Pro Glu Val Gln Phe Asn Trp Tyr
                165                 170                 175

Val Asp Gly Val Glu Val His Asn Ala Lys Thr Lys Pro Arg Glu Glu
            180                 185                 190

Gln Phe Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Gly Leu Pro Ser Ser Ile Glu Lys Thr Ile Ser Lys Ala Lys Gly Gln
225                 230                 235                 240

Pro Arg Glu Pro Gln Val Tyr Thr Leu Pro Pro Ser Gln Glu Glu Met
                245                 250                 255

Thr Lys Asn Gln Val Ser Leu Ser Cys Ala Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Val Ser Arg Leu Thr Val Asp Lys Ser Arg Trp Gln Glu Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Leu Gly Lys
            340                 345

<210> SEQ ID NO 68
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Trp Met Ser Trp Val Arg Gln Ala Pro Gly Lys Gly Leu Glu Trp Val
```

```
            35                  40                  45
Ala Thr Ile Ser Gln Ala Gly Ser Glu Lys Asp Tyr Val Asp Ser Val
 50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Val Tyr Tyr Cys
                 85                  90                  95

Ala Ser Gly Val Tyr Ser Phe Asp Tyr Arg Gly Gln Gly Thr Leu Val
                100                 105                 110

Thr Val Ser Ser Gly Gly Gly Ser Glu Val Gln Leu Val Glu Ser
            115                 120                 125

Gly Gly Gly Leu Val Gln Pro Gly Gly Ser Leu Arg Leu Ser Cys Ala
        130                 135                 140

Ala Ser Gly Phe Ser Phe Ser Asp Phe Trp Met Ser Trp Val Arg Gln
145                 150                 155                 160

Ala Pro Gly Lys Gly Leu Glu Trp Val Ala Thr Ile Ser Gln Ala Gly
                165                 170                 175

Ser Glu Lys Asp Tyr Val Asp Ser Val Lys Gly Arg Phe Thr Ile Ser
                180                 185                 190

Arg Asp Asn Ala Lys Lys Ser Leu Tyr Leu Gln Met Asn Ser Leu Arg
        195                 200                 205

Ala Glu Asp Thr Ala Val Tyr Tyr Cys Ala Ser Gly Val Tyr Ser Phe
210                 215                 220

Asp Tyr Arg Gly Gln Gly Thr Leu Val Thr Val Ser Ser Glu Ser Lys
225                 230                 235                 240

Tyr Gly Pro Pro Cys Pro Cys Pro Ala Pro Glu Ala Ala Gly Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
        290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
                340                 345                 350

Lys Thr Ile Ser Lys Ala Lys Gly Gln Pro Arg Glu Pro Gln Val Tyr
            355                 360                 365

Thr Leu Pro Pro Ser Gln Glu Met Thr Lys Asn Gln Val Ser Leu
        370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
450                 455                 460
```

Gly Lys
465

<210> SEQ ID NO 69
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Trp Met Ser Trp Val Arg Gln Ala Pro Gly Lys Gly Leu Glu Trp Val
        35                  40                  45

Ala Thr Ile Ser Gln Ala Gly Ser Glu Lys Asp Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Val Tyr Ser Phe Asp Tyr Arg Gly Gln Gly Thr Leu Val
            100                 105                 110

Thr Val Ser Ser Gly Gly Gly Ser Gly Gly Gly Ser Gly Gly Ser Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Ser Phe Ser Asp Phe Trp Met
145                 150                 155                 160

Ser Trp Val Arg Gln Ala Pro Gly Lys Gly Leu Glu Trp Val Ala Thr
                165                 170                 175

Ile Ser Gln Ala Gly Ser Glu Lys Asp Tyr Val Asp Ser Val Lys Gly
            180                 185                 190

Arg Phe Thr Ile Ser Arg Asp Asn Ala Lys Lys Ser Leu Tyr Leu Gln
        195                 200                 205

Met Asn Ser Leu Arg Ala Glu Asp Thr Ala Val Tyr Tyr Cys Ala Ser
    210                 215                 220

Gly Val Tyr Ser Phe Asp Tyr Arg Gly Gln Gly Thr Leu Val Thr Val
225                 230                 235                 240

Ser Ser Glu Ser Lys Tyr Gly Pro Pro Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu

```
                    340                 345                 350
Pro Ser Ser Ile Glu Lys Thr Ile Ser Lys Ala Lys Gly Gln Pro Arg
            355                 360                 365

Glu Pro Gln Val Tyr Thr Leu Pro Pro Ser Gln Glu Met Thr Lys
        370                 375                 380

Asn Gln Val Ser Leu Ser Cys Ala Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Val Ser
            420                 425                 430

Arg Leu Thr Val Asp Lys Ser Arg Trp Gln Glu Gly Asn Val Phe Ser
        435                 440                 445

Cys Ser Val Met His Glu Ala Leu His Asn His Tyr Thr Gln Lys Ser
    450                 455                 460

Leu Ser Leu Ser Leu Gly Lys
465                 470

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gly Gly Gly Ser
1               5

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Gly Gly Gly Ser Gly Gly Gly Gly Ser
1               5                   10

<210> SEQ ID NO 72
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Ser Cys Ala Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Val Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 73
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

100                 105                 110
Glu Ala Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Trp Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 74
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-10 "Gly Gly Gly
      Gly Ser" repeating units
<220> FEATURE:
<223> OTHER INFORMATION: See specification as filed for detailed
      description of substitutions and preferred embodiments

<400> SEQUENCE: 74

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Gly Ser Gly Gly Gly Ser Gly Gly Gly
            35                  40                  45

Gly Ser
    50

<210> SEQ ID NO 75
<211> LENGTH: 449
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 75

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Trp Cys Leu Val Lys Gly Phe Tyr Pro Ser Asp Ile Ala Val Glu Trp
    370                 375                 380

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly

<210> SEQ ID NO 76
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gln Gly Glu Asn Asp Gly Pro Phe Asp His Arg Gly Gln Gly
        100                 105                 110

Thr Leu Val Thr Val Ser Ser Gly Gly Gly Ser Glu Val Gln Leu
            115                 120                 125

Leu Glu Ser Gly Gly Gly Leu Val Gln Pro Gly Gly Ser Leu Arg Leu
    130                 135                 140

Ser Cys Ala Ala Ser Gly Phe Thr Val Ser Ser Tyr Gly Met Ser Trp
145                 150                 155                 160

Val Arg Gln Ala Pro Gly Lys Gly Pro Glu Trp Val Ser Gly Ile Arg
            165                 170                 175

Gly Ser Asp Gly Ser Thr Tyr Tyr Ala Asp Ser Val Lys Gly Arg Phe
        180                 185                 190

Thr Ile Ser Arg Asp Asn Ser Lys Asn Thr Leu Tyr Leu Gln Met Asn
    195                 200                 205

Ser Leu Arg Ala Glu Asp Thr Ala Val Tyr Tyr Cys Ala Lys Gln Gly
    210                 215                 220

Glu Asn Asp Gly Pro Phe Asp His Arg Gly Gln Gly Thr Leu Val Thr
225                 230                 235                 240

Val Ser Ser Glu Ser Lys Tyr Gly Pro Pro Cys Pro Pro Cys Pro Ala
            245                 250                 255

Pro Glu Ala Ala Gly Gly Pro Ser Val Phe Leu Phe Pro Pro Lys Pro
        260                 265                 270

Lys Asp Thr Leu Met Ile Ser Arg Thr Pro Glu Val Thr Cys Val Val
    275                 280                 285
```

```
Val Asp Val Ser Gln Glu Asp Pro Glu Val Gln Phe Asn Trp Tyr Val
290                 295                 300

Asp Gly Val Glu Val His Asn Ala Lys Thr Lys Pro Arg Glu Glu Gln
305                 310                 315                 320

Phe Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
        355                 360                 365

Arg Glu Pro Gln Val Tyr Thr Leu Pro Pro Ser Gln Glu Glu Met Thr
370                 375                 380

Lys Asn Gln Val Ser Leu Ser Cys Ala Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Val
            420                 425                 430

Ser Arg Leu Thr Val Asp Lys Ser Arg Trp Gln Glu Gly Asn Val Phe
        435                 440                 445

Ser Cys Ser Val Met His Glu Ala Leu His Asn His Tyr Thr Gln Lys
450                 455                 460

Ser Leu Ser Leu Ser Leu Gly
465                 470

<210> SEQ ID NO 77
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Glu Asn Asp Gly Pro Phe Asp His Arg Gly Gln Gly
            100                 105                 110

Thr Leu Val Thr Val Ser Ser Gly Gly Gly Ser Gly Gly Gly Gly
        115                 120                 125

Ser Glu Val Gln Leu Leu Glu Ser Gly Gly Gly Leu Val Gln Pro Gly
    130                 135                 140

Gly Ser Leu Arg Leu Ser Cys Ala Ala Ser Gly Phe Thr Val Ser Ser
145                 150                 155                 160

Tyr Gly Met Ser Trp Val Arg Gln Ala Pro Gly Lys Gly Pro Glu Trp
                165                 170                 175
```

```
Val Ser Gly Ile Arg Gly Ser Asp Gly Ser Thr Tyr Tyr Ala Asp Ser
            180                 185                 190

Val Lys Gly Arg Phe Thr Ile Ser Arg Asp Asn Ser Lys Asn Thr Leu
            195                 200                 205

Tyr Leu Gln Met Asn Ser Leu Arg Ala Glu Asp Thr Ala Val Tyr Tyr
            210                 215                 220

Cys Ala Lys Gln Gly Glu Asn Asp Gly Pro Phe Asp His Arg Gly Gln
225                 230                 235                 240

Gly Thr Leu Val Thr Val Ser Ser Glu Ser Lys Tyr Gly Pro Pro Cys
                245                 250                 255

Pro Pro Cys Pro Ala Pro Glu Ala Ala Gly Gly Pro Ser Val Phe Leu
                260                 265                 270

Phe Pro Pro Lys Pro Lys Asp Thr Leu Met Ile Ser Arg Thr Pro Glu
                275                 280                 285

Val Thr Cys Val Val Val Asp Val Ser Gln Glu Asp Pro Glu Val Gln
            290                 295                 300

Phe Asn Trp Tyr Val Asp Gly Val Glu Val His Asn Ala Lys Thr Lys
305                 310                 315                 320

Pro Arg Glu Glu Gln Phe Asn Ser Thr Tyr Arg Val Val Ser Val Leu
                325                 330                 335

Thr Val Leu His Gln Asp Trp Leu Asn Gly Lys Glu Tyr Lys Cys Lys
                340                 345                 350

Val Ser Asn Lys Gly Leu Pro Ser Ser Ile Glu Lys Thr Ile Ser Lys
            355                 360                 365

Ala Lys Gly Gln Pro Arg Glu Pro Gln Val Tyr Thr Leu Pro Pro Ser
            370                 375                 380

Gln Glu Glu Met Thr Lys Asn Gln Val Ser Leu Ser Cys Ala Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
                420                 425                 430

Ser Phe Phe Leu Val Ser Arg Leu Thr Val Asp Lys Ser Arg Trp Gln
            435                 440                 445

Glu Gly Asn Val Phe Ser Cys Ser Val Met His Glu Ala Leu His Asn
            450                 455                 460

His Tyr Thr Gln Lys Ser Leu Ser Leu Ser Leu Gly
            465                 470                 475

<210> SEQ ID NO 78
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Trp Met Ser Trp Val Arg Gln Ala Pro Gly Lys Gly Leu Glu Trp Val
            35                  40                  45

Ala Thr Ile Ser Gln Ala Gly Ser Glu Lys Asp Tyr Val Asp Ser Val
```

```
                      50                  55                  60
Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Val Tyr Tyr Cys
                 85                  90                  95

Ala Ser Gly Val Tyr Ser Phe Asp Tyr Arg Gly Gln Gly Thr Leu Val
            100                 105                 110

Thr Val Ser Ser Glu Ser Lys Tyr Gly Pro Pro Cys Pro Pro Cys Pro
        115                 120                 125

Ala Pro Glu Ala Ala Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser Gln Glu Asp Pro Glu Val Gln Phe Asn Trp Tyr
                165                 170                 175

Val Asp Gly Val Glu Val His Asn Ala Lys Thr Lys Pro Arg Glu Glu
            180                 185                 190

Gln Phe Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Gly Leu Pro Ser Ser Ile Glu Lys Thr Ile Ser Lys Ala Lys Gly Gln
225                 230                 235                 240

Pro Arg Glu Pro Gln Val Tyr Thr Leu Pro Pro Ser Gln Glu Glu Met
                245                 250                 255

Thr Lys Asn Gln Val Ser Leu Ser Cys Ala Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Val Ser Arg Leu Thr Val Asp Lys Ser Arg Trp Gln Glu Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Leu Gly
            340

<210> SEQ ID NO 79
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ser Phe Ser Asp Phe
                 20                  25                  30

Trp Met Ser Trp Val Arg Gln Ala Pro Gly Lys Gly Leu Glu Trp Val
             35                  40                  45

Ala Thr Ile Ser Gln Ala Gly Ser Glu Lys Asp Tyr Val Asp Ser Val
         50                  55                  60
```

```
Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Val Tyr Tyr Cys
                 85                  90                  95

Ala Ser Gly Val Tyr Ser Phe Asp Tyr Arg Gly Gln Gly Thr Leu Val
            100                 105                 110

Thr Val Ser Ser Gly Gly Gly Ser Glu Val Gln Leu Val Glu Ser
        115                 120                 125

Gly Gly Gly Leu Val Gln Pro Gly Gly Ser Leu Arg Leu Ser Cys Ala
    130                 135                 140

Ala Ser Gly Phe Ser Phe Ser Asp Phe Trp Met Ser Trp Val Arg Gln
145                 150                 155                 160

Ala Pro Gly Lys Gly Leu Glu Trp Val Ala Thr Ile Ser Gln Ala Gly
            165                 170                 175

Ser Glu Lys Asp Tyr Val Asp Ser Val Lys Gly Arg Phe Thr Ile Ser
            180                 185                 190

Arg Asp Asn Ala Lys Lys Ser Leu Tyr Leu Gln Met Asn Ser Leu Arg
            195                 200                 205

Ala Glu Asp Thr Ala Val Tyr Tyr Cys Ala Ser Gly Val Tyr Ser Phe
210                 215                 220

Asp Tyr Arg Gly Gln Gly Thr Leu Val Thr Val Ser Ser Glu Ser Lys
225                 230                 235                 240

Tyr Gly Pro Pro Cys Pro Pro Cys Pro Ala Pro Glu Ala Ala Gly Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
            275                 280                 285

Asp Pro Glu Val Gln Phe Asn Trp Tyr Val Asp Gly Val Glu Val His
            290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Gln Glu Glu Met Thr Lys Asn Gln Val Ser Leu
            370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Arg Leu Thr Val Asp
            420                 425                 430

Lys Ser Arg Trp Gln Glu Gly Asn Val Phe Ser Cys Ser Val Met His
            435                 440                 445

Glu Ala Leu His Asn His Tyr Thr Gln Lys Ser Leu Ser Leu Ser Leu
            450                 455                 460

Gly
465
```

<210> SEQ ID NO 80
<211> LENGTH: 470
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Ser | Phe | Ser | Asp | Phe |
| | | | 20 | | | | | 25 | | | | | 30 | | |
| Trp | Met | Ser | Trp | Val | Arg | Gln | Ala | Pro | Gly | Lys | Gly | Leu | Glu | Trp | Val |
| | | 35 | | | | | 40 | | | | | 45 | | | |
| Ala | Thr | Ile | Ser | Gln | Ala | Gly | Ser | Glu | Lys | Asp | Tyr | Val | Asp | Ser | Val |
| | 50 | | | | | 55 | | | | | 60 | | | | |
| Lys | Gly | Arg | Phe | Thr | Ile | Ser | Arg | Asp | Asn | Ala | Lys | Lys | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Ser | Gly | Val | Tyr | Ser | Phe | Asp | Tyr | Arg | Gly | Gln | Gly | Thr | Leu | Val |
| | | | 100 | | | | | 105 | | | | | 110 | | |
| Thr | Val | Ser | Ser | Gly | Gly | Gly | Gly | Ser | Gly | Gly | Gly | Gly | Ser | Glu | Val |
| | | 115 | | | | | 120 | | | | | 125 | | | |
| Gln | Leu | Val | Glu | Ser | Gly | Gly | Gly | Leu | Val | Gln | Pro | Gly | Gly | Ser | Leu |
| | 130 | | | | | 135 | | | | | 140 | | | | |
| Arg | Leu | Ser | Cys | Ala | Ala | Ser | Gly | Phe | Ser | Phe | Ser | Asp | Phe | Trp | Met |
| 145 | | | | | 150 | | | | | 155 | | | | | 160 |
| Ser | Trp | Val | Arg | Gln | Ala | Pro | Gly | Lys | Gly | Leu | Glu | Trp | Val | Ala | Thr |
| | | | | 165 | | | | | 170 | | | | | 175 | |
| Ile | Ser | Gln | Ala | Gly | Ser | Glu | Lys | Asp | Tyr | Val | Asp | Ser | Val | Lys | Gly |
| | | | 180 | | | | | 185 | | | | | 190 | | |
| Arg | Phe | Thr | Ile | Ser | Arg | Asp | Asn | Ala | Lys | Lys | Ser | Leu | Tyr | Leu | Gln |
| | | 195 | | | | | 200 | | | | | 205 | | | |
| Met | Asn | Ser | Leu | Arg | Ala | Glu | Asp | Thr | Ala | Val | Tyr | Tyr | Cys | Ala | Ser |
| | 210 | | | | | 215 | | | | | 220 | | | | |
| Gly | Val | Tyr | Ser | Phe | Asp | Tyr | Arg | Gly | Gln | Gly | Thr | Leu | Val | Thr | Val |
| 225 | | | | | 230 | | | | | 235 | | | | | 240 |
| Ser | Ser | Glu | Ser | Lys | Tyr | Gly | Pro | Pro | Cys | Pro | Pro | Cys | Pro | Ala | Pro |
| | | | | 245 | | | | | 250 | | | | | 255 | |
| Glu | Ala | Ala | Gly | Gly | Pro | Ser | Val | Phe | Leu | Phe | Pro | Pro | Lys | Pro | Lys |
| | | | 260 | | | | | 265 | | | | | 270 | | |
| Asp | Thr | Leu | Met | Ile | Ser | Arg | Thr | Pro | Glu | Val | Thr | Cys | Val | Val | Val |
| | | 275 | | | | | 280 | | | | | 285 | | | |
| Asp | Val | Ser | Gln | Glu | Asp | Pro | Glu | Val | Gln | Phe | Asn | Trp | Tyr | Val | Asp |
| | 290 | | | | | 295 | | | | | 300 | | | | |
| Gly | Val | Glu | Val | His | Asn | Ala | Lys | Thr | Lys | Pro | Arg | Glu | Glu | Gln | Phe |
| 305 | | | | | 310 | | | | | 315 | | | | | 320 |
| Asn | Ser | Thr | Tyr | Arg | Val | Val | Ser | Val | Leu | Thr | Val | Leu | His | Gln | Asp |
| | | | | 325 | | | | | 330 | | | | | 335 | |
| Trp | Leu | Asn | Gly | Lys | Glu | Tyr | Lys | Cys | Lys | Val | Ser | Asn | Lys | Gly | Leu |
| | | | 340 | | | | | 345 | | | | | 350 | | |
| Pro | Ser | Ser | Ile | Glu | Lys | Thr | Ile | Ser | Lys | Ala | Lys | Gly | Gln | Pro | Arg |
| | | 355 | | | | | 360 | | | | | 365 | | | |

```
Glu Pro Gln Val Tyr Thr Leu Pro Pro Ser Gln Glu Met Thr Lys
    370                 375                 380

Asn Gln Val Ser Leu Ser Cys Ala Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Val Ser
            420                 425                 430

Arg Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Leu Gly
465                 470

<210> SEQ ID NO 81
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Phe Trp Gly Trp Ile Arg Gln Ser Pro Gly Lys Gly Leu Glu
        35                  40                  45

Trp Ile Gly Ser Ile Asp Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser Glu Ser Lys Tyr Gly Pro Pro Cys
        115                 120                 125

Pro Pro Cys Pro Ala Pro Glu Ala Ala Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser Gln Glu Asp Pro Glu Val Gln
                165                 170                 175

Phe Asn Trp Tyr Val Asp Gly Val Glu Val His Asn Ala Lys Thr Lys
            180                 185                 190

Pro Arg Glu Glu Gln Phe Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Gly Leu Pro Ser Ser Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255
```

```
Gln Glu Glu Met Thr Lys Asn Gln Val Ser Leu Ser Cys Ala Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Val Ser Arg Leu Thr Val Asp Lys Ser Arg Trp Gln
305                 310                 315                 320

Glu Gly Asn Val Phe Ser Cys Ser Val Met His Glu Ala Leu His Asn
                325                 330                 335

His Tyr Thr Gln Lys Ser Leu Ser Leu Ser Leu Gly
            340                 345

<210> SEQ ID NO 82
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Phe Trp Gly Trp Ile Arg Gln Ser Pro Gly Lys Gly Leu Glu
        35                  40                  45

Trp Ile Gly Ser Ile Asp Tyr Ser Gly Tyr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
                85                  90                  95

Cys Ala Arg His Lys Ala Ala Thr Ala Asp Phe Asp Tyr Arg Gly Gln
            100                 105                 110

Gly Thr Leu Val Thr Val Ser Ser Gly Gly Gly Ser Gly Gly Gly
        115                 120                 125

Gly Ser Gln Leu Gln Leu Gln Glu Ser Gly Pro Gly Leu Val Lys Pro
    130                 135                 140

Ser Glu Thr Leu Ser Leu Thr Cys Thr Val Ser Gly Gly Ser Ile Ser
145                 150                 155                 160

Ser Ser Asn Tyr Phe Trp Gly Trp Ile Arg Gln Ser Pro Gly Lys Gly
                165                 170                 175

Leu Glu Trp Ile Gly Ser Ile Asp Tyr Ser Gly Tyr Thr Tyr Tyr Asn
            180                 185                 190

Pro Ser Leu Lys Ser Arg Val Thr Ile Ser Val Asp Thr Ser Lys Asn
        195                 200                 205

Gln Phe Ser Leu Lys Leu Ser Ser Val Thr Ala Ala Asp Thr Ala Val
    210                 215                 220

Tyr Asn Cys Ala Arg His Lys Ala Ala Thr Ala Asp Phe Asp Tyr Arg
225                 230                 235                 240

Gly Gln Gly Thr Leu Val Thr Val Ser Ser Glu Ser Lys Tyr Gly Pro
                245                 250                 255

Pro Cys Pro Pro Cys Pro Ala Pro Glu Ala Ala Gly Gly Pro Ser Val
```

```
                260                 265                 270
Phe Leu Phe Pro Pro Lys Pro Lys Asp Thr Leu Met Ile Ser Arg Thr
            275                 280                 285

Pro Glu Val Thr Cys Val Val Val Asp Val Ser Gln Glu Asp Pro Glu
        290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile
        355                 360                 365

Ser Lys Ala Lys Gly Gln Pro Arg Glu Pro Gln Val Tyr Thr Leu Pro
370                 375                 380

Pro Ser Gln Glu Glu Met Thr Lys Asn Gln Val Ser Leu Ser Cys Ala
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Val Ser Arg Leu Thr Val Asp Lys Ser Arg
        435                 440                 445

Trp Gln Glu Gly Asn Val Phe Ser Cys Ser Val Met His Glu Ala Leu
450                 455                 460

His Asn His Tyr Thr Gln Lys Ser Leu Ser Leu Ser Leu Gly
465                 470                 475

<210> SEQ ID NO 83
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Arg Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser Glu
        115                 120                 125

Ser Lys Tyr Gly Pro Pro Cys Pro Pro Cys Pro Ala Pro Glu Ala Ala
    130                 135                 140
```

```
Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Asp Val Ser
                165                 170                 175

Gln Glu Asp Pro Glu Val Gln Phe Asn Trp Tyr Val Asp Gly Val Glu
            180                 185                 190

Val His Asn Ala Lys Thr Lys Pro Arg Glu Glu Gln Phe Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Gly Leu Pro Ser Ser
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Gln Glu Glu Met Thr Lys Asn Gln Val
            260                 265                 270

Ser Leu Ser Cys Ala Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Val Ser Arg Leu Thr
305                 310                 315                 320

Val Asp Lys Ser Arg Trp Gln Glu Gly Asn Val Phe Ser Cys Ser Val
                325                 330                 335

Met His Glu Ala Leu His Asn His Tyr Thr Gln Lys Ser Leu Ser Leu
            340                 345                 350

Ser Leu Gly
        355

<210> SEQ ID NO 84
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Arg Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Pro Arg Ile Gly Tyr Tyr Tyr Glu Ser Ser Gly Tyr Tyr
            100                 105                 110

Ser Leu Asp Tyr Arg Gly Gln Gly Thr Leu Val Thr Val Ser Ser Gly
        115                 120                 125

Gly Gly Gly Ser Gly Gly Gly Gly Ser Gln Val Gln Leu Val Glu Ser
130                 135                 140
```

Gly Gly Gly Val Val Gln Pro Gly Arg Ser Leu Arg Leu Ser Cys Ala
145                 150                 155                 160

Ala Ser Gly Phe Ser Phe Ser Arg Tyr Gly Met His Trp Val Arg Gln
            165                 170                 175

Ala Pro Gly Lys Gly Leu Glu Gly Val Ala Val Ile Trp Tyr Asp Gly
            180                 185                 190

Ser Asn Arg Tyr Tyr Ala Asp Ser Val Lys Gly Arg Phe Thr Ile Ser
            195                 200                 205

Arg Asp Asn Ser Lys Asn Thr Leu Tyr Leu Gln Met Asn Ser Leu Arg
210                 215                 220

Ala Glu Asp Thr Ala Val Tyr Tyr Cys Ala Arg Glu Pro Arg Ile Gly
225                 230                 235                 240

Tyr Tyr Tyr Glu Ser Ser Gly Tyr Tyr Ser Leu Asp Tyr Arg Gly Gln
            245                 250                 255

Gly Thr Leu Val Thr Val Ser Ser Glu Ser Lys Tyr Gly Pro Pro Cys
            260                 265                 270

Pro Pro Cys Pro Ala Pro Glu Ala Ala Gly Gly Pro Ser Val Phe Leu
            275                 280                 285

Phe Pro Pro Lys Pro Lys Asp Thr Leu Met Ile Ser Arg Thr Pro Glu
            290                 295                 300

Val Thr Cys Val Val Val Asp Val Ser Gln Glu Asp Pro Glu Val Gln
305                 310                 315                 320

Phe Asn Trp Tyr Val Asp Gly Val Glu Val His Asn Ala Lys Thr Lys
            325                 330                 335

Pro Arg Glu Glu Gln Phe Asn Ser Thr Tyr Arg Val Val Ser Val Leu
            340                 345                 350

Thr Val Leu His Gln Asp Trp Leu Asn Gly Lys Glu Tyr Lys Cys Lys
            355                 360                 365

Val Ser Asn Lys Gly Leu Pro Ser Ser Ile Glu Lys Thr Ile Ser Lys
370                 375                 380

Ala Lys Gly Gln Pro Arg Glu Pro Gln Val Tyr Thr Leu Pro Pro Ser
385                 390                 395                 400

Gln Glu Glu Met Thr Lys Asn Gln Val Ser Leu Ser Cys Ala Val Lys
            405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
            435                 440                 445

Ser Phe Phe Leu Val Ser Arg Leu Thr Val Asp Lys Ser Arg Trp Gln
            450                 455                 460

Glu Gly Asn Val Phe Ser Cys Ser Val Met His Glu Ala Leu His Asn
465                 470                 475                 480

His Tyr Thr Gln Lys Ser Leu Ser Leu Ser Leu Gly
            485                 490

<210> SEQ ID NO 85
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Leu Gln Leu Gln Glu Ser Gly Pro Gly Leu Val Lys Pro Ser Glu

-continued

```
1               5                    10                   15
Thr Leu Ser Leu Thr Cys Thr Val Ser Gly Gly Ser Ile Ser Ser Ser
             20                  25                  30

Asn Tyr Phe Trp Gly Trp Ile Arg Gln Ser Pro Gly Lys Gly Leu Glu
             35                  40                  45

Trp Ile Gly Ser Ile Asp Tyr Ser Gly Tyr Thr Tyr Asn Pro Ser
     50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Asn
             85                  90                  95

Cys Ala Arg His Lys Ala Ala Thr Ala Asp Phe Asp Tyr Arg Gly Gln
             100                 105                 110

Gly Thr Leu Val Thr Val Ser Ser Gly Gly Gly Gly Ser Gly Gly Gly
             115                 120                 125

Gly Ser Gln Val Gln Leu Val Glu Ser Gly Gly Val Val Gln Pro
     130                 135                 140

Gly Arg Ser Leu Arg Leu Ser Cys Ala Ala Ser Gly Phe Ser Phe Ser
145                 150                 155                 160

Arg Tyr Gly Met His Trp Val Arg Gln Ala Pro Gly Lys Gly Leu Glu
             165                 170                 175

Gly Val Ala Val Ile Trp Tyr Asp Gly Ser Asn Arg Tyr Tyr Ala Asp
             180                 185                 190

Ser Val Lys Gly Arg Phe Thr Ile Ser Arg Asp Asn Ser Lys Asn Thr
             195                 200                 205

Leu Tyr Leu Gln Met Asn Ser Leu Arg Ala Glu Asp Thr Ala Val Tyr
     210                 215                 220

Tyr Cys Ala Arg Glu Pro Arg Ile Gly Tyr Tyr Tyr Glu Ser Ser Gly
225                 230                 235                 240

Tyr Tyr Ser Leu Asp Tyr Arg Gly Gln Gly Thr Leu Val Thr Val Ser
             245                 250                 255

Ser Glu Ser Lys Tyr Gly Pro Pro Cys Pro Pro Cys Pro Ala Pro Glu
             260                 265                 270

Ala Ala Gly Gly Pro Ser Val Phe Leu Phe Pro Pro Lys Pro Lys Asp
             275                 280                 285

Thr Leu Met Ile Ser Arg Thr Pro Glu Val Thr Cys Val Val Val Asp
             290                 295                 300

Val Ser Gln Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
             325                 330                 335

Ser Thr Tyr Arg Val Val Ser Val Leu Thr Val Leu His Gln Asp Trp
             340                 345                 350

Leu Asn Gly Lys Glu Tyr Lys Cys Lys Val Ser Asn Lys Gly Leu Pro
             355                 360                 365

Ser Ser Ile Glu Lys Thr Ile Ser Lys Ala Lys Gly Gln Pro Arg Glu
     370                 375                 380

Pro Gln Val Tyr Thr Leu Pro Pro Ser Gln Glu Glu Met Thr Lys Asn
385                 390                 395                 400

Gln Val Ser Leu Ser Cys Ala Val Lys Gly Phe Tyr Pro Ser Asp Ile
             405                 410                 415

Ala Val Glu Trp Glu Ser Asn Gly Gln Pro Glu Asn Asn Tyr Lys Thr
             420                 425                 430
```

```
Thr Pro Pro Val Leu Asp Ser Asp Gly Ser Phe Phe Leu Val Ser Arg
            435                 440                 445
Leu Thr Val Asp Lys Ser Arg Trp Gln Glu Gly Asn Val Phe Ser Cys
    450                 455                 460
Ser Val Met His Glu Ala Leu His Asn His Tyr Thr Gln Lys Ser Leu
465                 470                 475                 480
Ser Leu Ser Leu Gly
                485

<210> SEQ ID NO 86
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Val Glu Ser Gly Gly Val Val Gln Pro Gly Arg
1               5                   10                  15
Ser Leu Arg Leu Ser Cys Ala Ala Ser Gly Phe Ser Phe Ser Arg Tyr
                20                  25                  30
Gly Met His Trp Val Arg Gln Ala Pro Gly Lys Gly Leu Glu Gly Val
            35                  40                  45
Ala Val Ile Trp Tyr Asp Gly Ser Asn Arg Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Glu Pro Arg Ile Gly Tyr Tyr Tyr Glu Ser Ser Gly Tyr Tyr
            100                 105                 110
Ser Leu Asp Tyr Arg Gly Gln Gly Thr Leu Val Thr Val Ser Ser Gly
        115                 120                 125
Gly Gly Gly Ser Gly Gly Gly Ser Gln Leu Gln Leu Gln Glu Ser
130                 135                 140
Gly Pro Gly Leu Val Lys Pro Ser Glu Thr Leu Ser Leu Thr Cys Thr
145                 150                 155                 160
Val Ser Gly Gly Ser Ile Ser Ser Ser Asn Tyr Phe Trp Gly Trp Ile
                165                 170                 175
Arg Gln Ser Pro Gly Lys Gly Leu Glu Trp Ile Gly Ser Ile Asp Tyr
            180                 185                 190
Ser Gly Tyr Thr Tyr Tyr Asn Pro Ser Leu Lys Ser Arg Val Thr Ile
        195                 200                 205
Ser Val Asp Thr Ser Lys Asn Gln Phe Ser Leu Lys Leu Ser Ser Val
210                 215                 220
Thr Ala Ala Asp Thr Ala Val Tyr Asn Cys Ala Arg His Lys Ala Ala
225                 230                 235                 240
Thr Ala Asp Phe Asp Tyr Arg Gly Gln Gly Thr Leu Val Thr Val Ser
                245                 250                 255
Ser Glu Ser Lys Tyr Gly Pro Pro Cys Pro Pro Cys Pro Ala Pro Glu
            260                 265                 270
Ala Ala Gly Gly Pro Ser Val Phe Leu Phe Pro Pro Lys Pro Lys Asp
        275                 280                 285
Thr Leu Met Ile Ser Arg Thr Pro Glu Val Thr Cys Val Val Val Asp
```

```
            290                 295                 300
Val Ser Gln Glu Asp Pro Glu Val Gln Phe Asn Trp Tyr Val Asp Gly
305                 310                 315                 320

Val Glu Val His Asn Ala Lys Thr Lys Pro Arg Glu Glu Gln Phe Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Gly Leu Pro
        355                 360                 365

Ser Ser Ile Glu Lys Thr Ile Ser Lys Ala Lys Gly Gln Pro Arg Glu
    370                 375                 380

Pro Gln Val Tyr Thr Leu Pro Pro Ser Gln Glu Met Thr Lys Asn
385                 390                 395                 400

Gln Val Ser Leu Ser Cys Ala Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Val Ser Arg
        435                 440                 445

Leu Thr Val Asp Lys Ser Arg Trp Gln Glu Gly Asn Val Phe Ser Cys
    450                 455                 460

Ser Val Met His Glu Ala Leu His Asn His Tyr Thr Gln Lys Ser Leu
465                 470                 475                 480

Ser Leu Ser Leu Gly
                485

<210> SEQ ID NO 87
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Pro Pro Gly Lys Gly Met Glu Trp Val
        35                  40                  45

Ser Gly Ile Arg Gly Ser Asp Gly Ser Thr Phe Tyr Ala Asp Ser Val
    50                  55                  60

Lys Gly Arg Phe Thr Ile Ser Arg Asp Asn Ala Thr Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115

<210> SEQ ID NO 88
<211> LENGTH: 119
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Gly Met Ser Trp Val Arg Gln Ala Pro Gly Lys Gly Val Glu Trp Val
        35                  40                  45

Ser Gly Ile Arg Gly Ser Asp Gly Thr Thr Tyr Tyr Ala Asp Ser Val
    50                  55                  60

Lys Gly Arg Phe Thr Ile Ser Arg Asp Ser Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp His Arg Gly Gln Gly
            100                 105                 110

Thr Leu Val Thr Val Ser Ser
        115

<210> SEQ ID NO 89
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr
            20                  25                  30

Gly Met Ser Trp Val Arg Gln Ala Pro Gly Lys Gly Pro Glu Trp Val
        35                  40                  45

Ser Gly Ile Arg Gly Ser Asp Gly Ser Thr Tyr Tyr Ala Asp Ser Val
    50                  55                  60

Lys Gly Arg Phe Thr Ile Ser Arg Asp Asn Ala Thr Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Gly Gly Asn Asp Gly Pro Phe Asp Tyr Arg Gly Gln Gly
            100                 105                 110

Thr Leu Val Thr Val Ser Ser
        115

<210> SEQ ID NO 90
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 90

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Ser Tyr

```
                    20                  25                  30

Gly Met Ser Trp Val Arg Gln Ala Pro Gly Lys Gly Pro Glu Trp Val
                35                  40                  45

Ser Gly Ile Arg Gly Ser Asp Gly Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Gln Gly Glu Asn Asp Gly Pro Phe Asp His Arg Gly Gln Gly
                100                 105                 110

Thr Leu Val Thr Val Ser Ser
            115

<210> SEQ ID NO 91
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Val Ser Ser Tyr
                20                  25                  30

Gly Met Ser Trp Val Arg Gln Pro Pro Gly Lys Gly Met Glu Trp Val
                35                  40                  45

Ser Gly Ile Arg Gly Ser Asp Gly Ser Thr Tyr Tyr Ala Asp Ser Val
            50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Gln Gly Gly Asn Asp Gly Pro Phe Asp Tyr Arg Gly Gln Gly
                100                 105                 110

Thr Leu Val Thr Val Ser Ser
            115

<210> SEQ ID NO 92
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Leu Glu Ser Gly Gly Gly Leu Val Gln Ala Gly Gly
 1               5                  10                  15

Ser Leu Arg Leu Ser Cys Ala Ala Ser Gly Phe Thr Val Ser Ser Tyr
                20                  25                  30

Gly Met Ser Trp Val Arg Gln Ala Pro Gly Lys Gly Pro Glu Trp Val
                35                  40                  45

Ser Gly Ile Arg Gly Ser Asp Gly Ser Thr Tyr Tyr Ala Asp Ser Val
            50                  55                  60

Lys Gly Arg Phe Thr Ile Ser Arg Asp Asn Ser Lys Asn Thr Leu Tyr
```

-continued

```
            65                  70                  75                  80
Leu Gln Met Asn Ser Leu Arg Ala Glu Asp Thr Ala Val Tyr His Cys
                85                  90                  95

Ala Lys Gln Gly Glu Asn Asp Gly Pro Phe Asp Tyr Arg Gly Gln Gly
                100                 105                 110

Thr Leu Val Thr Val Ser Ser
            115
```